United States Patent
McCasky Feazel et al.

(10) Patent No.: US 6,472,185 B2
(45) Date of Patent: *Oct. 29, 2002

(54) USE OF SELECTIVE DNA FRAGMENT AMPLIFICATION PRODUCTS FOR HYBRIDIZATION-BASED GENETIC FINGERPRINTING, MARKER ASSISTED SELECTION, AND HIGH-THROUGHPUT SCREENING

(75) Inventors: Rhonda J. McCasky Feazel, Mt. Morris, IL (US); Timothy G. Helentjaris, Ankeny, IA (US); Sharon E. Malmberg, Dekalb; Barry A. Martin, Sycamore, both of IL (US)

(73) Assignee: Pioneer Hi-Bred International, Inc., Johnston, IA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/579,397

(22) Filed: May 25, 2000

(65) Prior Publication Data

US 2002/0098534 A1 Jul. 25, 2002

Related U.S. Application Data

(62) Division of application No. 09/005,205, filed on Jan. 9, 1998, now Pat. No. 6,100,030
(60) Provisional application No. 60/035,829, filed on Jan. 10, 1997.

(51) Int. Cl.[7] .............................. C12P 19/34; C12Q 1/68; C07H 21/02; C07H 21/04; C07H 19/00

(52) U.S. Cl. ..................... 435/91.2; 435/6; 435/91.1; 536/22.1; 536/23.1; 536/24.2; 536/24.3; 536/24.31; 536/24.33

(58) Field of Search ................... 435/6, 91.2; 536/23.1, 536/24.2, 24.3, 25.6

(56) References Cited

U.S. PATENT DOCUMENTS

| 4,851,330 A | 7/1989 | Kohne | 435/6 |
| 5,075,217 A | 12/1991 | Weber | 435/6 |
| 5,175,082 A | * 12/1992 | Jeffreys | 435/6 |

(List continued on next page.)

OTHER PUBLICATIONS

Penner GA, Lee SJ, Bezte LJ and Ugali E. Rapid RAPD screening of plant DNA using dot blot hybridization. Molecular Breeding, 2: 7–10, 1996.*

Bej et al., "Amplification of Nucleic Acids by Polymerase Chain Reaction (PCR) and other Methods and their Application", *Critical Reviews, in Biochemistry and Molecular Biology*, 26:3–4 301–334 (1991).

(List continued on next page.)

*Primary Examiner*—Jeffrey Siew
(74) *Attorney, Agent, or Firm*—David B. Ran; Jonathan Alan Quine; Quine Intellectual Property Law Group, P.C.

(57) ABSTRACT

Methods of genotyping amplified mixtures of DNAs, nucleic acid markers and methods of obtaining markers, kits, recombinant plants, positional cloning and integrated systems for making genotypes and assessing hybridizations are provided. These features are applicable to DNA fingerprinting, marker assisted selection, genotyping, cladistic analysis of variance, and high throughput laboratory screening methods.

20 Claims, 16 Drawing Sheets

U.S. PATENT DOCUMENTS

| | | | |
|---|---|---|---|
| 5,468,610 A | | 11/1995 | Polymeropoulos et al. |
| 5,582,989 A | * | 12/1996 | Caskey et al. ................. 435/6 |
| 5,610,287 A | | 3/1997 | Nikiforov et al. |
| 6,004,782 A | | 12/1999 | Ausubel et al. |
| 6,004,783 A | * | 12/1999 | Ausubel et al. ............ 435/91.2 |
| 6,045,994 A | * | 4/2000 | Zabeau et al. ................. 435/6 |

OTHER PUBLICATIONS

Penner et al., "Rapid RAPD screening of plant DNA using dot blot hybridization", *Molecular Breeding*, 2:1 7–10, see entire article (1996).

Austin et al., "Genetic resolution and verification of quantitative trait loci for flowering and plant height with recombinant inbred lines of maize[1]", *Genome* 39:5 957–968, see entire article (1996).

Howel et al. (1993) Europ. J. Immunogenet. 20:363–371.

Schlayer et al. (1992) 38:333–341.

Villard et al. (1996) Am. J. Genet. 58:1268–1278.

* cited by examiner

```
       c4                                    c5
        ┌─ PHP9574A                           ┌─ php09409
18.0 ─┤                          5.0 ─┤       ├─ bnl06.25
        ├─ e36m50/10328 ←
23.0 ─┤                         47.0 ─┤
        ├─ e36m50/9657 ←
12.0 ─┤ ├─ php09259
                                         ├─ UMC72
23.0 ─┤                         21.0 ─┤
 8.0 ─┤ ├─ JC0775A                       ├─ JC0748
 1.0 ─┤ ├─ JC0835A              23.0 ─┤
        └─ JC0807A               3.0 ─┤ ├─ JC1321AA
38.0 ─┤                          6.0 ─┤ ├─ JC0883B
                                 7.0 ─┤ ├─ php20872
                                         ├─ bnl05.02
        ├─ UMC66                25.0 ─┤
                                13.0 ─┤ ├─ JC0657A
57.0 ─┤                          6.0 ─┤ ├─ php20589
                                 7.0 ─┤ ├─ JC0219A
                                 7.0 ─┤ ├─ MALSB
                                10.0 ─┤ ├─ PHP9295A
 30  ─┤ ├─ JC1136A                       └─ php10014
        └─ UMC158
33.0 ─┤
        ├─ JC0317A              91.0 ─┤
 8.0 ─┤ └─ php10025

56.0 ─┤

├─ UMC68
        ├─ bnl15.07             22.0 ─┤
18.0 ─┤ ├─ JC0221A                       ├─ e35m48/9884 ←
15.0 ─┤ └─ JC0903A              14.0 ─┤ ├─ PHP9288A
                                 8.0 ─┤ └─ php20523
                                30.0 ─┤
       FIG. 9D.                          └─ php10017

FIG. 9E.
``` c6

- 4.0 — UMC159
- 9.0 — PHP9245A
- 12.0 — UMC85
- 9.0 — bnl06.29
- 9.0 — PHP9101A
- 14.0 — JC0210A
- — php20045A
- 39.0
- 9.0 — PHP9223A
- 13.0 — UMC113A
- 6.0 — "myb like" A
- 4.0 — UMC21
- 19.0 — JC0934A
- 7.0 — JC0760A
- 19.0 — bnl03.03
- 8.0 — bnl15.37
- 19.0 — UMC46
- 14.0 — bnl05.47
- — php10016
- 32.0
- — UMC132
- 41.0
- — UMC62
- 20.0 — php20599

- 14.0 — e35m50/9893 ←
- 14.0 — bnl15.40
- 12.0 — e33m56/10224 ←
- 14.0 — UMC98
- 22.0 — PHP9112A
- 29.0 — bnl15.21
- — php20708
- 4.0 — UMC110
- 9.0 — php20745
- 3.0 — UMC56
- 6.0 — JC0829
- 9.0 — e35m50/9899 ←
- 10.0 — php09283
- 13.0 — PHP9240A
- 6.0 — 2.0 — php8057A
- — 3.0 — bnl05.32
- 20.0 — UMC125
- 3.0 — 4.0 — bnl08.39
- 15.0 — JC0943A
- 10.0 — JC0878A
- 8.0 — e33m58/10494 ←
- 23.0 — UMC151A
- — bnl16.06
- 13.0 — bnl08.44
- 10.0 — UMC35
- 19.0 — php20020
- — php20728

- 10.0 — PHP9220A
- 24.0 — PHP9114A
- 6.0 — JC0190A
- 36.0 — bnl13.05A
- 2.0 — PHP9110A
- 18.0 — php10040
- 6.0 — UMC103
- 22.0 — PHP9585A
- 14.0 — UMC124A
- 17.0 — UMC120
- 28.0 — bnl09.08
- 22.0 — bnl02.369
- 7.0 — UMC12A
- 5.0 — UMC89
- 8.0 — JC0948
- 15.0 — e35m48/10160 ←
- 14.0 — JC0825A
- 13.0 — e33m50/9195 ←
- — JC0958A
- 50.0
- 10.0 — PHP9414A
- 12.0 — php20793
- 23.0 — UMC7
- 3.0 — Gst1
- — UMC3A

FIG. 9H.

USE OF SELECTIVE DNA FRAGMENT AMPLIFICATION PRODUCTS FOR HYBRIDIZATION-BASED GENETIC FINGERPRINTING, MARKER ASSISTED SELECTION, AND HIGH-THROUGHPUT SCREENING

CROSS-REFERENCE TO RELATED APPLICATIONS

This Application is a divisional of U.S. application Ser. No. 09/005,205 filed Jan. 9, 1998, now U.S. Pat. No. 6,100,030, issued Aug. 8, 2000 which is a Continuation-In-Part of U.S. application U.S. Ser. No. 60/035,829 Filed Jan. 10, 1997. U.S. Ser. No. 60/035,829 is incorporated herein by reference in its entirety for all purposes.

BACKGROUND OF THE INVENTION

Genetic markers represent (mark the location of) specific loci in the genome of a species or closely related species. A sampling of different genotypes at these marker loci reveals genetic variation. The genetic variation at marker loci can then be described and applied to marker assisted selection, genetic studies, commercial breeding, diagnostics, cladistic analysis of variance, genotyping of samples, forensic analysis and the like.

Genetic markers have the greatest utility when they are highly heritable, multi-allelic, and numerous. Most genetic markers are highly heritable because their alleles are determined by the nucleotide sequence of DNA, which is highly conserved from one generation to the next, and the detection of their alleles is unaffected by the natural environment. Markers have multiple alleles because, in the evolutionary process, rare, genetically-stable mutations in DNA sequences defining marker loci arose and were disseminated through the generations along with other existing alleles. The highly conserved nature of DNA combined with the rare occurrence of stable mutations allows genetic markers to be both predictable and discerning of different genotypes.

DNA fingerprinting is a broad term used to designate methods for assessing sequence differences in DNA isolated from various sources, e.g., by comparing the presence of marker DNA in samples of isolated DNA. Typically, DNA fingerprinting is used to analyze and compare DNA from different species of organisms or DNA from different individuals of the same species. DNA sequence differences detected by fingerprinting are referred to as DNA polymorphisms. The presence of a DNA polymorphism in an organism's DNA can serve to indicate that the genetic origin of such an organism is different from the genetic origin of organisms whose DNA does not have the polymorphism. Such polymorphisms can result, e.g., from insertion, deletion, and/or mutation events in the genome.

Many genetic-marker technologies are adaptable to fingerprinting, including restriction-fragment-length polymorphism (RFLP) Bostein et al (1980) *Am J Hum Genet* 32:314–331; single strand conformation polymorphism (SSCP) Fischer et al. (1983) *Proc Natl Acad Sci USA* 80:1579–1583, Orita et al. (1989) *Genomics* 5:874–879; amplified fragment-length polymorphism (AFLP) Vos et al. (1995) *Nucleic Acids Res* 23:4407–4414; microsatillite or single-sequence repeat (SSR) Weber JL and May PE (1989) *Am J Hum Genet* 44:388–396; rapid-amplified polymorphic DNA (RAPD) Williams et al (1990) *Nucleic Acids Res* 18:6531–6535; sequence tagged site (STS) Olson et al. (1989) *Science* 245:1434–1435; genetic-bit analysis (GBA) Nikiforov et al (1994) *Nucleic Acids Res* 22:4167–4175; allele-specific polymerase chain reaction (ASPCR) Gibbs et al. (1989) *Nucleic Acids Res* 17:2437–2448, Newton et al. (1989) *Nucleic Acids Res* 17:2503–2516; nick-translation PCR (e.g., TaqMan™) Lee et al. (1993) *Nucleic Acids Res* 21:3761–3766; and allele-specific hybridization (ASH) Wallace et al. (1979) *Nucleic Acids Res* 6:3543–3557, (Sheldon et al. (1993) *Clinical Chemistry* 39(4):718–719) among others. Kits for RAPD and AFLP analyses are commercially available, e.g., from Perkin Elmer Applied Biosystems (Foster City, Calif.). For example, the restriction fragment length polymorphism (RFLP) technique employs restriction enzyme digestion of DNA, followed by size separation of the digested DNA by gel electrophoresis, and hybridization of the size-separated DNA with a specific polynucleotide fragment. Differences in the size of the restriction fragments to which the polynucleotide probe binds reflect sequence differences in DNA samples, or DNA polymorphisms. See Tanksley, *Biotechnology* 7:257–264 (1988).

PCR-based fingerprinting methods result in the generation of a large number of reproducible DNA fragments of specific size that can be separated, typically by gel electrophoresis. These fragments are visualized to produce a "fingerprint" of the amplified DNA. Visualization of the size-separated fragments is effected either by direct visualization, e.g., with a fluorescent dye, by hybridization with a polynucleotide probe, or by labeling the amplification products during PCR (radioactively or flourescently) followed by detection of the labeled products in the gel. These fingerprints have a variety of uses: parentage analysis, linkage analysis of specific traits, analysis of the degree of generic relationship between individuals within a species and analysis of phylogenetic relationships between species. This has considerable commercial use in agriculture for marker assisted selection of genetic traits specific to particular genotypes (e.g., in crops or animals), identification and mapping of quantitative trait loci (QTLs) and the like.

A problem common to all DNA fingerprinting techniques in the prior art stems from the low throughput of the techniques. There exists a need to simplify and speed the DNA fingerprint analysis. The RFLP technique attempts to solve this problem by producing a limited number of DNA fragments by selective use of restriction enzymes, size separating DNA fragments using gel electrophoresis and employing specific polynucleotide probes to visualize a small number of DNA fragments at any one time. The RAPD and SSR techniques selectively amplify only one or a few fragments at a time and this small array of fragments is separated by gel electrophoresis and visualized. The AFLP technique also selectively amplifies certain restriction fragments, followed by size separation using acrylamide ,sequencing gels. DNA fragments are visualized by autoradiography or detection of fluorescence of labeled DNA molecules which were produced using labeled primers during the amplification procedure.

Each prior art fingerprinting technique is of limited usefulness because each fingerprint is generated by size separation using gel electrophoresis of each DNA sample analyzed. No meaningful data is generated without electrophoresis of the DNA samples to be analyzed. Both polyacrylamide and agarose gel electrophoresis are time consuming. Each DNA fingerprint using prior art methods requires running a gel, visualizing the DNA fragments on the gel, and analyzing the DNA fragment pattern. Thus, the number of DNA polymorphisms that can be analyzed at one time is limited by the time and cost of preparing and analyzing a gel electrophoresis fingerprint. Data density is limited by the resolution of the gels and capability of image analysis systems to reproducibly record the sizes of the separated fragments. In addition, the utility of existing methods is limited because the identity of each band amplified or hybridized is normally by size rather than sequence, making it difficult or impossible to precisely correlate bands on gels and alleles.

Therefore, it would be very useful to have a method for DNA fingerprinting that does not rely on gel electrophoresis for the generation of fingerprint information. Such a method would not require analysis of the complex data in a gel fingerprint and would allow the production of more DNA polymorphism data in less time and at a lower cost compared to levels currently achievable using prior art methods. In addition, a method which uses polynucleotide probes of known sequence has the advantage of being able to specifically associate DNA markers with alleles. This invention fulfills these and other needs.

SUMMARY OF THE INVENTION

The invention provides compositions, probes, methods of fingerprinting and genotyping, new marker assisted selection methods, methods of making probes, integrated systems for performing high-throughput assays, and other features which will be apparent upon reading this disclosure.

The fingerprinting methods herein do not rely on the rate-limiting step of gel electrophoresis for the generation of DNA fingerprints and can, therefore, produce a large number of DNA fingerprints in a short time. In one preferred embodiment, AFLP is used to identify differentially amplified nueleic acids, which are then converted into polynucleotide probes which map to polymorphisms. The differentially amplified AFLP DNAs are converted into polynucleotide probes by isolating individual polymorphic AFLP fragments from a mixture of fragments in an AFLP amplification product, followed by using these isolated fragments (dr clones or subclones thereof) as polynucleotide probes in hybridizations with immobilized DNA amplification mixtures (e.g., AFLP products). To generate a DNA fingerprint, a polynucleotide probe made according to the method of the invention is hybridized to a mixture of AFLP amplified DNA restriction fragments from DNA samples, generating a "positive" or "negative" hybridization result. Many unique DNA samples (typically in the thousands) can be analyzed together in a single hybridization. A series of hybridizations yields a unique fingerprint of each DNA sample in the analysis set of samples. This method is an improvement over the gel-based AFLP technique, which relies on gel electrophoresis for the production of every DNA fingerprint, significantly lowering the number of samples that can be analyzed easily. Gel-based AFLP techniques also suffer from the lack of a precise method for distinguishing AFLP fragments that have different sequences but have the same length. The hybridization-based assays of the invention can easily distinguish fragments with different sequences. Hybridization improves the genotyping capability of the AFLP technique in both sample throughput and specificity.

The techniques of the invention are adaptable to characterization of any biological nucleic acid (RNA, cDNA, genomic DNA, synthetic DNA or the like). In one aspect, a probe which hybridizes to a marker in linkage disequilibrium with a polymorphism is provided. The probe can be provided, e.g., by isolating, cloning, sub-cloning or synthesizing a nucleic acid corresponding to (the same as or hybridizing to) a marker such as a differentially amplified AFLP fragment. An exemplar probe is an oligonucleotide between about 8 and about 100 nucleotides in length corresponding to a polymorphic nucleotide marker nucleic acid. The probe is hybridized to a mixture of amplified biological DNA which includes a target nucleic acid which has the polymorphism as a subsequence. The amplified DNA can be amplified, e.g., by cloning, PCR, LCR, TAS, 3SR, NASBA, Qβ amplification or the like. The DNA is optionally heterogenous by either size or sequence, or both. Typically, the amplified DNA is genomic DNA (including cellular genomic DNA, and DNA from an organelle such as a mitochondria, chloroplast or the like), or cDNA. In a preferred assay format, the amplified DNA mixture or the probe is fixed to a solid support.

The invention further provides methods of mapping polymorphic genetic markers. In the methods, a mixture of restriction enzyme-digested nucleic acids from biological samples is provided. The mixture is amplified, thereby identifying a set of differentially amplified nucleic acids in the mixture, and at least one of the differentially amplified nucleic acids is mapped to a unique genetic polymorphism, thereby providing a marker for the polymorphism. Typically, more than one differentially amplified nucleic acid is mapped, thereby providing a set of markers. The set can be of any size, although more information is provided by larger sets. Typical set sizes are from about 1–100 markers, often 10–50 markers, generally about 10–30 markers. In one typical format, the method includes hybridizing a probe nucleic acid to a mixture of DNA amplified from a biological source of DNA comprising the polymorphism, thereby identifying the polymorphism in the biological source of DNA. In this format, the probe nucleic acid hybridizes under stringent conditions to a target nucleic acid comprising the polymorphism. This information is typically used to genotype a biological sample, e.g., for marker assisted selection.

In several embodiments, the invention comprises detection of target nucleic acids in an amplified mixture of DNA, by hybridizing a probe to the amplified mixture. Depending on the available equipment and intended application, many hybridization formats are desirable. For example, either the amplified mixture or the probe can be fixed to the solid support. Typically, the solid phase of the assay will be in an array format, with either selected probes or selected amplified mixtures being fixed to predetermined locations of the array, facilitating consideration of hybridization signal information. The assays may be performed in serial or in parallel formats, i.e., by simultaneously or serially measuring hybridization results of probe-amplification mixture hybridization. Many other variations will be apparent upon full review of this disclosure.

The invention also provides probes, compositions and methods of making probes. For example, the invention provides compositions having a marker nucleic acid which specifically hybridizes to a nucleotide polymorphism and an amplified mixture of DNA isolated from a biological source.

Probes used in the above assays can be made by providing first and second samples of amplified DNA, comparing the first and second samples of amplified DNA to identify differentially amplified DNAs, isolating the differentially amplified DNA, thereby providing isolated differentially amplified DNAs and genetically mapping the isolated differentially amplified DNA, thereby providing a genetically mapped isolated DNA, which hybridizes to a unique polymorphic nucleic acid. Typically, at least a portion of the genetically mapped isolated DNA is sequenced to identify associated polymorphisms. Oligonucleotides comprising a portion of the sequenced region are also provided. Preferred probes uniquely map to single sites in a haploid genomic DNA of a plant or animal, or to cDNA.

Any of the assays or compositions provided herein are optionally provided or practiced in kit form. Kits optionally have one or more component selected from the components consisting of a container, instructional materials, one or more control nucleic acids complementary to the markers, and recombinant cells comprising one or more target nucleic acids.

DEFINITIONS

Figure 1A:
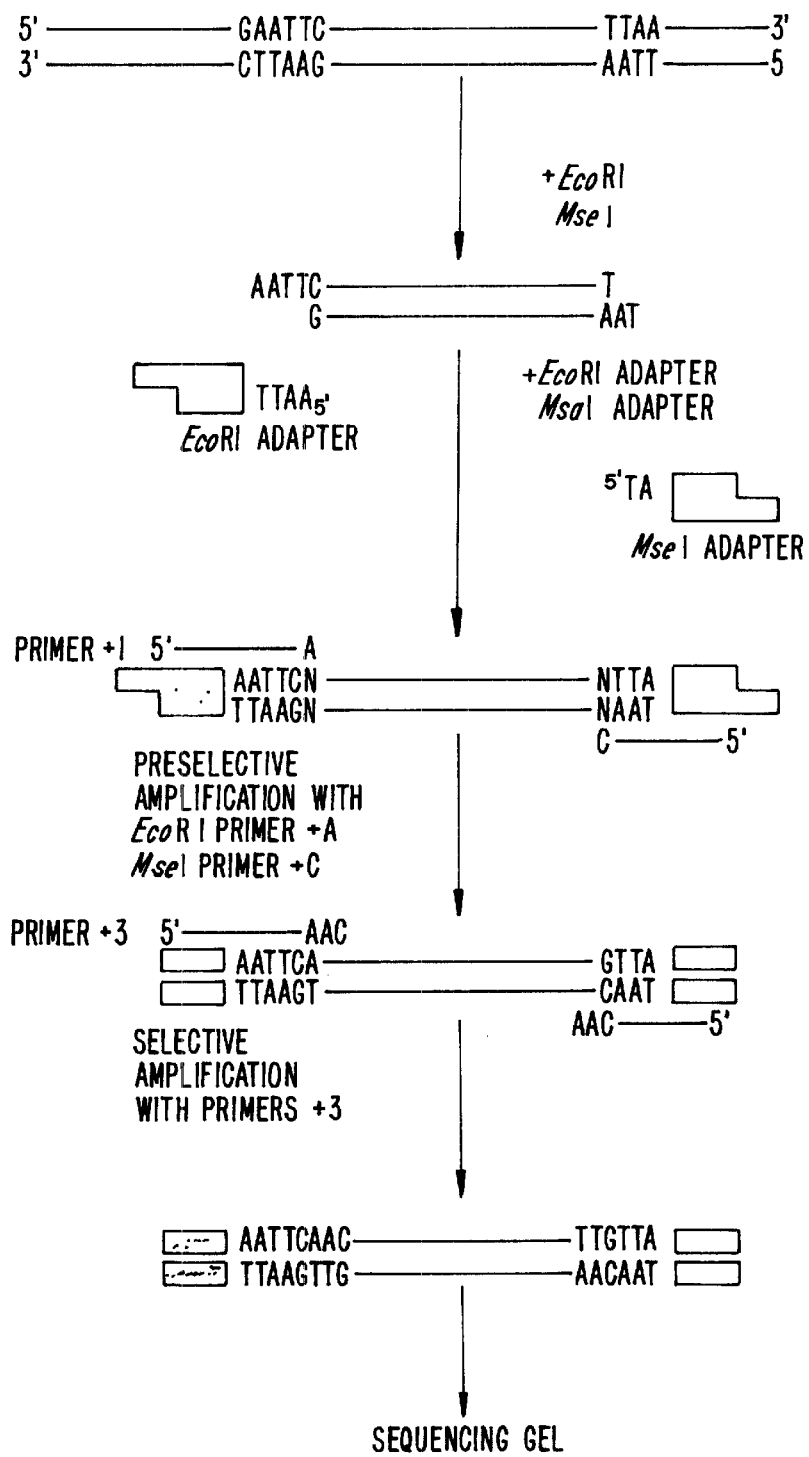
FIG. 1, Panels A and B describe the AFLP Technique using one primer pair. Step 1: restriction enzyme digestion; Step 2: ligation of adapters; Step 3: Plus 1 amplification; Step 4: Plus 3 amplification.

A "biological nucleic acid" is a nucleic acid (DNA, RNA, a combination thereof or an analogue thereof) which is isolated from a biological source or which is synthesized to have a nucleotide sequence which includes a region of sequence identity to a nucleic acid isolated from a biological source. Example biological nucleic acids are derived, e.g., from cDNA, genomic DNA isolated from a plant, genomic DNA isolated from a plant extract, genomic DNA isolated from an isolated plant tissue, genomic DNA isolated from an isolated plant tissue extract, genomic DNA isolated from a plant cell culture, genomic DNA isolated from a plant cell culture extract, genomic DNA isolated from a recombinant cell comprising a nucleic acid derived from a plant, genomic DNA isolated from a plant seed, genomic DNA isolated from an extract of a recombinant plant cell comprising a nucleic acid derived from a plant, genomic DNA isolated from an animal, genomic DNA isolated from an animal extract, genomic DNA isolated from an isolated animal tissue, genomic DNA isolated from an isolated animal tissue extract, genomic DNA isolated from an animal cell culture, genomic DNA isolated from an animal cell culture extract, genomic DNA isolated from a recombinant animal cell comprising a nucleic acid derived from an animal, genomic DNA isolated from an animal egg, genomic DNA isolated from an extract of a recombinant animal cell, DNA isolated from a mitochondria, and DNA isolated from a chloroplast.

A "biological source" is a sample of material isolated from a biological sample such as a plant, animal, isolated tissue or cell, or a portion of material made from such a source such as a cell extract, or the like. Typical biological sources of material include a plant, a plant extract, an isolated plant tissue, an isolated plant tissue extract, a plant cell culture, a plant cell culture extract, a recombinant cell comprising a nucleic acid derived from a plant, a plant seed, an extract of a recombinant plant cell comprising a nucleic acid derived from a plant, an animal, a animal extract, an isolated animal tissue, an isolated animal tissue extract, an animal cell culture, an animal cell culture extract, a recombinant animal cell comprising a nucleic acid derived from an animal, an animal egg, an extract of a recombinant animal cell, a DNA isolated from a mitochondria and a DNA isolated from a chloroplast.

A "polymorphism" is a change or difference between two related nucleic acids. A "nucleotide polymorphism" refers to a nucleotide which is different in one sequence when compared to a related sequence when the two nucleic acids are aligned for maximal correspondence. A "genetic nucleotide polymorphism" refers to a nucleotide which is different in one sequence when compared to a related sequence when the two nucleic acids are aligned for maximal correspondence, where the two nucleic acids are genetically related, i.e., homologous, e.g., where the nucleic acids are isolated from different strains of a soybean plant, or from different alleles of a single strain, or the like.

A "probe nucleic acid" is an RNA or DNA or analogue thereof. The probe may be of any length. Typical probes include PCR primers, PCR amplicons, cloned genomic nucleic acids encoding a genetic locus of interest, and the like.

A "genetic marker" is a region on a genomic nucleic acid mapped by a marker nucleic acid. A "marker nucleic acid" is a nucleic acid which is an indicator for the presence of a marker locus. The marker can be either a probe nucleic acid which identifies a target nucleic acid genetically linked to the locus, or a sequence hybridized by the probe, i.e., a genomic nucleic acid linked to the locus. Typically, a probe will be used to hybridize to or amplify the locus. Example markers include isolated nucleic acids from the locus, cloned nucleic acids comprising the locus, PCR primers for amplifying the locus, and the like.

"Marker assisted selection" refers to the process of selecting a desired trait or desired traits in a plant or plants by detecting one or more nucleic acids from the plant, where the nucleic acid is associated with the desired trait.

A "locus" is a nucleic acid region where a polymorphic nucleic acid resides.

Two nucleic acid sequences are "genetically linked" when the sequences are in linkage disequilibrium.

A "vector" is a composition which can transduce, transform or infect a cell, thereby causing the cell to express vector encoded nucleic acids and, optionally, proteins other than those native to the cell, or in a manner not native to the cell. A vector includes a nucleic acid (ordinarily RNA or DNA) to be expressed by the cell (a "vector nucleic acid"). A vector optionally includes materials to aid in achieving entry of the nucleic acid into the cell, such as a retroviral particle, liposome, protein coating or the like.

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active in a selected organism under most environmental and developmental conditions. An "inducible" promoter is a promoter which is under environmental or developmental regulation in a selected organism.

The terms "isolated" or "biologically pure" refer to material which is substantially or essentially free from components which normally accompany it as found in its native state.

An "amplified mixture" of nucleic acids includes multiple copies of more than one (and generally several) nucleic acids.

A "QTL" or "quantitative trait locus" include genes that control, to some degree, numerically representable phenotypic traits (disease resistance, crop yield, resistance to environmental extremes, etc.), that are distributed within a family of individuals as well as within a population of families of individuals. To measure QTLs, two inbred lines are typically crossed and multiple marker loci are genotyped, with one to several quantitative phenotypic traits among the progeny of the cross being evaluated. QTL are then identified and ultimately selected for based on significant statistical associations between the genotypic values determined by genetic marker technology and the phenotypic variability among the segregating progeny. Typical QTL include yield, grain moisture, grain oil, root lodging, stalk lodging, plant height, ear height, disease resistance, insect resistance, resistance to soybean cyst nematode, resistance to brown stem rot, resistance to phytopthora rot, and many others.

A "probe" is a composition labeled with a detectable label. A "probe" is typically used herein to identify a marker nucleic acid. A polynucleotide probe is usually a single-stranded nucleic acid that can be used to identify complementary nucleic acid sequences. The sequence of the polynucleotide probe may or may not be known. An RNA probe will hybridize with its corresponding DNA gene, or to a complementary RNA.

A "hybrid plant," as used in this specification, is a plant offspring produced by crossing two genetically dissimilar parent plants. An "inbred plant," as used in this specification, is a member of an inbred plant strain that has been highly inbred so that all members of the strain are genetically identical, with the exception of sexual differences.

In the assays of the invention, either the polynucleotide probe or the amplified sample can be ininobilized on a substrate prior to hybridization. Using different polynucleotide probes, one sample can be quickly and easily screened for the presence of many different polymorphisms generating a complex fingerprint based on the presence or absence of multiple polymorphisms. In addition, multiple samples can be screened for the presence of a particular marker. Thus, the present invention is a significant improvement over AFLP because it eliminates the need for gel electrophoresis of DNA fragments to produce a meaningful DNA fingerprint.

DETAILED DESCRIPTION OF THE PREFERRED EMBODIMENT

The present invention provides hybridization based DNA fingerprinting methods, compositions, integrated systems and other features. The invention overcomes problems with the traditional AFLP technique, which provides a pattern of DNA restriction fragments visualized on a polyacrylamide gel. The present invention is based, in part, on the discovery that DNA fragments which are amplifiable in a subset of samples (i.e., polymorphic DNA fragments), and which are identified, e.g., using the AFLP technique, can be isolated and used as polynucleotide probes in a hybridization-based fingerprint method, for example in dot blot or other solid phase hybridization methods.

To create a fingerprint according to the invention, a DNA sample of interest is amplified using the AFLP technique, or other techniques as discussed below. Then, rather than separating amplified DNA on a polyacrylamide gel to make a fingerprint according to the AFLP technique taught in the prior art, the entire amplified sample is simply tested for its ability to hybridize with an AFLP-generated polynucleotide probe, e.g., using a standard dot-blot assay. In general, 10 markers are adequate, and 20 or more are preferable, to develop a unique genetic fingerprint—although more than 10–20 markers can be used and less than 10 markers will be useful for analysis of certain polymorphisms. Determining the optimum number of markers needed for generation of a genetic fingerprint is a matter of routine optimization for the skilled artisan, and depends on the particular application.

Making and Using Markers for Detection of Polymorphic Nucleic Acids and Positional Cloning of Linked Nucleic Acids The ability to characterize an individual by its genome is due to the inherent variability of genetic information. Although DNA sequences which code for necessary proteins are well conserved across a species, there are regions of DNA which are non-coding or code for portions of proteins which do not have critical functions and therefore, absolute conservation of nucleic acid sequence is not strongly selected for. These variable regions are identified by genetic markers. Typically, genetic markers are bound by probes such as oligonucleotides or amplicons which specifically bind to unique variable regions of the genome. In some instances, the presence or absence of binding to a genetic marker identifies individuals by their unique nucleic acid sequence. In other instances, a marker binds to nucleic acid sequences of all individuals but the individual is identified by the position in the genome bound by a marker probe. The major causes of genetic variability are addition, deletion or point mutations, recombination and transposable elements within the genome of individuals in a plant population. In the present invention, polymorphisms which are represented by different sequences are most useful as markers, as different sequences are discriminated by a variety of restriction enzyme sequence recognition and hybridization procedures set forth herein.

Given the methods and compositions herein, one of skill can generate sets of marker nucleic acids and probe nucleic acids for detecting markers, including probes which are PCR primers, allele-specific probes, PCR amplicons (e.g., differentially amplified fragments in AFLP techniques) and the like, for the detection of polymorphic nucleotides at the loci disclosed herein, as well as genetically linked sequences. In particular, in a preferred embodiment, an AFLP reaction is used to identify differentially amplified nucleic acid bands on an acrylamide gel. These bands are isolated, and can be used as probes against amplified mixtures of DNA, such as DNA amplified from a relevant biological source (e.g., a plant or animal of interest). Commonly, it is desirable to clone the isolated DNA to produce superior probes, to determine the individual types of DNA present in the band and to map the individual types of DNA, to find those which map to unique loci. It will be appreciated that probe DNAs which do not map to unique loci have complicated inheritance patterns, making them less suitable for marker assisted selection or genotyping. Similarly, DNAs isolated from single bands may represent multiple individual types of DNA (the DNA in a band on an acrylamide gel can represent multiple different sequences with the same molecular weight), which also have complicated inheritance patterns. However, once a DNA is sequenced and mapped to a unique loci, it is suitable for marker assisted selection using any protocol which detects polymorphic variants of the sequence. Most of these are hybridization based.

Gel Electrophoresis

Techniques for gel electrophoresis of DNA, e.g., following an AFLP reaction, are well known in the art. See generally, CURRENT PROTOCOLS IN MOLECULAR BIOLOGY, pp. 2.5.1–2.5.17, 5.4.1–5.4.4, 7.0.3–7.0.11, 7.6.1–7.6.9, 15.8.3 and 15.8.4–15.8.5 (Ausubel, et al., eds. John Wiley & Sons, 1994). Both polyacrylamide and agarose gel electrophoresis can be used to separate the selectively amplified DNA restriction fragments. The composition of the gel is chosen based on the degree of resolution that is needed. Agarose can separate DNA strands that are 50–100 nucleotides different in size, unless special materials are used. Acrylamide can routinely separate molecules which differ by 1–2 bases: Following electrophoresis, the fragments can be visualized by a number of staining techniques known in the art. For example, silver staining can be used to visualize DNA on a polyacrylamide gel. See *BioTechniques* 17(5):915 (1994). In a preferred embodiment, 4.5% polyacrylamide gels are fixed in 10% ethanol/0.5% acetic acid for 5–10 minutes. Gels are then incubated in 10% ethanol/0.5% acetic acid/0.25% silver nitrate for 5–10 minutes. Gels are then rinsed twice with deionized water for less than one minute. Gels are developed in 3% sodium hydroxide/1% formaldehyde until bands appear (5–10 minutes). Following this, gels are incubated in a fixing solution (10% ethanol/0.5% acetic acid) for 5 minutes and washed in deionized water for 10 minutes.

Bands can also be visualized by using fluorescent dNTPs during the PCR reaction. To visualize the bands the gel can be continuously exposed to UV light. Additional information on fluorescent labeling techniques are described, supra. Another technique is labelling one of the PCR primers with T4 kinase and $P^{33}$ or $P^{32}$, exposing the gel to film, and marking the bands using pins which have been dipped in India ink prior to excision. This technique is useful when a single unique band is desired and high sensitivity is needed. It is, however, more tedious than silver staining for isolating all polymorphic DNA strands amplified with any given primer pair.

Each band visualized on the electrophoresis gel represents a population of DNA fragments of approximately the same size. In selecting DNA bands visualized on an electrophoresis gel that are unique to the population of interest (polymorphisms), visual comparison of AFLP DNA gel electrophoresis patterns is employed, using techniques known in the art. Polymorphisms useful as markers are selected on the basis of their visibility on the electrophoresis gel and their ability to reproducibly hybridize. Primer pairs are chosen for ability to amplify a large number of bands polymorphic between a heterogeneous set of inbreds and for amplification of few highly labelled monomorphic bands which can compete for nucleotides during the amplification process.

Band Isolation and Identification

Individual bands visualized on an electrophoresis gel are cut out of the gel, e.g., using a scalpel, and amplified, e.g., using PCR, LCR, cloning, or the like. Using PCR as an example, the DNA is amplified by placing the gel piece directly into a reaction vessel containing the PCR reagents and appropriate AFLP primers. Typically, a selective primer (e.g., a Plus 1 or Plus 3 primer) corresponding to that used in the AFLP technique to produce the DNA fragments which were electrophoresed is used as a primer for the PCR amplification of the DNA in the gel band. In a preferred embodiment, band amplification reactions contain the band cut out of the gel, plus 3 primer, deoxy nucleotide triphosphates (dNTPs), Hot Tub or Taq polymerase (Amersharm, Perkin Elmer or Boeinger Mannheim), and buffer. Bands are amplified using 5 cycles of 94° C.(30 s), 58° C.(30 s), and 72° C.(60 s); 5 cycles of 94° C.(30 s), and 94° C.(60s): and 20 cycles of 94° C.(30 s), 50° C.(30 s), and 72° C.(60 s).

Variations in the exemplar PCR technique used will be readily apparent to one skilled in the art and several variations are set forth herein. For example, different polymerase enzymes can be used and the reaction conditions can be varied to optimize amplification of DNA contained in the gel band. Additional information on PCR amplification are described supra. Similarly, one of skill will be able to clone isolated DNAs, or PCR amplified DNAs.

Amplification products are run on an agarose gel, e.g., preferably about a 1% agarose gel, to confirm successful amplification. If a band is seen, the products are optionally re-amplified e.g., using the modified primers for Ligation Independent Cloning (Pharmingen). To modify primers, a 13 bp DNA segment complementary to the ends of the pPMG-LIC vector is added to the Plus 1 primer according to the manufacture's instructions (Pharmigen). The product from the second amplification is checked on a 1% gel, and then purified using the Qiaquick PCR Purification Kit (Qiagen). The purified PCR products are then quantified e.g., by reading Hoechst dye (bis-Benzamide) fluorescence with a Dynatech MicroFLUOR Reader.

More generally, in vitro amplification techniques suitable for amplifying sequences for use as molecular probes (e.g., from isolated, amplified or cloned AFLP fragments, or naturally occurring sequences which map to unique loci) or generating nucleic acid fragments for subsequent subcloning are available. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039. One of skill will appreciate that essentially any RNA can be converted into a double stranded DNA suitable for restriction digestion, PCR expansion and sequencing using reverse transcriptase and a polymerase.

See, Ausbel, Sambrook and Berger, all supra. Further details on these procedures are found supra.

Any of these amplification techniques can also be used to generate amplified mixtures of DNA (i.e., from which AFLP bands are isolated, or against which probes are hybridized). For example, when PCR is used, random primer or linker-primer amplification strategies can be used, or, as in AFLP, oligonucleotides complementary to a PCR primer can be ligated to a DNA isolated from a cell. The PCR primer often has 1–5 additional arbitrary nucleotides at the 3' end of the primer which are not complementary to the ligated oligonucleotide, but which is complementary to more than one DNA isolated from the cell. Upon amplification, a mixture of DNAs are produced. Similarly, with LCR multiple or random primers can be used for the LCR reaction, resulting in multiple amplified products. Similarly, the other techniques discussed herein can be used to generate amplified mixtures using multiple or random primers which have sequence complementarity to more than one nucleic acid in DNA isolated from a cell. In cloning strategies, a cloned library of nucleic acids can be produced, amplified by expansion in an appropriate host culture and the DNA isolated from the culture.

Cloning Isolated AFLP Bands

Cloning methodologies for cloning DNAs from AFLP gel bands (or amplicons of such bands), and for replicating nucleic acids useful as probes, as well as sequencing methods to verify the sequence of cloned nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); and *Current Protocols in Molecular Biology*, F. M. Ausubel et al., eds., Current Protocols, a joint venture between Greene Publishing Associates, Inc. and John Wiley & Sons, Inc., (through and including the 1997 Supplement) (Ausubel). A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Lewin (1995) *Genes V* Oxford University Press Inc., N.Y. (Lewin); and Watson et al. (1992) *Recombinant DNA Second Edition Scientific American Books, N.Y.*

Most DNA sequencing today is carried out by chain termination methods of DNA sequencing. The most popular chain termination methods of DNA sequencing are variants of the dideoxynucleotide mediated chain termination method of Sanger. See, Sanger et al. (1977) *Proc. Nat. Acad. Sci., USA* 74:5463–5467. For a simple introduction to dideoxy sequencing, see, *Current Protocols in Molecular Biology*, F. M. Ausubel et al., eds., Current Protocols, a joint venture between Greene Publishing Associates, Inc. and John Wiley & Sons, Inc., (Supplement 37, current through 1997) (Ausubel), Chapter 7. Thousands of laboratories employ dideoxynucleotide chain termination techniques. Commercial kits containing the reagents most typically used for these methods of DNA sequencing are available and widely used.

In addition to the Sanger methods of chain termination, new PCR exonuclease digestion methods are available for DNA sequencing of PCR amplicons. Direct sequencing of PCR generated amplicons by selectively incorporating boronated nuclease resistant nucleotides into the amplicons during PCR and digestion of the amplicons with a nuclease to produce sized template fragments has been developed (Porter et al. (1997) *Nucleic Acids Research* 25(8): 1611–1617). In the methods, 4 PCR reactions on a template are performed, in which one of the nucleotide triphosphates in the PCR reaction mixture is partially substituted with a 2'deoxynucleoside 5'-α[P-borano]-triphosphate. The boronated nucleotide is stocastically incorporated into PCR products at varying positions along the PCR amplicon. An exonuclease which is blocked by incorporated boronated nucleotides is used to cleave the PCR amplicons. The cleaved amplicons are then separated by size using polyacrylamide gel electrophoresis, providing the sequence of the amplicon. An advantage of this method is that it requires fewer biochemical manipulations for sequencing a PCR amplicon than performing standard Sanger-style sequencing of PCR amplicons.

Product information from manufacturers of biological reagents and experimental equipment also provide information useful in known biological methods. Such manufacturers include the Sigma Chemical Company (Saint Louis, Mo.); New England Biolabs (Beverly, Mass.); R&D systems (Minneapolis, Minn.); Pharmacia LKB Biotechnology (Piscataway, N.J.); CLONTECII Laboratories, Inc. (Palo Alto, Calif.); ChemGenes Corp., (Waltham Mass.) Aldrich Chemical Company (Milwaukee, Wis.); Glen Research, Inc. (Sterling, Va.); GIBCO BRL Life Technologies, Inc. (Gaithersberg, Md.); Fluka Chemica-Biochemika Analytika (Fluka Chemie AG, Buchs, Switzerland); Invitrogen (San Diego, Calif.); Perkin Elmer (Foster City, Calif.); and Strategene; as well as many other commercial sources known to one of skill.

The nucleic acid compositions of this invention, whether DNA, RNA, cDNA, genomic DNA, or analogues thereof, or a hybrid of these molecules, are isolated from biological sources or synthesized in vitro. The nucleic acids of the invention are present in transfected whole cells, in transfected cell lysates, in transgenic plants (especially corn, canola, sunflower, wheat, soybean and sorghum), transgenic animals or in partially purified or substantially pure form.

In one preferred embodiment, The Pharmingen Ligation-Independent-Cloning kit is used for cloning. This publicly-available kit makes use of the pPMG-LIC vector and modified primers that create overhangs of sufficient length so that a ligation step is not necessary. The vector and insert anneal in a room temperature incubation to form the transformation vector. Alternatively, a TA cloning kit (Invitrogen) can also be used. The TA cloning kit does not utilize the modified Plus 1 primers. The TA Cloning Kit utilizes T4 DNA Ligase to add deoxyadenosine to the 3' ends of ds-cDNAs. This insert with A-overhangs are then ligated into the TA cloning vector with 3'T-overhangs. Variations in the PCR product cloning technique will be readily apparent to one skilled in the art.

In one class of embodiments, DH10B or other strains of *E. coli* which are compatible with pUC19 derived plasmids are transformed with a vector containing DNA from an amplified AFLP band and plated onto selective LB+ Carbenicillin agar plates. Using the Pharmigen LIC kit, only transformed bacteria propagate, and these colonies are re-streaked onto LB+ Carbenicillin plates. Plasmids are isolated from these clones using Promega Wizard Preps. Variations of plasmid isolation techniques using manufacturer's kits, modified phenol/chloroform/ethanol or isopropanol precipitation, or capture methods will be readily apparent to one skilled in the art.

Isolated plasmids, typically 100 ng, are labeled using the Amersham ECL Direct Nucleic Acid Labelling and Detection System. These labeled plasmids are used to probe previously prepared band amplification products prepared from the same DNA samples that were used to prepare the plasmid. If Plus 3 amplification products were prepared and used to make the DNA which was cloned into the plasmid, then Plus 3 amplification products of the same DNA sample are probed with the plasmid. A parallel procedure would be used for Plus 1 amplification products. Useful clones are those that recognize the same band from which they were originally isolated, using the dot blot hybridization described supra. Inserts from the clones can be sequenced. To determine which plasmids contain amplified DNA that will be useful as markers, the amplified DNA is labeled as described supra, and subjected to further evaluation as described supra. While this cloning step is not essential to the practice of the invention, it is the preferred method for preparing the hybridization probe if an oligonucleotide probe is not available.

In certain applications it is advantageous to make or clone large nucleic acids which encompass multiple loci, or to detect, clone or isolate nucleic acids linked to polymorphic nucleotides. For example, as described supra, in one embodiment positional cloning is used to isolate nucleic acids proximal to polymorphic nucleotides, optionally at more than one locus. These nucleic acids are in linkage disequilibrium with the polymorphic nucleotides, i.e., they are genetically linked to the polymorphic nucleotides on a chromosomal nucleic acid. It will be appreciated that a nucleic acid genetically linked to a polymorphic nucleotide optionally resides up to about 50 centimorgans from the polymorphic nucleic acid, although the precise physical distance will vary depending on the cross-over frequency of the particular chromosomal region. Typical distances from a polymorphic nucleotide are in the range of 1–50 centimorgans, for example, 0 (i.e., the probe hybridizes directly to the polymorphic nucleotide) less than 1, about 1–5, 1, 5, 10, 15, 20, 25, 30, 35, 40, 45 or 50 centimorgans, etc.

Many methods of making large recombinant RNA and DNA nucleic acids, including recombinant plasmids, recombinant lambda phage, cosmids, yeast artificial chromosomes (YACs), P1 artificial chromosomes, Bacterial Artificial Chromosomes (BACs), and the like are known. A general introduction to YACs, BACs, PACs and MACs as artificial chromosomes is described in Monaco and Larin (1994) *Trends Biotechnol* 12(7):280–286. Examples of appropriate cloning techniques for making large nucleic acids, and instructions sufficient to direct persons of skill through many cloning exercises are found in Berger and Kimmel, Sambrook, and Ausubel, all supra.

In one aspect, nucleic acids hybridizing to the polymorphic nucleic acids disclosed herein (or linked to such nucleic acids) are cloned into large nucleic acids such as YACs, or are detected in YAC genomic libraries cloned from soybean. The construction of YACs and YAC libraries is known. See, Berger, supra, and Burke et al. (1987) *Science* 236:806–812. Gridded libraries of YACs are described in Anand et al. (1989) *Nucleic Acids Res.* 17, 3425–3433, and Anand et al. (1990) *Nucleic Acids Res.* Riley (1990) 18:1951–1956 *Nucleic Acids Res.* 18(10):2887–2890 and the references therein describe cloning of YACs and related technologies. YAC libraries containing large fragments of soybean DNA have been constructed. See, Funke and Kolchinsky (1994) CRC Press, Boca Raton, Fla., pp. 125–308 1994; Marek and Shoemaker (1996) *Soybean Genet Newsl* 23:126–129 1996; Danish et al. (1997) *Soybean Genet Newsl* 24:196–198. See also, Ausubel, chapter 13 for a description of procedures for making YAC libraries.

Similarly, cosmids or other molecular vectors such as BAC and P1 constructs are also useful for isolating or cloning nucleic acids linked to polymorphic nucleic acids. Cosmid cloning is also known. See, e.g., Ausubel, chapter 1.10.11 (supplement 13) and the references therein. See also, Ish-Horowitz and Burke (1981) *Nucleic Acids Res.* 9:2989–2998; Murray (1983) Phage Lambda and Molecular Cloning in Lambda II (Hendrix et al., eds) 395–432 Cold Spring Harbor Laboratory, N.Y.; Frischauf et al. (1983) *J. Mol. Biol.* 170:827–842; and, Dunn and Blattner (1987) *Nucleic Acids Res.* 15:2677–2698, and the references cited therein. Construction of BAC and P1 libraries is known; see, e.g., Ashworth et al. (1995) *Anal Biochem* 224(2):564–571; Wang et al. (1994) *Genomics* 24(3):527–534; Kim et al. (1994) *Genomics* 22(2):336–9; Rouquier et al. (1994) *Anal Biochem* 217(2):205–9; Shizuya et al. (1992) *Proc Natl Acad Sci USA* 89(18):8794–7; Kim et al. (1994) *Genomics* 22(2):336–9; Woo et al. (1994) *Nucleic Acids Res* 22(23): 4922–31; Wang et al. (1995) *Plant* (3):525–33; Cai (1995) *Genomics* 29(2): 413–25; Schmitt et al. (1996) *Genomics* 1996 33(1):9–20; Kim et al. (1996) *Genomics* 34(2):213–8; Kim et al. (1996) *Proc Natl Acad Sci USA* (13):6297–301; Pusch et al. (1996) *Gene* 183(1–2):29–33; and, Wang et al. (1996) *Genome Res* 6(7): 612–9.

Improved methods of in vitro amplification to amplify large nucleic acids linked to the polymorphic nucleic acids herein are summarized in Cheng et al. (1994) *Nature* 369:684–685 and the references therein.

In addition, any of the cloning or amplification strategies described above are useful for creating contigs of overlapping clones, thereby providing overlapping nucleic acids which show the physical relationship at the molecular level for genetically linked nucleic acids. A common example of,this strategy is found in whole organism sequencing projects, in which overlapping clones are sequenced to provide the entire sequence of a chromosome. In this procedure, a library of the organism's cDNA or genomic DNA is made according to standard procedures described, e.g., in the references above. Individual clones are isolated and sequenced, and overlapping sequence information is ordered to provide the sequence of the organism. See also, Tomb et al. (1997) *Nature* 539–547 describing the whole genome random sequencing and assembly of the complete genomic sequence of *Helicobacter pylori*; Fleischmann et al. (1995) *Science* 269:496–512 describing whole genome random sequencing and assembly of the complete *Haemophilus influenzae* genome; Fraser et al. (1995) *Science* 270:397–403 describing whole genome random sequencing and assembly of the complete *Mycoplasma genitalium* genome and Bult et al. (1996) *Science* 273:1058–1073 describing whole genome random sequencing and assembly of the complete *Methanococcus jannaschii* genome. Recently, Hagiwara and Curtis (1996) *Nucleic Acids Research* 24(12):2460–2461 developed a "long distance sequencer" PCR protocol for generating overlapping nucleic acids from very large clones to facilitate sequencing, and methods of amplifying and tagging the overlapping nucleic acids into suitable sequencing templates. The methods can be used in conjunction with shotgun sequencing techniques to improve the efficiency of shotgun methods typically used in whole organism sequencing projects. As applied to the present invention, the techniques are useful for identifying and sequencing genomic nucleic acids genetically linked to the loci described.

It will be appreciated that essentially any subsequence of a large clone proximal to an identified polymorphism can be subcloned using standard techniques. See, Ausubel, Sambrook and Berger (all supra).

Hybridization Strategies

In a preferred aspect, a labeled probe nucleic acid is specifically hybridized to a marker nucleic acid from a biological sample and the label is detected, thereby determining that the marker nucleic acid is present in the sample. For example, a marker comprising a polymorphic nucleic acid can be detected by allele-specific hybridization of a probe to the region of the marker comprising the polymorphic nucleic acid. Similarly, a marker can be detected by Southern analysis, northern analysis, in situ analysis, or the like. Hybridization of probes to amplified mixtures of DNA (e.g., DNA amplified by AFLP techniques) is a preferred assay format. "Hybridization" is used here to denote the pairing of complementary nucleotide sequences to produce a DNA-DNA hybrid a DNA-RNA hybrid or an RNA-RNA hybrid. Complementary base sequences are those sequences that are related by the well-known base-pairing rules. In DNA, A pairs with T and C pairs with G. In RNA, U pairs with A, and C pairs with G.

Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. "Stringent hybridization conditions" in the context of nucleic acid hybridization are sequence dependent and are different under different environmental parameters. An extensive guide to the hybridization of nucleic acids is found in Tijssen (1993), id. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Highly stringent conditions are selected to be equal to the $T_m$ point for a particular probe. Sometimes the term "$T_d$" is used to define the temperature at which at least half of the probe dissociates from a perfectly matched target nucleic acid. In any case, a variety of estimation techniques for estimating the $T_m$ or $T_d$ are available, and generally described in Tijssen, id. Typically, G-C base pairs in a duplex are estimated to contribute about 3° C. to the $T_m$, while A-T base pairs are estimated to contribute about 2° C., up to a theoretical maximum of about 80–100° C. However, more sophisticated models of $T_M$ and $T_d$ are available and appropriate in which G-C stacking interactions, solvent effects, the desired assay temperature and the like are taken into account. For example, PCR primers can be designed to have a dissociation temperature ($T_d$) of approximately 60° C., using the formula: $T_d=(((((3 \times \#GC)+(2 \times \#AT)) \times 37)-562)/\#bp)-5$; where #GC, #AT, and #bp are the number of guanine-cytosine base pairs, the number of adenine-thymine base pairs, and the number of total base pairs, respectively, involved in the annealing of the primer to the template DNA.

An example of stringent hybridization conditions for hybridization of complementary nucleic acids that have more than 100 complementary residues on a filter in a Southern or northern blot is 50% formalin with 1 mg of heparin at 42° C., with the hybridization being carried out overnight. An example of stringent wash conditions for a Southern blot of such nucleic acids is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes.

In general, a signal to noise ratio of 2× (or higher). than that observed for an unrelated probe in the particular hybridization assay indicates detection of a specific hybridization. For highly specific hybridization strategies such as allele-specific hybridization, an allele-specific probe is usually hybridized to a marker nucleic acid (e.g., a genomic nucleic acid, an amplicon, or the like) comprising a polymorphic nucleotide under highly stringent conditions.

As applied, e.g., to an AFLP dot blot, to achieve meaningful results from hybridization between DNA immobilized on a membrane and a polynucleotide probe, (1) sufficient polynucleotide probe should bind to the immobilized DNA to produce a detectable signal (sensitivity) and (2) following the washing procedure, the probe should be attached only to those immobilized sequences with the desired degree of complementarity to the probe sequence (specificity).

One of skill in the art will recognize that various factors can influence the amount and detectability of the polynucleotide probe bound to the immobilized DNA. The specific activity of, the polynucleotide probe must be sufficiently high and sufficient target must be present to permit detection. Adding an inert polymer such as 10% (w/v) dextran sulfate (mol. wt. 500,000) or PEG 6000 to the hybridization solution can also increase the sensitivity of the hybridization. Adding these polymers has been known to increase the hybridization signal. See Ausubel, supra at p 2.10.10.

One of skill in the art will also recognize that various factors can be manipulated to optimize the specificity of the hybridization. Optimization of the stringency of the final washes to remove excess polynucleotide probe can serve to ensure that the desired degree of hybridization between the probe and the immobilized DNA is achieved.

The initial hybridization between the polynucleotide probe and the immobilized DNA is carried out under low stringency conditions that allow maximum binding of probe to the immobilized DNA. Typical stringency washes for the AFLP Dot Blot hybridizations using polynucleotide probes amplified from a band are carried out at a temperature of 42° C. in a solution containing 6M urea, 0.1×SSC, and 0.4% SDS, or at 60–65° C. if the urea is left out of the wash solution. When oligo probes are used in the AFLP Dot Blot hybridizations, lower stringencies are used to compensate for the lower $T_m$, of the probe. When using an oligo probe with a Tm between 55° C. and 60° C., the blots are prehybridized at 42° C. for 30–60 minutes in 0.75 M dibasic sodium phosphate/0.5 M monobasic sodium phosphate/1 mM disodium EDTA/1% sarkosyl. Blots are then hybridized at 42° C. in ACES hybridization solution (Life Technologies, Inc., Gaithersburg, Md.) containing the labeled oligo probe for one hour. Next, blots are subjected to two stringent 10 minute washes at 42° C. in 0.75 M dibasic sodium phosphate/0.5 M monobasic sodium phosphate/1 mM disodium EDTA/1% sarkosyl. Less stringent washing is useful when there is expected to be less similarity between the probe and the DNA sample to be analyzed, such as between members of a multigene family or between similar genes in a different organism.

Typically for detecting probes labeled with HRP, two room temperature washes, five minutes. each, in 2×SSC (pH 7) are performed on membranes after the stringent washes. Excess 2×SSC is blotted from the membranes and the blots are saturated with chemiluminescent HRP substrate (ECL substrate from Amersham) and two room temperature washes, five minutes each, in 1×ACES final wash buffer (Life Technologies, Inc., Gaithersburg, Md.) are performed after the stringent washes. Excess final wash buffer is blotted from membranes and the blots can be saturated with a chemiluminescent alkaline phosphate substrate (such as Lumiphos or CDP Star, Tropix) and exposed to x-ray film (Kodak, N.Y.) or a chemifluorescent substrate (Aftophos) and scanned on a fluorimager.

One preferred aspect of the present invention is that it results in high-throughput screening capabilities. For example, sets of markers are identified by isolating differentially amplified nucleic acids and cloning or subcloning (or generating oligonucleotides which correspond to a subsequence of the differentially amplified nucleic acid). In the assays below, from a few up to millions of different probes can be present in a single set. For example, using simple dot-blot hybridization methods, membranes with thousands of immobilized probes can be generated for screening against amplified DNAs. The solid-phase techniques described below can be adapted to having literally millions of different immobilized probes per square inch. Similarly, very large sets of amplified DNAs can be immobilized on membranes for simultaneous screening against one or more probes. Typical sets of probes will have from 2 to n probes, where n is an integer equal to or greater than one. For example, probe or amplification mixture sets of from about 2 to 5,000, commonly 50–4,000, often 100–1,000 members are typical for blot arrays. Probe sets of from about 2 to about 1,000,000, often 50–500,000, generally 100–100,000 are common in solid phase arrays. While very large sets of probes are possible, it will be appreciated that much smaller sets of less than 100 are also common in performing marker assisted selection. Indeed, probe sets of 10–20 probes corresponding to particular markers are often sufficient to identify a particular genetic strain.

Designing Oligonucleotide Probes for Hybridization

As those of skill in the art will recognize, the sequences of cloned AFLP bands can be compared to detect regions of homology between the various AFLP bands using a program like Sequencher, GCG, and the HGS Iris software. Any software which can align sequence and find regions of homology can be used, or the sequences can be compared manually. Regions containing unique sequences are useful for designing hybridization oligonucleotides ("oligos"). A program like OLIGO (Research Genetics) can be used for this purpose. The oligos will be designed to be approximately 15–25 bases in length and have a $T_m$ of approximately 55–60° C. The oligos typically have a label such as a modified 5' end so that either an alkaline phosphatase molecule or a horseradish peroxidase molecule can be attached (other labelling strategies are described, supra).

Oligonucleotides for use as probes, e.g., in in vitro amplification methods, or for use as marker probes, or the like, are typically synthesized chemically according to the solid phase phosphoramidite triester method described by Beaucage and Caruthers (1981), *Tetrahedron Letts.*, 22(20) :1859–1862, e.g., using an automated synthesizer, as described in Needham-VanDevanter et al. (1984) *Nucleic Acids Res.*, 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560. Custom oligos can also easily be ordered from a variety of commercial sources known to persons of skill.

Oligos labeled using different methods can be hybridized at the same time to the same dot/blot membrane. For example, the normalization oligo (labeled primer) and the probe oligo (complementary to the target sequence) may have different labels. Following the stringent washes, the detection of those probes with an HRP label would be done first, followed by detection of those oligos with an AP label. Simultaneous hybridizations can reduce the number of hybridizations required and eliminate sources of potential error by performing the hybridization of the normalization probes and the probes complementary to the target sequence at the same time, under the same conditions.

The AFLP Technique

As described supra, AFLP is used to generate both marker DNA probes and amplified mixtures to be detected by such marker probes. In the AFLP technique, Genomic DNA is digested with restriction endonucleases, e.g. Eco RI and Mse I (An AFLP kit using Eco RI and Mse I is available from PE Applied Biosystems, Foster City, Calif.). The ends of the restriction fragments are ligated to corresponding adaptors (e.g., Eco RI and Mse I adaptors). The adaptor-ligated restriction fragments are used as templates for PCR using primers comprising (1) a sequence complementary to the adaptor and (2) zero to typically about three selected arbitrary nucleotides on the 3' end. In this way, a set of unique DNA fragments is selectively amplified. DNA polymorphisms can be detected by separating and visualizing the amplified DNA fragments on a polyacrylamide gel. An AFLP fragment that is amplified in a subset of individuals of a species is a polymorphic marker. See also, PCT application WO 93/06239 (ZABEAU and VOS).

Any of the restriction endonucieases known in the art can be used to digest DNA for analysis using the AFLP technique (see, Sambrook, Ausubel and Berger, all supra). In one embodiment, the DNA subjected to AFLP is digested with a single restriction enzyme. In another embodiment, DNA is subjected to digestion with two or more different restriction enzymes. The number and type of restriction enzymes used will vary based on the DNA to be analyzed and the degree of complexity desired. When different restriction enzymes are used, a larger diversity of DNA fragments will be generated.

Some restriction enzymes generate flush ends in double-stranded DNA and some generate staggered ends. Adaptors, short double-stranded DNA sequences, must be tailored to the restriction enzyme used. For flush end DNA, an adaptor is flush at one end and for staggered ends, an adaptor is staggered at one end. Only one end of an adaptor is designed to be ligated to a restriction fragment. The adaptors attached to the ends of the digested DNA are generally made of two synthetic oligonucleotides, approximately 10 to 30 nucleotides long, which are in part complementary to each other and which form double-stranded complexes when mixed together. Ligase enzymes can be used to ligate the adaptors to the digested DNA, using standard ligation protocols.

The adaptors serve as templates for DNA primers. Primers are single strand DNA which serves as a template for the initiation of DNA synthesis by a DNA polymerase. The primers used in AFLP comprise (1) DNA complementary to the adaptor sequence, (2) DNA complementary to that portion of the digested DNA which is known based on the sequence-specific cleavage of restriction enzymes and (3) zero to three selected nucleotides. The primers are optionally designed to reduce the number and complexity of the fragments that are amplified using the PCR technique.

Figure 1B:
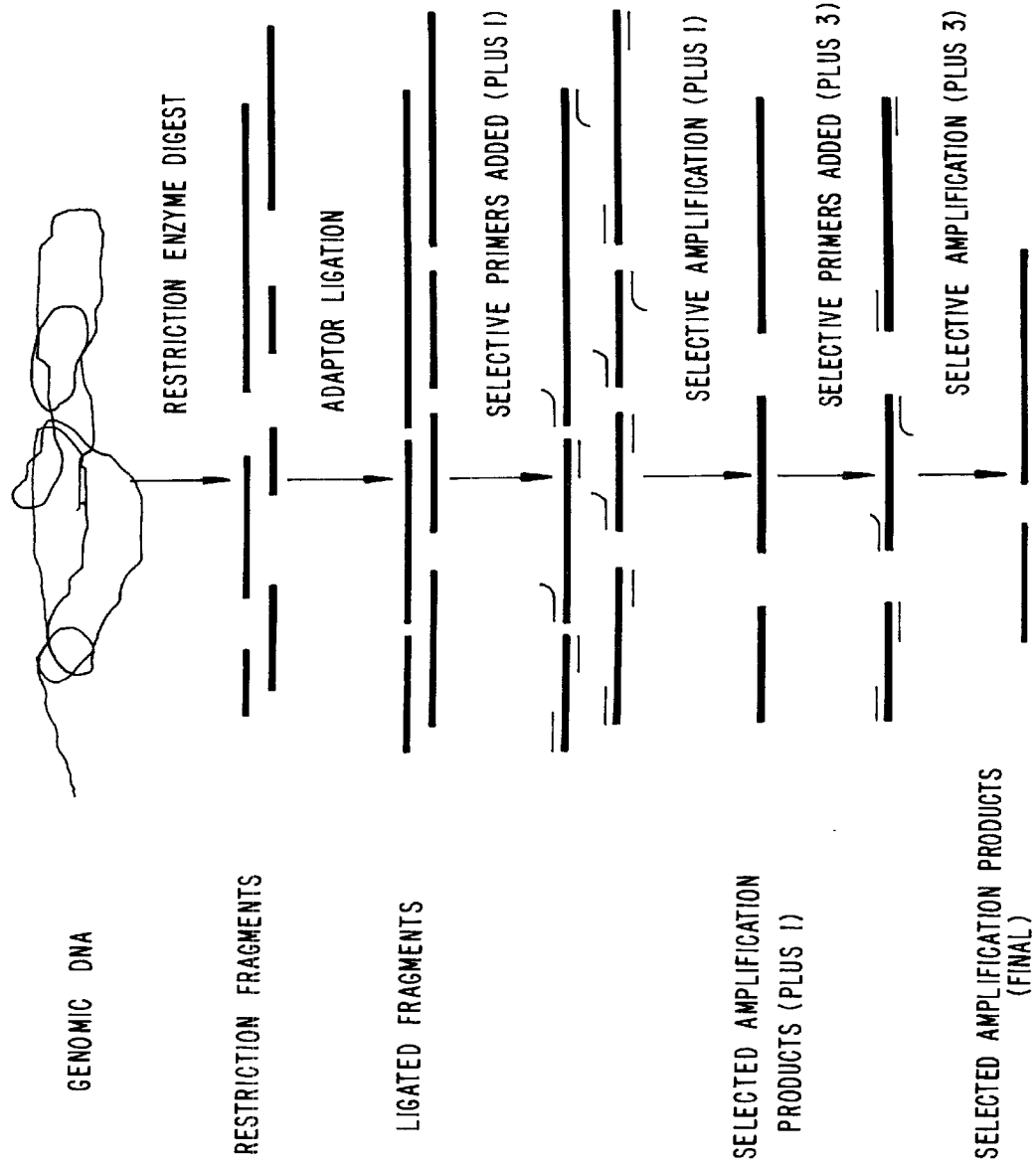
Figure 2:
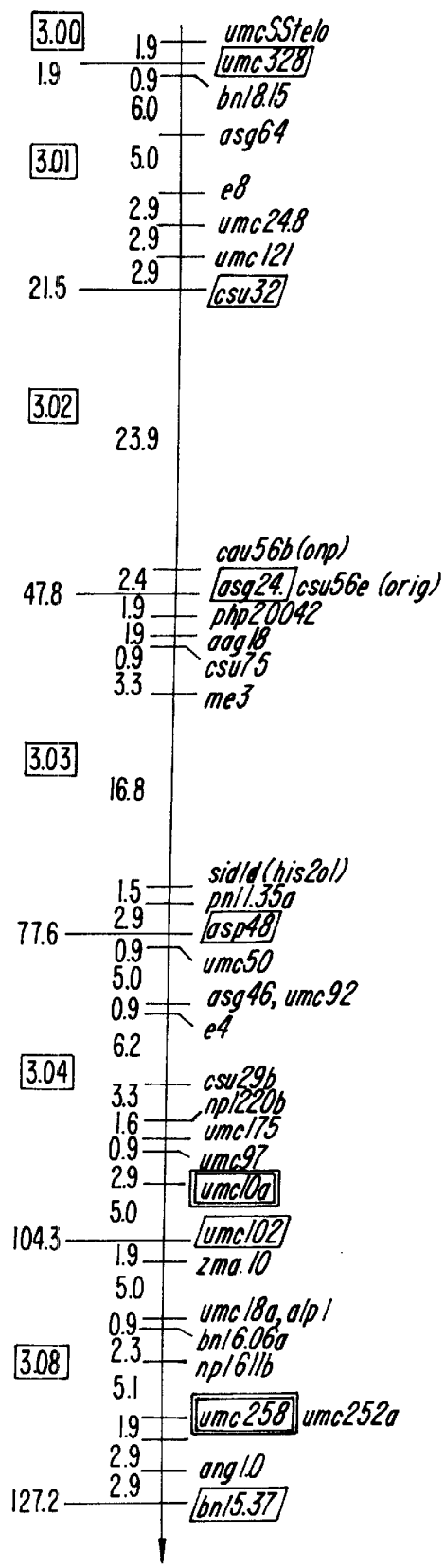
FIG. 2. The short arm of chromosome 3 in maize from a UMC (University of Missouri, Columbia) maize RFLP map printed in *Maize Genetic Cooperation Newsletter* 69:249 (1995). The RFLP markers that were linked to AFLP/Dot markers identified in the examples herein are marked by double boxes.

FIG. 1, panels A and B illustrates a typical AFLP run using one primer pair. Genomic DNA is digested with two restriction enzymes, such as Eco RI and Mse I (Step 1). Adaptors complementary to the restriction enzyme cleavage sites are ligated to the digested DNA (Step 2). Primers complementary to the adaptor/restriction enzyme target sequence (Plus 0 primers) or primers that are complementary to the adaptor sequence, the restriction enzyme target sequence in the genomic DNA, and contain one selected nucleotide at the 3' end of the primer (Plus 1 primers) are used to amplify DNA sequences between the restriction sites (Plus 0 products) or a subpopulation of DNA restriction fragments (Plus 1 products) (Step 3).

To increase selectivity of the amplification, an additional amplification can be done using primers that are identical to those used in first round of amplification, plus one or more additional selected nucleotides added to the 3' end (Plus 3 primers will have three selected bases added to the 3' end). (FIG. 1, Step 4). Thus the second round of amplification further reduces the complexity of the DNA fragments generated. The fragments can be separated by size using gel electrophoresis, discussed below.

It will be readily apparent to one of skill in the art that different combinations of primers and PCR amplification steps can be used, depending on the nature of the DNA to be analyzed. For example, the preselection step using Plus 0 primers may be omitted. For some applications, Plus 1 primer amplification will be all that is necessary to generate a sufficiently small number of DNA fragments. Determination of the particular restriction enzymes and primers to be used for a given DNA sample is a matter of routine experimentation and optimization for one of ordinary skill in the art.

Dot Blot Hybridization to Detect AFLP Polymorphisms

AFLP polymorphisms can be visualized by acrylamide gel electrophoresis. The method of the present invention involves using dot blot hybridizations in lieu of gel electrophoresis to visualize the AFLP polymorphisms, which provides advantages in cost, throughput and sensitivity. Dot blot hybridization is a method for evaluating the relative abundance and/or the presence or absence of a particular nucleic acid sequence (sometimes referred to as a "target" sequence) in a DNA sample. See CURRENT PROTOCOLS IN MOLECULAR BIOLOGY, pp. 2.9.15–2.10.16 (Ausubel, et al., eds. John Wiley & Sons, 1994). Briefly, identical amounts of fully denatured DNA or cDNA derived from RNA are spotted on a single membrane (nitrocellulose or nylon (charged or uncharged)) in dots of uniform diameter followed by hybridization with a polynucleotide probe to detect presence or absence of the target. The dot blots are produced, e.g., using pinner tools, vacuum dot/slot blotters, spin blotting from plates, or other variations that will be readily apparent to one skilled in the art. The denatured DNA or RNA is fixed (immobilized) on the membrane via a series of treatments (such as UV radiation, baking, and/or chemical treatment) well known in the art.

It is important that sufficient DNA be spotted onto the membrane to allow for detection of the target sequence when hybridizing with a polynucleotide probe. The concentration of the final AFLP amplification product is typically approximately 50 ng/ul. The amplification product is a mixture of many AFLP bands. An amount of 0.1 ul of the AFLP amplification product (~5 ng of a mixture of amplified bands) is pinned onto a membrane in each dot. This amount is generally adequate for detection of the target although one of skill in the art will appreciate that this amount may vary depending on the nature of the AFLP product and hybridization conditions used.

The relative properties of nylon and nitrocellulose membranes are well known in the art. Briefly, nylon membranes are stronger than nitrocellulose and can withstand ultraviolet radiation used to cross-link DNA to an uncharged membrane and can also withstand alkali treatment used to bind DNA to a charged membrane. Nylon membranes are preferred for most non-radioactive detection methods, and are also reusable, whereas nitrocellulose is not generally amenable to non-radioactive methods or reuse. See Ausubel, supra at 2.9.11–14 and 2.10.8–16.

The denaturation of the PCR amplification products can be accomplished by treating the products with a mixture of NaOH and EDTA. Schilling Yellow food coloring can be added to visualize the dots on the membrane so adjustments can be made based on the amount of AFLP product pinned in each dot (see section below on normalizing the data). Equal amounts of the mixture of NaOH/EDTA/Schilling Yellow food coloring is pipetted into plates that are compatible with the pinning tools. The plates are spun briefly to move all the liquid to the bottom of the wells. The liquid in the plates is allowed to evaporate (by heating briefly or allowing the liquid to evaporate at room temperature) leaving a dry pellet of NaOH/EDTA/Schilling Yellow food coloring. Typically the mixture is 0.67M NaOH, 0.017M EDTA, and 0.0033% Schilling Yellow food coloring, and 3 ul of the mixture is pipetted into each well of a 4×Genetix plate.

After the plates are prepared, the amplification products are pipetted from the amplification plates into the denaturation plates. Typically, 5 ul of amplification product is added to each well. The denaturation plate is then sealed, spun briefly to get all of the liquid into contact with the dry pellet, and stored at 4° C. temperature until the denatured amplification products are pinned onto a dry nylon membrane for hybridization.

Dot blots can also be made by dotting or pinning un-denatured amplification products onto a membrane that has been dampened using water or buffer, followed by treating with NaOH after dotting. The still damp membrane is placed DNA side up on blotting paper which has been previously saturated with 0.4M sodium hydroxide and 0.6 M sodium chloride, for 2 minutes. One of skill in the art will appreciate that pinning onto damp membranes is more difficult to automate, and detection capability is reduced if the membranes become dry prior to NaOH treatment.

Other variations on the dot blotting technique will be obvious to those skilled in the art. Membranes containing denatured DNA (from any method) are typically placed on blotting paper saturated with 0.5M Tris, pH 7.5 and 1.5M sodium chloride for 10–15 minutes to neutralize the membranes. The blots are then air-dried, UV-cross linked (200 J), and/or baked to adhere to the denatured DNA to the membrane. One of skill in the art will appreciate that a variety of methods can be used to neutralize and fix the DNA to the membranes.

The membrane is then incubated in a prehybridization solution containing reagents that block nonspecific DNA binding sites to reduce background hybridization. The prehybridization solution can be replaced with fresh solution containing a labelled nucleotide polynucleotide probe, or the labelled probe can be added to the solution used to prehybridize the membrane, followed by incubation to allow hybridization. This is usually followed by a series of stringent washes to ensure that probe only remains bound to those immobilized DNA sequences with a high degree of complementarity to the polynucleotide probe. The amount of polynucleotide probe bound to the sample DNA immobilized on the filter is used as an indicator of the presence and amount of a sequence complementary to the polynucleotide probe in the sample DNA. Creation of AFLP band polynucleotide probes, labelling, hybridization, and detection of these AFLP band polynucleotide probes are described in the following sections.

Figure 12:
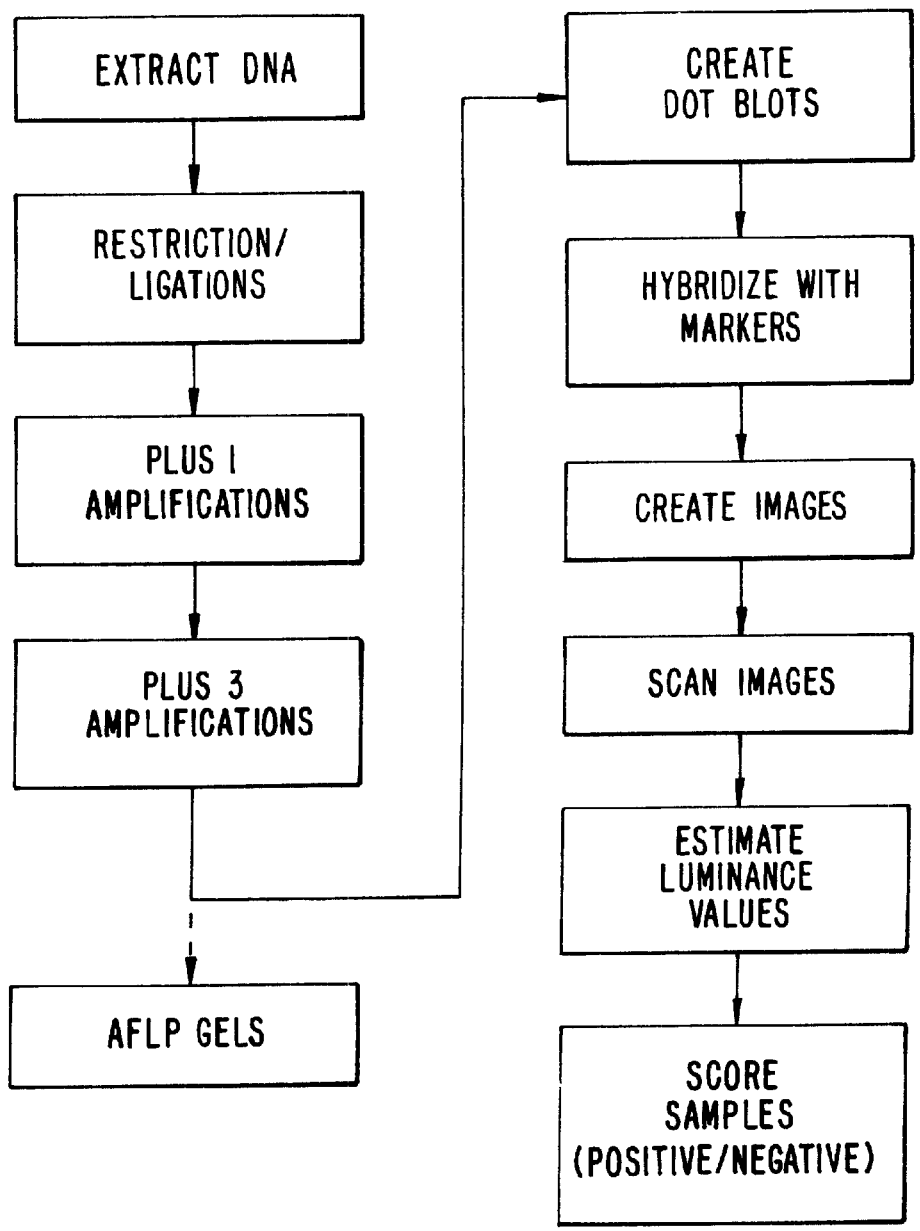
FIG. 12. A Dot Blot process Flow diagram.

Variations of this technique for immobilization of nucleic acid sequences will be readily apparent to those of skill in the art. For example, a polynucleotide probe prepared as described supra, can be immobilized on the membrane and a labeled DNA amplification product sample can be used as a polynucleotide probe to determine the presence of sequences complementary to the immobilized polynucleotide probe in the labeled DNA samples. Such a procedure may be useful when a relatively small number of samples are to be tested for the presence or absence of amplification of many AFLP bands. A Dot Blot process flow diagram is provided by FIG. 12.

Normalization of Dot Blot Assay

To normalize the dot blot intensity data to quantify the amount of amplified DNA present on each dot, the following procedures can be used. This process is helpful if there is variability in the amount of amplification product amplified in different samples, or in the amounts of liquid pinned or dotted onto the membranes. Polynucleotide probes made from monomorphic AFLP bands can be used to estimate the amount of amplification product present. Adjustments of the intensities of polymorphic polynucleotide probes can be made for each dot based on the ratio of the intensity from a monomorphic band for each dot to the average intensity of all dots for the monomorphic band.

To normalize the data based on the amount of amplification product pinned onto the membrane, the amount of dye (e.g., Schilling Yellow) present immediately after pinning can be used. The amount of dye present can be determined by scanning the pinned membranes to create a computer image of the membrane. The amount of color present in each dot can be determined by analyzing the image with a program designed to measure amount of color or darkness in the area of the dot. In one embodiment, an Optimas program is used (see, the examples below). Adjustments to the intensities of polymorphic polynucleotide probes are made for each dot based on the ratio of the dye intensity for each dot to the average dye intensity of all dots.

Allele-Specific Hybridization (ASH)

One preferred example of a hybridization technology for detecting marker nucleic acids is allele-specific hybridization, or "ASH." This technology is based on the stable annealing of a short, single-stranded oligonucleotide probe to a single-stranded target nucleic acid only when base pairing is completely complementary. The hybridization can then be detected from a radioactive or non-radioactive label on the probe (methods of labeling probes and other nucleic acids are set forth in detail below). As applied to the present invention, ASH is used to identify target nucleic acids in amplified mixtures of nucleic acids, made using any of the methods described herein.

ASH markers are polymorphic when their base composition at one or a few nucleotide positions in a segment of DNA is different among different genotypes. For each polymorphism, two or more different ASH probes are designed to have identical DNA sequences except at the polymorphic nucleotide(s). Each probe will have exact homology with one allele sequence so that the complement of probes can distinguish all the alternative allele sequences. Each probe is hybridized against the target DNA. With appropriate probe design and stringency conditions, a single-base mismatch between the probe and target DNA, will prevent hybridization and the unbound probe will wash away. In this manner, only, one of the alternative probes will hybridize to a target sample that is homozygous or homogeneous for an allele (an allele is defined by the DNA homology between the probe and target). Samples that are heterozygous or heterogeneous for two alleles will hybridize to both of two alternative probes. Having a probe for each allele allows the polymorphism to be genetically co-dominant which is useful in determining zygosity. In addition, a co-dominant ASH system is useful when hybridization does not occur for either one of two alternative probes, so that control experiments can be directed towards verifying insufficient target DNA or the occurrence of a new allele.

ASH markers are used as dominant markers where the presence or absence of only one allele is determined from hybridization or lack of hybridization by only one probe. The alternative allele may be inferred from the lack of hybridization. Heterogeneous target nucleic acids (i.e., chromosomal DNA from a multiallelic plant) are detected by monitoring simultaneous hybridization of two or more probes comprising different polymorphic nucleotides to a genomic nucleic acid.

Allele-specific hybridization was described by Wallace et al. (1979) *Nucleic Acids Res* 6:3543–3557, who showed that the hybridization between an oligonucleotide probe and bacteriophage target DNA dissociated at about 10° C. lower temperature when the probe and target sequences had a single base-pair mismatch compared to when the probe and target DNA had perfect homology. This difference in thermal stability allowed ASH probes to discriminate the two alleles determined by a single-nucleotide polymorphism between the wildtype sequence and a point mutation in the am-3 bacteriophage.

Later it was shown that a mixture of ASH probes, designed from the possible degenerate DNA sequences coding for a known amino acid sequence, could be used to identify clones containing the rabbit β-globin DNA that coded for that protein (Wallace et al. (1981) *Nuclei Acids Res* 9:879–894). They also showed that the only probe that hybridized to the clones had exact homology to the clone, whereas three probes that did not hybridize to the clones had a single base-pair mismatch with the target DNA.

ASH markers have been developed to diagnose susceptibility to human diseases caused by point mutations in DNA sequence. Examples are for the $\beta^s$-globin allele that can cause sickle-cell anemia (Conner et al. (1983) *Proc Natl Acad Sci USA* 80:278–282), the $\beta^0$-thalassemia allele that can cause β-thalassemia (Pirastu et al. (1983) *New England J Med* 309:284–287), the $\beta_1$-antitrypsin allele that can cause liver cirrhosis and pulmonary emphysema (Kidd (1983) *Nature* 304:230–234), the HLA-DR haplotypes associated with immune response (Angelini et al. (1986) *Proc Natl Acad Sci USA* 83:4489–4493), and the A985G allele that can cause medium-chain acyl-CoA dehydrogenase deficiency (Iitiä A et al. (1994) *BioTechniques* 17:566–571).

ASH markers have also been developed to identify strains of fungi resistant to the fungicide benzimidazole because of specific point mutations in the β-tubulin gene in *Venturia*

*inaequalis* (Koenraadt and Jones (1992) *Phytopathology* 82:1354–1358 and *Rhynchosporium secalis* (Wheeler et al. (1995) *Pestic Sci* 43:201–209).

An ASH probe is designed to form a stable duplex with a nucleic acid target only when base pairing is completely complementary. One or more base-pair mismatches between the probe and target prevents stable hybridization. This holds true for numerous variations of the process. The probe and target molecules are optionally either RNA or denatured DNA; the target molecule(s) is/are any length of nucleotides beyond the sequence that is complementary to the probe; the probe is designed to hybridize with either strand of a DNA target; the probe ranges in size to conform to variously stringent hybridization conditions, etc.

The polymerase chain reaction (PCR) (see, e.g., Mullis KB and Faloona F (1987) *Methods Enzymol* 155:335–350 and references supra) allows the target sequence for ASH to be amplified from low concentrations of nucleic acid in relatively small volumes (Koenraadt H and Jones AR (1992) *Phytopatholog* 82:1354–1358; Iitiä et al. (1994) *BioTechniques* 17:566–571). The target sequence from genomic DNA can also be digested with a restriction endonuclease and size separated by gel electrophoresis (Conner et al. 1983), although an advantage of the present method is that such electrophoretic separations are unnecessary. Hybridizations typically occur with the target sequence bound to the surface of a membrane or, as described in U.S. Pat. No. 5,468,613, the ASH probe sequence may be bound to a membrane. As described below, the ASH probe in some preferred embodiments is fixed to a solid substrate in an array.

Utilizing markers and amplified mixtures described here, ASH data can be obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography. Alternatively, the amplicons can be labelled, and the probes membrane bound. As discussed below, a variety of similar solid phase assays are also applicable.

Solid-Phase Arrays

In one variant, AFLP and ASH technologies are adapted to solid phase arrays for the rapid and specific detection of multiple polymorphic nucleotides. Typically, an ASH probe is linked to a solid support and a target nucleic acid (e.g., a genomic nucleic acid, an amplicon, or, most commonly, an amplified mixture) is hybridized to the probe. Either the probe, or the target, or both, can be labeled, typically with a fluorophore. Where the target is labeled, hybridization is detected by detecting bound fluorescence. Where the probe is labeled, hybridization is typically detected by quenching of the label. Where both the probe and the target are labeled, detection of hybridization is typically performed by monitoring a color shift resulting from proximity of the two bound labels. A variety of labeling strategies, labels, and the like, particularly for fluorescent based applications are described, supra.

In one embodiment, an array of probes are synthesized on a solid support. Exemplar solid supports include glass, plastics, polymers, metals, metalloids, ceramics, organics, etc. Using chip masking technologies and photoprotective chemistry it is possible to generate ordered arrays of nucleic acid probes. These arrays, which are known, e.g., as "DNA chips," or as very large scale immobilized polymer arrays ("VLSIPS™" arrays) can include millions of defined probe regions on a substrate having an area of about 1 $cm^2$ to several $cm^2$, thereby incorporating sets of from a few to millions of probes.

The construction and use of solid phase nucleic acid arrays to detect target nucleic acids is well described in the literature. See, Fodor et al. (1991) *Science*, 251: 767–777; Sheldon et al. (1993) *Clinical Chemistry* 39(4): 718–719; Kozal et al. (1996) *Nature Medicine* 2(7): 753–759 and Hubbell U.S. Pat. No. 5,571,639. See also, Pinkel et al. PCT/US95/16155 (WO 96/17958). In brief, a combinatorial strategy allows for the synthesis of arrays containing a large number of probes using a minimal number of synthetic steps. For instance, it is possible to synthesize and attach all possible DNA 8mer oligonucleotides ($4^8$, or 65,536 possible combinations) using only 32 chemical synthetic steps. In general, VLSIPS™ procedures provide a method of producing $4^n$ different oligonucleotide probes on an array uising only 4n synthetic steps.

Light-directed combinatorial synthesis of oligonucleotide arrays on a glass surface is performed with automated phosphoramidite chemistry and chip masking techniques similar to photoresist technologies in the computer chip industry. Typically, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents. Monitoring of hybridization of target nucleic acids to the array is typically performed with fluorescence microscopes or laser scanning microscopes.

In addition to being able to design, build and use probe arrays using available techniques, one of skill is also able to order custom-made arrays and array-reading devices from manufacturers specializing in array manufacture. For example, Affymetrix Corp., in Santa Clara, Calif. manufactures DNA VLSIP™ arrays.

It will be appreciated that probe design is influenced by the intended application. For example, where several allele-specific probe-target interactions are to be detected in a single assay, e.g., on a single DNA chip, it is desirable to have similar melting temperatures for all of the probes. Accordingly, the length of the probes are adjusted so that the melting temperatures for all of the probes on the array are closely similar (it will be appreciated that different lengths for different probes may be needed to achieve a particular $T_m$ where different probes have different GC contents). Although melting temperature is a primary consideration in probe design, other factors are optionally used to further adjust probe construction, such as selecting against primer self-complementarity and the like.

Chromosome Painting Technologies—In Situ Hybridization

In one aspect, a marker is used as a chromosome probe to cytogenetically detect the presence of a polymorphic nucleic acid or region linked to the nucleic acid. This can be especially useful because cytogenetic identification of a chromosomal region provides a way of determining the physical location of the region hybridized by the probe, i.e., in reference to other known markers.

Typically, a probe which hybridizes to a polymorphic nucleotide or a linked nucleic acid is chemically linked to a colorometric label, or fluorophore. The probe is used to paint the chromosome with the color label, thereby identifying regions which are hybridizes by the label. Chromosome painting refers to the staining of specific metaphase or prophase chromosomes or regions of chromosomes with probe mixtures, e.g., probes hybridizing to the polymorphic nucleic acids of the invention, and optionally, additional probes hybridizing to additional regions. The painting signal is preferably obtained by fluorescence in situ hybridization (FISH) of such mixtures with the target genome. A variety of staining technologies for the detection of chromosomal differences (typically abnormalities) are known. See, Jauch et al., *Hum. Genet.*, 85:145–150 (1990); Wier *Chromosomal*, 100:371–376 (1991); Van-den-Engh et al., *Cytometry* 6:92–100 (1988) and Kaltoft et al. *Arch. Dermatol. Res.*, 279:293–298 (1987); Sealey et al. *Nucleic Acids Res.* 13:1905 (1985); Landegent et al. *Hum. Genet.*, 77:366 (1987); Nisson et al., *BRL Focus*, 13:42 (1991).

Comparative genomic hybridization (CGH) is also a known approach for identifying the presence and localization of sequences in a genome compared to a reference genome. See, Kallioniemi, et al. (1992) *Science* 258:818. CGH can provide a quantitative estimate of copy number and also provides information regarding the localization of amplified or deleted sequences in a normal chromosome.

Many in situ detection techniques are known and can be adapted to the present invention. Fluorescent in situ hybridization (FISH), reverse chromosome painting, FISH on DAPI stained chromosomes, generation of Alphoid DNA probes for FISH using PCR, PRINS labeling of DNA, free chromatin mapping, spectral karyotyping and a variety of other techniques described, e.g., in Tijssen (1993) *Laboratory Techniques in biochemistry and molecular biology— hybridization with nucleic acid probes parts I and II*, Elsevier, New York, and, Choo (ed) (1994) Methods In Molecular Biology Volume 33- *In Situ Hybridization Protocols* Humana Press Inc., New Jersey (see also, other books in the Methods in Molecular Biology series).

These color-labeling strategies are useful for distinguishing the presence or absence of a chromosomal nucleic acid. They are also useful for the detection of multiple probes with multiple labels. In particular, chromosomes are optionally stained with multiple probes, optionally having multiple color labels. In this way, it is possible to quickly provide a genetic map of a sample at the molecular level. Furthermore, it is possible to determine whether two polymorphic nucleotides from the same locus are present. For example, if two allele-specific probes with different color labels are hybridized to a chromosomal sample under allele-specific hybridization conditions, it is possible specifically to detect both polymorphic nucleotides. For example, where a first probe has a "blue" label, and a second probe has a "yellow" label, a sample which is homozygous for the polymorphic nucleotide specifically bound by the first probe will look "blue" to an observer, a sample which is homozygous for the polymorphic nucleotide specifically bound by the second probe will look "yellow" to an observer, while a sample which is heterozygous and binds both probes will appear "green" to an observer. It will be appreciated that many color combinations are possible.

Amplification Detection Strategies

In a preferred embodiment, a polymorphic nucleotide is detected by amplifying the polymorphic nucleotide and detecting the resulting amplicon. A variety of variations on this strategy are used to detect polymorphic nucleic acids, depending on the materials available, and the like. In typical cases, a biological nucleic acid is amplified. Example biological nucleic acids are derived, e.g., from cDNA, genomic DNA isolated from a plant, genomic DNA isolated from a plant extract, genomic DNA isolated from an isolated plant tissue, genomic DNA isolated from an isolated plant tissue extract, genomic DNA isolated from a plant cell culture, genomic DNA isolated from a plant cell culture extract, genomic DNA isolated from a recombinant cell comprising a nucleic acid derived from a plant, genomic DNA isolated from a plant seed, genomic DNA isolated from an extract of a recombinant plant cell comprising a nucleic acid derived from a plant, genomic DNA isolated from an animal, genomic DNA isolated from an animal extract, genomic DNA isolated from an isolated animal tissue, genomic DNA isolated from an isolated animal tissue extract, genomic DNA isolated from an animal cell culture, genomic DNA isolated from an animal cell culture extract, genomic DNA isolated from a recombinant animal cell comprising a nucleic acid derived from an animal, genomic DNA isolated from an animal egg, genomic DNA isolated from an extract of a recombinant animal cell, DNA isolated from a mitochondria, DNA isolated from a chloroplast and any other biological source. Certain types of sources are preferred, depending on the application. For example, plant tissues or seeds are preferred for performing marker assisted selection of crops. Animal tissues are preferred for performing marker assisted selection of animals. In some applications, mitochondria (which may be maternally or paternally inherited, depending on the species) are preferred for cladistic analysis, or selection of QTLs which map to mitochondria. Chloroplast DNA is preferred where selection of a QTL which maps to the chloroplast is desired. Similar adaptations will be immediately apparent to one of skill upon review of this disclosure. Methods of isolating DNAs from cells, organelles, tissues, homogenates and the like are well known in the art, as are methods of making cDNAs from isolated RNAs or cloned libraries. See, Sambrook, Ausubel and Berger, supra.

In one embodiment, nucleic acid primers which hybridize to regions of a genomic nucleic acid that flank a polymorphic nucleotide to be detected are used in PCR LCR, or other amplification reactions to generate an amplicon comprising a polymorphic nucleotide to be detected. An example of this is the AFLP reaction used to generate amplification mixtures as described, supra. A variety of other PCR and LCR strategies are known in the art and are found in Berger, Sambrook, Ausubel, and Innis, all supra. See also, as Mullis et al., (1987) U.S. Pat. No. 4,683,202, U.S. Pat. No. 4,683,195, PCR TECHNOLOGY 1–31 (Henry A. Edich ed., Stockton Press 1989). In brief, a nucleic acid having a polymorphic nucleic acid to be detected (a genomic DNA, a genomic clone, a genomic amplicon a cDNA, or the like) is hybridized to primers which flank the polymorphic nucleotide to be detected (e.g., nucleotide polymorphisms). As discussed, amplification mixtures are also appropriate, in which several amplicons are simultaneously querried in a given assay. Detection is typically performed by hybridizing amplification reaction products to a selected probe, or to multiple probes as described supra. Alternatively, an acrylamide or agarose gel can be used to size separate reaction products (although this decreases throughput, and is therefore, often undesireable); the products can be detected by allele-specific hybridization, by allele-specific hybridization to a polymer array as described supra, or by sequencing the PCR amplicons (using standard Sanger dideoxy or Maxam-Gilbert methods). Amplicons are optionally cloned or sequenced by any of a variety of protocols as described supra for bands isolated from AFLP gels.

Once an amplicon is sequenced, the sequence is optionally used to select primers complementary to the amplicon, i.e., primers which will hybridize to the amplicon. It is expected that one of skill is thoroughly familiar with the theory and practice of nucleic acid hybridization and primer selection. Gait, ed. *Oligonucleotide Synthesis: A Practical Approach*, IRL Press, Oxford (1984); W. H. A. Kuijpers *Nucleic Acids Research* 18(17), 5197 (1994); K. L. Dueholm *J. Org. Chem.* 59, 5767–5773 (1994); S. Agrawal (ed.) *Methods in Molecular Biology*, volume 20; and Tijssen (1993) *Laboratory Techniques in biochemistry and molecular biology—hybridization with nucleic acid probes*, e.g., part I chapter 2 "overview of principles of hybridization and the strategy of nucleic acid probe assays", Elsevier, New York provide a basic guide to nucleic acid hybridization. Innis, supra, provides an overview of primer selection.

One of skill will recognize that the 3' end of an amplification primer is more important for PCR than the 5' end. Investigators have reported PCR products where only a few nucleotides at the 3' end of an amplification primer were complementary to a DNA to be amplified. In this regard, nucleotides at the 5' end of a primer can incorporate structural features unrelated to the target nucleic acid, such as complementarity to oligonucleotides ligated to a mixture of isolated DNA as in AFLP amplification. Similarly, sequencing primer hybridization sites (or a complement to such as primer, depending on the application) can be incorporated into the amplification primer, where the sequencing primer is derived from a primer used in a standard sequencing kit, such as one using a biotinylated or dye-labeled universal M13 or SP6 primer. One of skill will appreciate that constant regions in primer sequences are optional.

Primer sequences are optionally selected to hybridize only to a perfectly complementary DNA, with the nearest mismatch hybridization possibility from known DNA sequence typical having at least about 50 to 70% hybridization mismatches, and preferably 100% mismatches for the terminal 5 nucleotides at the 3' end of the primer.

PCR primers are optionally selected so that no secondary structure forms within the primer. Self-complementary primers have poor hybridization properties, because the complementary portions of the primers self hybridize (i.e., form hairpin structures). Primers are selected to have minimal cross-hybridization, thereby preventing competition between individual primers and a template nucleic acid and preventing duplex formation of the primers in solution, ,and possible concatenation of the primers during PCR. If there is more than one constant region in the primer, the constant regions of the primer are selected so that they do not self-hybridize or form hairpin structures.

One of skill will recognize that there are a variety of possible ways of performing the above selection steps, and that variations on the steps are appropriate. Most typically, selection steps are performed using simple computer programs to perform the selection as outlined above; however, all of the steps are optionally performed manually. One available computer program for primer selection is the MacVector™ program from Kodak. In addition to programs for primer selection, one of skill can easily design simple programs for any or all of the preferred selection steps.

One of skill will recognize that a wide variety of amplicons are provided by the present invention. In particular, amplicons are generated with primers flanking polymorphic nucleic acids which are identified by the methods herein. The amplicons can be generated by exponential amplification as described in the examples herein, or by linear amplification using a single specific primer, or by using one of the example primers below in conjunction with a set of random primers.

It will be appreciated that amplicons are characterized by a variety of physicochemical properties, including, but not limited to the following. First, the amplicons of the invention are produced in an amplification reaction using the primers as described above, with genomic or cDNA nucleic acid as a template (or a derivative thereof, such as a cloned or in vitro amplified genomic or cDNA nucleic acid). Second, single stranded forms of the amplicons (e.g., denatured amplicons) hybridize under stringent conditions to marker nucleic acids. Conditions for specific hybridization of nucleic acids, including amplicon nucleic acids are described above. A third physicochemical property of amplicons of the invention is that they specifically hybridize to one or more of the AFLP fragments identified using the methods herein.

In another embodiment, LCR is used to amplify a polymorphic nucleic acid or a mixture of polymorphic nucleic acids. By detecting the amplification product, presence of the polymorphic nucleotide is confirmed. Detection is typically performed by hybridizing LCR reaction products to a marker probe; alternatively, LCR products can be run on an acrylamide or agarose gel and the size of the reaction products detected (although this decreases throughput in some applictions, and is, therefore, often undesireable), or the products can be detected by allele-specific hybridization, by allele-specific hybridization to a polymer array as described supra, or by sequencing the LCR amplicons (using standard Sanger dideoxy or Maxam-Gilbert methods). Detection techniques such as PCR amplification or other in vitro amplification methods are also used to detect LCR products.

The ligation chain reaction (LCR; sometimes denoted the "ligation amplification reaction" or "LAR") and related techniques are used as diagnostic methods for detecting single nucleotide variations in target nucleic acids. LCR provides a mechanism for linear or exponential amplification of a target nucleic acid, or a mixture of DNAs comprising a target nucleic acid, via ligation of complementary oligonucleotides hybridized to a target. This. amplification is performed to distinguish target nucleic acids that differ by a single nucleotide, providing a powerful tool for the analysis of genetic variation in the present invention, i.e., for distinguishing polymorphic nucleotides.

The principle underlying LCR is straightforward: Oligonucleotides which are complementary to adjacent segments of a target nucleic acid are brought into proximity by hybridization to the target, and ligated using a ligase. To achieve linear amplification of the nucleic acid, a single pair of oligonucleotides which hybridize to adjoining areas of the target sequence are employed: the oligonucleotides are ligated, denatured from the template and the reaction is repeated. To achieve exponential amplification of the target nucleic acid two pairs of oligonucleotides (or more) are used, each pair hybridizing to complementary sequences on e.g., a double-stranded target polynucleotide. After ligation and denaturation, the target and each of the ligated oligonucleotide pairs serves as a template for hybridization of the complementary oligonucleotides to achieve ligation. The ligase enzyme used in performing LCR is typically thermostable, allowing for repeated denaturation of the template and ligated oligonucleotide complex by heating the ligation reaction. To amplify a mixture of nucleic acids, multiple primers are used (e.g., random primers, or primers comprising arbitrary nucleotides as described supra.

LCR is useful as a diagnostic tool in the detection of genetic variation. Using LCR methods, it is possible to distinguish between target polynucleotides which differ by a single nucleotide at the site of ligation. Ligation occurs only between oligonucleotides hybridized to a target polynucleotide where the complementarity between the oligonucleotides and the target is perfect, enabling differentiation between allelic variants of a gene or other chromosomal sequence. The specificity of ligation during LCR can be increased by substituting the more specific NAD+-dependant ligases such as E. coli ligase and (thermostable) Taq ligase for the less specific T4 DNA ligase. The use of NAD analogues in the ligation reaction further increases specificity of the ligation reaction. See, U.S. Pat. No. 5,508,179 to Wallace et al.

Finally, multiple LCR reactions can be run simultaneously in a single reaction, or in parallel reactions for simultaneous detection of any or all of the nucleotide polymorphisms described herein.

Nucleotide polymorphisms are also detected using other in vitro detection methods, including TAS, 3SR and Qβ amplification. (TAS), the self-sustained sequence replication system (3SR) and the Qβ replicase amplification system (QB), are reviewed in *The Journal Of NIH Research* (1991) 3, 81–94. The present invention may be practiced in conjunction with TAS (Kwoh, et al. (1989) *Proc. Natl. Acad. Sci. USA* 86, 1173 or the related 3SR (Guatelli et al. (1990) *Proc. Natl. Acad. Sci. USA* 87, 1874) for detecting single-base alterations in target nucleic acids by transcribing the target, annealing oligonucleotide primers to the transcript and ligating the annealed primers. QB replication (Lomell et al. (1989) *J. Clin. Chem* 35, 1826) may also be used in conjunction with the ligation methods of the present invention to detect mismatches by performing QB amplification on DNA ligated by the methods of the present invention.

Labeling and Detecting Probes

DNA from an AFLP band can be amplified and labeled in several ways. The DNA that is labeled can come from the following sources: 1) Amplification product using DNA from a gel piece as template, 2) Amplification product from an amplification where the template is a plasmid containing an AFLP band as an insert, 3) Plasmid DNA from a clone that contains an AFLP band as an insert, and 4) Oligonucleotide synthesis of subsequences of an AFLP band.

Several preferred methods can be used to label and detect the DNA from an AFLP band, including: 1) Chemiluminescence [using both Horseradish Peroxidase and/or Alkaline Phosphatase with substrates that produce photons as breakdown products] [kits available from Amersham, Boehringer-Mannheim, and Life Technologies/Gibco BRL], 2) Color production [using both Horseradish Peroxidase and/or Alkaline Phosphatase with substrates that produce a colored precipitate] [kits available from Life Technologies/Gibco BRL, and Boehringer-Mannheim], 3) Chemifluorescence using Alkaline Phosphatase and the substrate AttoPhos [Amersham] or other substrates that produce fluorescent products, 4) Fluorescence [using Cy-5 [Amersham], fluorescein, and other fluorescent tags], 5) Radioactivity using end-labeling, nick translation, random priming, or PCR to incorporate radioactive molecules into the probe DNA/oligonucleotide. Other methods for labeling and detection will be readily apparent to one skilled in the art.

Amplification products are preferably diluted 1/10, resulting in a concentration of approximately 10 ng DNA/ml. The oligo probes are diluted to a concentration of approximately 1.5 mM. The amount of these dilutions required to easily detect products is 1 ul of dilution for every 1 ml of hybridization solution used. Labeling methods such as the ECL Direct Nucleic Acid Labeling and Detection System (Amersham Corporation, 2636 Clearbrook Drive, Arlington Heights, Ill.), a horseradish peroxidase chemiluminescence system, can be used for labeling and detecting amplified bands. Methods of labeling oligonucleotides, such as the alkaline phosphatase (AP) system (E-Link kit Oligonucleotide Conjugation Kit from Genosys, Europe), can also be used.

More generally, a probe for use in an in situ detection procedure, an in vitro amplification procedure (PCR, LCR, NASBA, etc.), hybridization techniques (allele-specific hybridization, in situ analysis, Southern analysis, northern analysis, etc.) or any other detection procedure herein, including AFLP fragments, can be labeled with any composition detectable by spectroscopic, photochemical, biochemical, immunochemical, electrical, optical or chemical means. Useful labels in the present invention include spectral labels such as fluorescent dyes (e.g., fluorescein isothiocyanate, Texas red, rhodamine, dixogenin, biotin, and the like), radiolabels (e.g., $^3H$, $^{125}I$, $^{35}S$, $^{14}C$, $^{32}P$, $^{33}P$, etc.), enzymes (e.g., horse-radish peroxidase, alkaline phosphatase etc.) spectral colorimetric labels such as colloidal gold or colored glass or plastic (e.g. polystyrene, polypropylene, latex, etc.) beads. The label may be coupled directly or indirectly to a component of the detection assay (e.g., a probe, primer, isolated DNA, amplicon, YAC, BAC or the like) according to methods well known in the art. As indicated above, a wide variety of labels may be used, with the choice of label depending on sensitivity required, ease of conjugation with the compound, stability requirements, available instrumentation, and disposal provisions. In general, a detector which monitors a probe- target nucleic acid hybridization is adapted to the particular label which is used. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising a nucleic acid array with particular set of probes bound to the array is digitized for subsequent computer analysis.

Because incorporation of radiolabeled nucleotides into nucleic acids is straightforward, this detection represents a preferred labeling strategy. Exemplar technologies for incorporating radiolabels include end-labeling with a kinase or phoshpatase enzyme, nick translation, incorporation of radio-active nucleotides with a polymerase and many other well known strategies.

Fluorescent labels are also preferred labels, having the advantage of requiring fewer precautions in handling, and being amendable to high-throughput visualization techniques. Preferred labels are typically characterized by one or more of the following: high sensitivity, high stability, low background, low environmental sensitivity and high specificity in labeling. Fluorescent moieties, which are incorporated into the labels of the invention, are generally are known, including Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes and flavin. Individual fluorescent compounds which have functionalities for linking to an element desirably detected in an apparatus or assay of the invention, or which can be modified to incorporate such functionalities include, e.g., dansyl chloride; fluoresceins such as 3,6-dihydroxy-9-phenylxanthydrol; rhodamineisothiocyanate; N-phenyl 1-amino-8- sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl-N-methyl-2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine: N,N'-dihexyl oxacarbocyanine; merocyanine, 4-(3'-pyrenyl) stearate; d-3-aminodesoxy-equilenin; 12-(9'-anthroyl) stearate; 2-methylanthracene; 9-vinylanthracene; 2,2' (vinylene-p-phenylene)bisbenzoxazole; p-bis(2-(4-methyl-5-phenyl-oxazolyl))benzene; 6-dimethylamino-1,2-benzophenazin; retinol; bis(3'-aminopyridinium) 1,10-decandiyl diiodide; sulfonaphthylhydrazone of hellibrienin; chlorotetracycline; N-(7-dimethylamino-4-methyl-2-oxo-3-chromenyl)maleimide; N-(p-(2-benzimidazolyl)-phenyl) maleimide; N-(4-fluoranthyl)maleimide; bis(homovanillic acid); resazarin; 4-chloro-7-nitro-2,1,3-benzooxadiazole; merocyanine 540; resorufin; rose bengal; and 2,4-diphenyl-3(2H)-furanone. Many fluorescent tags are commercially available from SIGMA chemical company (Saint Louis, Mo.), Molecular Probes, R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica- Biochemika Analytika (Fluka Chemie AG, Buchs, Switzerland), and Applied Biosystems (Foster City, Calif.) as well as other commercial sources known to one of skill.

In one embodiment, nucleic acids are labeled by culturing recombinant cells which encode the nucleic acid in a medium which incorporates fluorescent or radio-active nucleotide analogues in the growth medium, resulting in the production of fluorescently labeled nucleic acids. Similarly, nucleic acids are synthesized in vitro using a primer and a DNA polymerase such as taq. For example, Hawkins et al. U.S. Pat. No. 5,525,711 describes pteridine nucleotide analogs for use in fluorescent DNA probes, including PCR amplicons.

The label is coupled directly or indirectly to a molecule to be detected (a product, substrate, enzyme, or the like) according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule (e.g., biotin) is covalently bound to a nucleic acid such as a probe, primer, amplicon, YAC, BAC or the like. The ligand then binds to an anti-ligand (e.g., strqptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody. Labels can also be conjugated directly to signal generating compounds, e.g., by conjugation with an enzyme or fluorophore or chromophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. Means of detecting labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems which are widely available.

Evaluation of DNA Fragments Isolated from AFLP Gel

Each DNA gel band that has been amplified and cloned is evaluated for its utility as a polynucleotide probe in a dot blot hybridization assay, or one of the other assays described herein. Two parameters are often evaluated: the ability of each potential probe to hybridize to (1) a set of fingerprinting inbred plants amplified with the appropriate Plus 3 primers, that result in a specific pattern of positives and negatives and (2) the amplified DNA from the gel band used to generate the polynucleotide probe. This hybridization can be evaluated using the dot blot hybridization procedure described in this specification. A testing membrane is created by separately amplifying DNA from the fingerprinting inbreds and making a hand dot blot with (1) the amplification products from a single primer pair and (2) the amplified DNA gel bands isolated from a single primer pair. (1) and (2) are immobilized onto a membrane. An amplified band that specifically recognizes itself (i.e., the band from which the probe was isolated or designed) and specifically hybridizes to the fingerprinting set of inbreds is considered useful as a polynucleotide probe for dot blots in the method of the invention. These bands are considered dominant markers. Bands that when hybridized to the testing membranes produce more positive inbreds than expected and recognize two or more band dots can be evaluated to determine if the additional positive bands belong to a co-dominant marker. Co-dominant markers are not useful in the method of the invention as polynucleotide probes for dot blot assays unless specific oligonucleotide sequences are designed for each allele.

Assessment of the Genetic Relationships: Marker Assisted Selection

Marker assisted selection refers to the process of selecting a desired trait or desired traits in a plant or plants by detecting one or more nucleic acids from the plant, where the nucleic acid is associated with the desired trait. The fingerprinting method of the invention can be used to assess the genetic relationship between plant varieties or individuals. A marker prepared in accordance with the methods of the invention can be used as a nucleotide sequence probe to analyze DNA from plant (or animal) varieties. The DNA to be analyzed is subjected to AFLP restriction enzyme digestion and amplification, using the same procedure as was used to generate the marker. The marker is used as a polynucleotide probe to determine the presence and abundance of the marker in the plant variety or individual. As those of skill in the art will recognize from the present disclosure, the fingerprint information accumulated is useful for germplasm security, quantitative trait loci studies, genetic relatedness studies, and generally for large scale genotyping and genomic analysis.

After genes or a QTL and a marker or markers identified by the present invention are mapped together and found to be in linkage disequilibrium, it is possible to use those markers to select for the desired alleles of those genes or QTL. In brief, a nucleic acid corresponding to the marker nucleic acid is detected in a biological sample from a plant or animal to be selected. This detection can take the form of hybridization of a probe nucleic acid to a marker, e.g., using AFLP-blot procedures, solid phase probe arrays, allele-specific hybridization, Southern analysis, northern analysis, in situ hybridization, hybridization of primers followed by PCR amplification of a region of the marker or the like. A variety of procedures for detecting markers are described herein. After the presence (or absence) of a particular marker in the biological sample is verified, the plant or animal is selected, i.e., used to make progeny plants by selective breeding.

Animal, and plant breeders ideally combine disease resistance loci with genes for high yield and other desirable traits to develop improved varieties of crops and animals. Classical strategies relying on phenotypic measurements for crop and animal husbandry, such as disease screening, for large numbers of samples can be very expensive, time consuming, and unreliable (due, e.g., to problems with lack of environemental control, polygenic effects and the like). Use of-the nucleotide polymorphisms identified by the methods herein and genetically linked nucleotides as genetic markers for disease resistance loci is an effective method of selecting desired varieties or traits in breeding programs. When a population is segregating for multiple loci affecting multiple diseases, the efficiency of MAS compared to phenotypic screening becomes even greater because all the loci can be processed in the lab together from a single sample of DNA. Another advantage over field evaluations for, e.g., disease reaction is that MAS can be done at any time of year regardless of the growing season. Moreover, environmental effects are irrelevant to marker assisted selection. Crops particularly well suited to marker assisted selection by the methods herein include corn, canola, soybean, wheat, sunflower, and sorghum.

Another use of MAS in plant and animal breeding is to assist the recovery of the recurrent parent genotype by backcross breeding. Backcross breeding is the process of crossing a progeny back to one of its parents. Backcrossing is usually done for the purpose of introgressing one or a few loci from a donor parent into an otherwise desirable genetic background from the recurrent parent. The more cycles of backcrossing that is done, the greater the genetic contribution of the recurrent parent to the resulting variety. This is often necessary, because resistant plants or animals may be otherwise undesirable, i.e., due to low yield, low fecundity, or the like. In contrast, strains which are the result of intensive breeding programs may have excellent yield, fecundity or the like, merely being deficient in one desired trait such as resistance to a particular pathogen (this process of repeated backcrossing to move a QTL into a selected background is referred to as "introgression" of the QTL into the backcross strain).

The loci identified herein are optimally distributed around the genome of the organism of interest, and are used to select for the recurrent-parent genotype. MAS for the recurrent-parent genotype can be combined with MAS for the disease resistance loci using these markers. Accordingly, it is possible to use the markers to introduce disease resistance QTL into plant or animal varieties having an otherwise desirable genetic background using the markers of the invention for selection of the QTL and for selection of the otherwise desirable background.

In one desirable embodiment, high-throughput methods of selecting polymorphic variants by marker assisted selection are provided. In the methods, a mixture of nucleic acids amplified from a biological source is provided. The mixture optionally includes an amplified first target nucleic acid which hybridizes to a first marker nucleic acid which hybridizes to a first locus comprising a first nucleotide polymorphism. In this regard, it will be appreciated that an assay showing that a particular polymorphic variant is not present in a sample can be used to identify a sample or to select against an unwanted variant in the same way that an assay can be used to select for the presence of a desired polymorphic variant. In the assay, therefore, the biological source is selected for the presence or absence of the first target nucleic acid in the mixture of amplified nucleic acids, with the presence or absence being measured by hybridization of the marker nucleic acid to the amplified mixture. Similarly, the presence or absence of additional target nucleic acids (e.g., 2, 3, 4, 5 . . . n where n is an integer) corresponding to the same or additional loci in the mixture are detected by the same, or by additional probes. About 4,000 separate biological sources and/or targets have been assayed in a single high-throughput dot blot assay using the dot-blot methods described herein, in a single experiment.

Generic markers covering the entire genome with at least a ten-fold increase in throughput over any gel-based genetic marker technique are provided by the methods of marker identification described herein. If an AFLP-based marker is tightly linked to a trait, then that marker is useful for marker assisted selection among thousands of individuals using this invention. It is an object of the invention to provide improved methods of segregation analysis, improved methods for assessing genetic relationships between inbred and hybrid plants and improved methods for assessing genetic relationships between plant varieties and individuals.

Making Transgenic Plants With Nucleic Acids Linked to Selected Loci

Nucleic acids which are genetically linked to the loci mapped by markers corresponding to differentially amplified nucleic acids identified by AFLP are optionally cloned and transduced into cells, especially to make probes or transgenic plants or animals. The cloned sequences are useful as molecular tags for selected plant strains, and are further useful for encoding polypeptides. Often, these polypeptides are encoded by a QTL which maps near the marker and are responsible, in while or in part, for the phenotypic effects of the QTL.

Nucleic acids linked to a selected locus or selected loci are introduced into plant cells, either in culture or in organs of a plant, e.g., leaves, stems, fruit, seed, etc. The expression of natural or synthetic nucleic acids encoded by nucleic acids linked to polymorphic nucleic acids can be achieved by operably linking a nucleic acid of interest to a promoter, incorporating the construct into an expression vector, and introducing the vector into a suitable host cell. Alternatively, an endogenous promoter linked to the nucleic acids can be used. Similarly, nucleic acids are intorduced into animal egg cells using known mehtods.

Typical vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Giliman & Smith, *Gene* 8:81 (1979); Roberts, et al., *Nature*, 328:731 (1987); Schneider, B., et al., *Protein Expr. Purif.* 6435:10 (1995); Berger, Sambrook, Ausubel (all supra).

Cloning of Sequences into Bacterial Hosts

There are several well-known methods of introducing nucleic acids into bacterial cells, any of which may be used in the present invention. These include: fusion of the recipient cells with bacterial protoplasts containing the DNA, electroporation, projectile bombardment, and infection with viral vectors, etc. Bacterial cells are often used to amplify increase the number of plasmids containing DNA constructs of this invention. The bacteria are grown to log phase and the plasmids within the bacteria can be isolated by a variety of methods known in the art (see, for instance, Sambrook). In addition, a plethora of kits are commercially available for the purification of plasmids from bacteria. For their proper use, follow the manufacturer's instructions (see, for example, EasyPrep™, FlexiPrep™, both from Pharmacia Biotech; StrataClean™, from Stratagene; and, QIAexpress Expression System, Qiagen). The isolated and purified plasmids are then further manipulated to produce other plasmids, used to transfect plant cells or incorporated into *Agrobacterium tumefaciens* to infect plants.

The in vitro delivery of nucleic acids into bacterial hosts can be to any cell grown in culture. Contact between the cells, and the genetically engineered nucleic acid constructs, when carried out in vitro, takes place in a biologically compatible medium. The concentration of nucleic acid varies widely depending on the particular application, but is generally between about 1 $\mu$M and about 10 mM. Treatment of the cells with the nucleic acid is generally carried out at physiological temperatures (about 37° C.) for periods of time of from about 1 to 48 hours.

Alternatively, a nucleic acid operably linked to a promoter to form a fusion gene is expressed in bacteria such as *E. coli* and its gene product isolated and purified.

Transfecting Plant Cells

To use isolated sequences in the above techniques, recombinant DNA vectors suitable for transformation of plant cells are prepared. Techniques for transforming a wide variety of higher plant species are well known and described in the technical and scientific literature. See, for example, Weising, et al., *Ann. Rev. Genet.* 22:421–477 (1988). A DNA sequence coding for the desired mRNA, polypeptide, or non-expressed tagging sequence is transduced into the plant. Where the sequence is expressed, the sequence is optionally combined with transcriptional and translational initiation regulatory sequences which will direct the transcription of the sequence from the gene in the intended tissues of the transformed plant.

Promoters in nucleic acids linked to the above loci are identified, e.g., by analyzing the 5' sequences upstream of a coding sequence in linkage disequilibrium with a loci mapped by a marker identified herein. Optionally, such nucleic acids will be associated with a QTL. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of a transcription start site. In most instances the TATA box aids in accurate transcription initiation. In plants, further upstream from the TATA box, at positions −80 to −100, there is typically a promoter element with a series of adenines surrounding the trinucleotide G (or T) N G. See, e.g., J. Messing, et al., in GENETIC ENGINEERING IN PLANTS, pp. 221–227 (Kosage, Meredith and Hollaender, eds. (1983)). A number of methods are known to those of skill in the art for identifying and characterizing promoter regions in plant genomic DNA. See, e.g., Jordano, et al., *Plant Cell* 1:855–866 (1989); Bustos, et al., *Plant Cell* 1:839–854 (1989);, Green, et al., *EMBO J.* 7:4035–4044 (1988); Meier, et al., *Plant Cell* 3:309–316 (1991); and Zhang, et al., *Plant Physiology* 110:1069–1079 (1996).

In construction of recombinant expression cassettes of the invention, a plant promoter fragment is optionally employed which directs expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers.

If polypeptide expression is desired, a polyadenylation region at the 3'-end of the coding region is typically included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker can encode biocide resistance, particularly antibiotic resistance, such as resistance to kanamycin, G418, bleomycin, hygromycin, or herbicide resistance, such as resistance to chlorosluforon or Basta.

Introduction of Nucleic Acids into Plant Cells

The DNA constructs of the invention are introduced into plant cells, either in culture or in the organs of a plant by a variety of conventional techniques. For example, the DNA construct can be introduced directly into the genomic DNA of the plant cell using techniques such as electroporation and microinjection of plant cell protoplasts, or the DNA constructs can be introduced directly to plant cells using ballistic methods, such as DNA particle bombardment. Alternatively, the DNA constructs are combined with suitable T-DNA flanking regions and introduced into a conventional *Agrobacterium tumefaciens* host vector. The virulence functions of the *Agrobacterium tumefaciens* host directs the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski, et al., *EMBO J.*

3:2717 (1984). Electroporation techniques are described in Fromm, et al., *Proc. Nat'l. Acad. Sci. USA* 82:5824 (1985). Ballistic transformation techniques are described in Klein, et al., *Nature* 327:70–73 (1987).

*Agrobacterium tumefaciens*-mediated transformation techniques, including disarming and use of binary vectors, are also well described in the scientific literature. See, for example Horsch, et al., *Science* 233:496–498 (1984), and Fraley, et al., *Proc. Nat'l. Acad. Sci. USA* 80:4803 (1983). Agrobacterium-mediated transformation is a preferred method of transformation of dicots.

Generation of Transgenic Plants

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., *Protoplasts Isolation and Culture, Handbook of Plant Cell Culture*, pp. 124–176, Macmillian Publishing Company, New York, (1983); and Binding, *REGENERATION OF PLANTS, PLANT PROTOPLASTS*, pp. 21–73, CRC Press, Boca Raton, (1985). Regeneration can also be obtained from plant callus, explants, somatic embryos (Dandekar, et al., *J. Tissue Cult. Meth.* 12:145 (1989); McGranahan, et al., *Plant Cell Rep.* 8:512 (1990)), organs, or parts thereof. Such regeneration techniques are described generally in Klee, et al., *Ann. Rev. of Plant Phys.* 38:467–486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Integrated Systems

Figure 11:
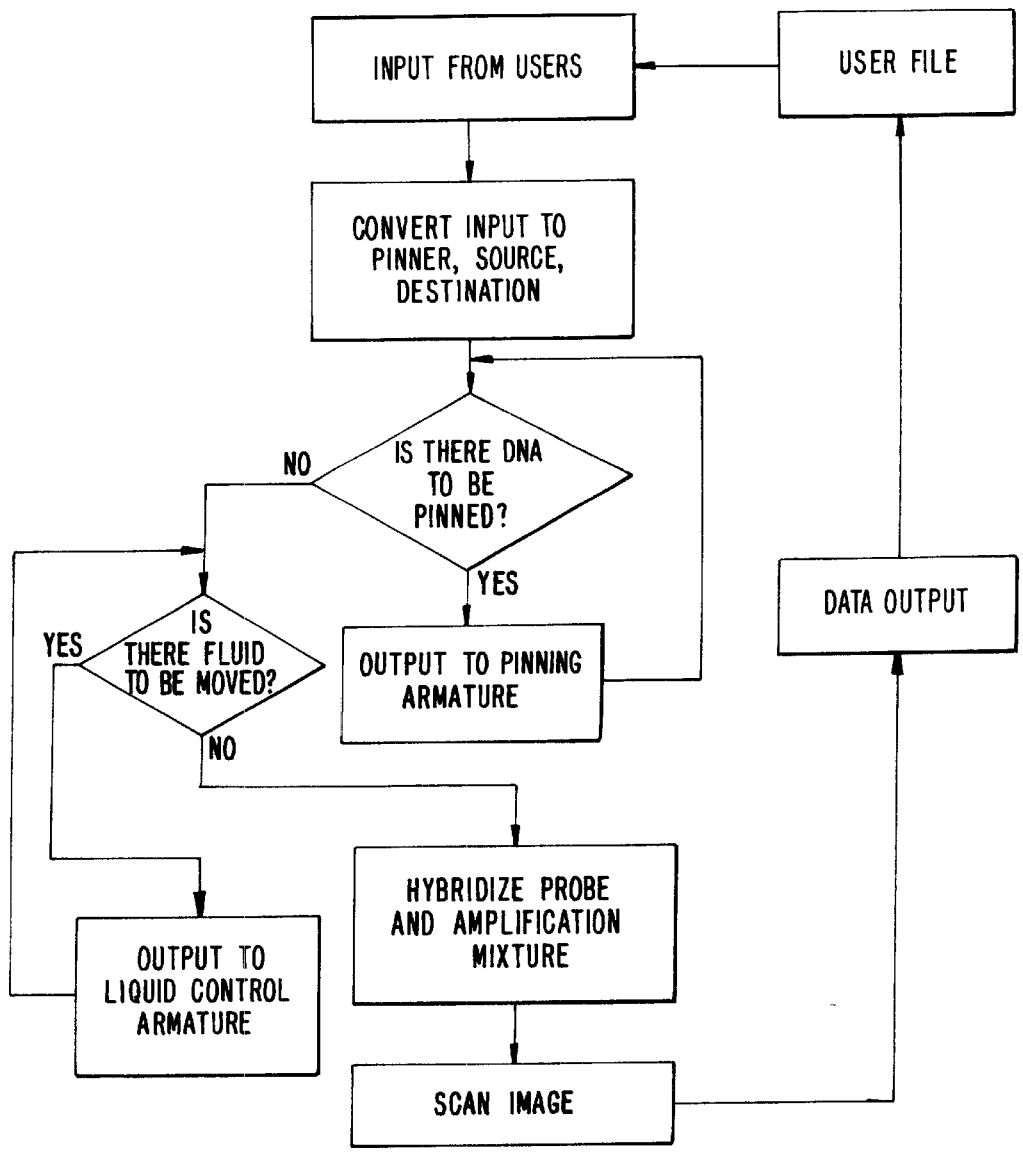
FIG. 11. Schematic of integrated system for AFLP Dots.

The invention provides integrated systems for blotting and hybridization analysis. Typical systems include a digital computer with high-throughput liquid control software, image analysis software, and data interpretation software. A robotic liquid control armature for transferring solutions from a source to a destination, is typically operably linked to the digital computer. A robotic pinning armature for transferring liquid comprising DNA to a solid support is optionally provided. An input device for entering data to the digital computer to control high throughput liquid transfer by the robotic liquid control armature and, optionally, to control transfer by the pinning armature to the solid support is commonly a feature of the integrated system, as is an image scanner for digitizing label signals from labeled probe hybridized to the DNA on the solid support operably linked to the digital computer. The image scanner interfaces with the image analysis software to provide a measurement of probe label intensity, where the probe label intensity measurement is interpreted by the data interpretation software to show whether the labeled probe hybridizes to the DNA on the solid support. An exemplar system is described in detail in the Examples below. A flowchart outlining an integrated system of the invention is provided by FIG. 11. A Dot Blot process Flow Chart is provided by FIG. 12.

EXAMPLES

The following examples are offered by way of illustration, and are not intended to be limiting. One of skill will immediately recognize a variety of alternate procedures, compositions, reagents and the like which can be substituted for those exemplified below.

1. Mapping AFLP Dot Markers to Maize Chromosomes

DNA of progeny of four unrelated mapping crosses (94 progeny from each cross) and DNA of the parental lines were used to create AFLP Dot blots (procedures described above for the various steps were used) to use in a mapping experiment to identify the locations of AFLP-Dot markers (polymorphic DNA fragments). For the first mapping population, the F2 population derived from an R67/W52 parent cross was used (R67/W52-F2). For the second mapping population, the F2 population derived from an R67/P38 parent cross was used (R67/P38-F2). The third mapping population was the F4 population derived from a parent cross of R03 and N46(RO3/N46-F4). The fourth mapping population was a recombinant inbred (RI) population derived from a B73/Mo17 parent cross developed by Charles Stuber, USDA/ARS, Raleigh, N.C. (B73/Mo17-RI).

Dot blots were made (using the previously described methods), that contained all four mapping populations, with each sample represented in four different locations, or "spots." Amplified dominant marker bands were labeled according to the directions in the ECL Direct Nucleic Acid Labeling and Detection System (Amersham). Each membrane was incubated with a labeled polynucleotide probe added to the hybridization solution. Following this, the membranes were washed as previously described, and then the blots were saturated with freshly made ECL Detection reagents and exposed to film.

a. Data Analysis

Film images of the hybridized blots were scanned and analyzed using the Optimate program. Total luminescence values were calculated for each sample by taking the average of each of the four replicate samples. The blot was standardized using average luminescence values for known "positive" samples (those containing a sequence complementary to the polynucleotide probe sequence) and "negative" samples (those not containing a sequence complementary to the polynucleotide probe sequence). The unknown samples were scored as positive and negative for hybridization with a polynucleotide probe by comparing the average sample luminescence value following probe hybridization with the standard values. Those unknown samples with luminescence values which fell within 2 or 3 standard deviations (SD) of the positive standard value were classified as "positive" and those samples with values within 2 or 3 SD of the negative standard value were classified as "negative." In general, 3 SD was used, unless there was significant overlap in the positive and negative standards, in which case 2 SD was used.

If the parents of a population were polymorphic for a band (one parent is negative and one is positive), the negatively scored progeny were scored as being homozygous for the allele of the negative parent, and the positively scored progeny were scored as being homozygous or heterozygous for the allele of the positive parent. Any samples that fell outside the ranges of the negative or positive scores were scored as having missing data.

Using the dot/blot hybridization results obtained for the mapping populations, segregation scores were generated. A segregation score determines whether the progeny share a genetic trait with parent A, parent B, or both parents. In a separate set of experiments, segregation scores for the same mapping populations were generated using several hundred RFLP markers whose locations in the maize genome are known. The segregation scores for the AFLP data and the segregation scores for the RFLP data were loaded into MapMaker (version 3.0). The MapMaker program calculated which RFLP markers were linked to the AFLP/Dot Markers in each mapping population.

b. Results

Three AFLP/Dot markers (p8950, p8955a, and 08946a) were linked to two RFLP markers (umc10a and umc26a) located on the short arm of maize chromosome 3 in bins 4 and 5. A bin is a region on the chromosome into which closely linked markers are grouped. Two unrelated mapping populations (R67/P38-F2 and B73/Mo17-RI) were used to map marker p8950a to this region of chromosome 3. In the F2 population, p8950a was linked to umc10a by an estimated distance of 18.4 centimorgan (cM). In the RI population, p8950a was linked to umc26a by an estimated distance of 23.7 cM. The placement of an AFLP/Dot marker, p8950a, to the same location in two unrelated mapping populations demonstrates that AFLP/Dot markers can be reliably used in mapping experiments, and in comparing populations having different genotypes.

This data indicates that the AFLP/Dot marker, p8950a, a sequence that was isolated from an AFLP band, is amplified from the same chromosomal location in two nonrelated crosses. This is very important if these sequences are to be used for marker-assisted selection or for DNA fingerprinting. Such analysis has been difficult or impossible in the gel-based AFLP system since in each cross each band has to be re-mapped since the bands are only recognized by size. The possibility exists that in different germplasm DNA strands of the same size but different sequence could be amplified. These amplified strands of the same size but different sequence come from different locations in, the genome, but would be indistinguishable by gel electrophoresis. By using dot blot hybridizations, these bands would be easily distinguished because the sequence of the band determines the score, not its size. Thus, using the methods of this invention, sequence specific hybridization prevents this error from happening.

Figure 10:
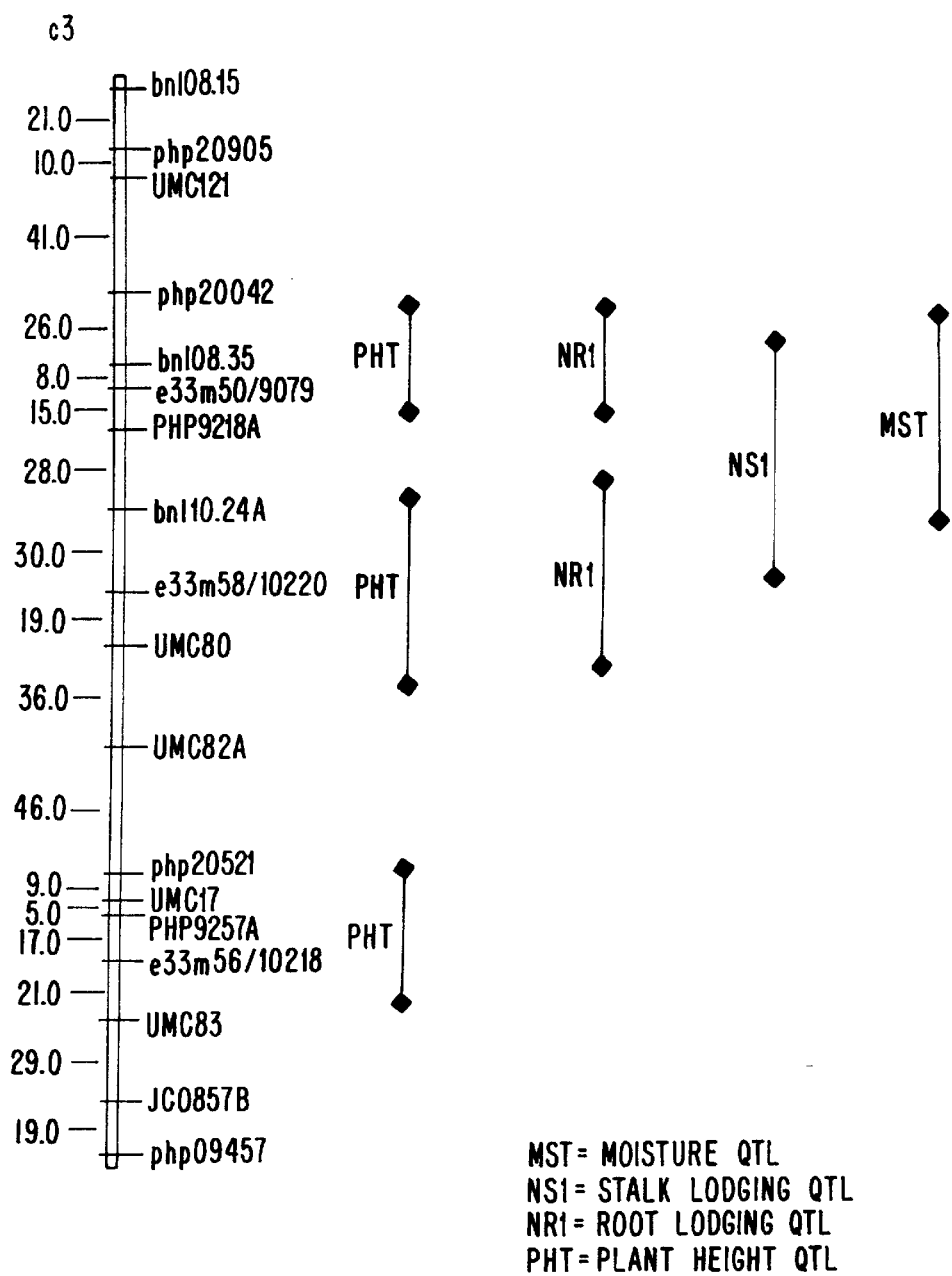
FIG. 10. Map of chromosome 3 in the R03/N46-F4 cross showing the location of QTL's for agronomic traits.

Two additional AFLP/Dot markers were shown to be linked to the same region of the short arm of maize chromosome 3. AFLP/Dot marker p8955a was linked to umc10a by an estimated distance of 9.7 cM in R67/P38-F2. AFLP/Dot marker p8946a was linked to p8950a by an estimated distance of 14.7 cM in B73/Mo17-RI. Other AFLP/Dot markers were located in other regions of the maize genome as shown in the RO3/N46-F4 map (FIG. 9). Many quantitative trait loci (QTL's) were identified for various agronomic traits in the RO3/N446-F4 population. FIG. 10 shows the location of several QTL's in relation to AFLP/DOTS markers generated. These markers are useful for selection for these traits.

2. Analysis of 16 Inbred Maize Strains

The Plus 3 products for 16 maize inbred strains were spotted onto pretreated nylon hybridization membranes as described in Example 1 above. These products were probed with 221 cloned DNA sequences and the degree of hybridization was analyzed as described above in Example, 1.

Each inbred was assigned a plus/minus score for each marker analyzed. Then, the plus/minus scores were compared for every possible pairing of the inbreds. This gives a distance between each pair of inbreds (AFLPDIST). (Table 1). "PED1" and "PED2" refer to the inbred strain used.

| | ALL DISTANCES | | | |
|---|---|---|---|---|
| OBS (PED1 × PED2) | AFLPDIST | RFLPDIST | RFLP250 | PEDDIST |
| 1 | 0.187 | 0.685 | 0.661 | 0.984 |
| 2 | 0.227 | — | — | 0.994 |
| 3 | 0.188 | 0.636 | 0.525 | 0.992 |
| 4 | 0.207 | 0.701 | 0.672 | 0.981 |
| 5 | 0.240 | 0.774 | 0.695 | 1.000 |
| 6 | 0.211 | 0.728 | 0.633 | 0.994 |
| 7 | 0.207 | 0.709 | 0.593 | 0.996 |
| 8 | 0.224 | 0.648 | 0.677 | 0.995 |
| 9 | 0.168 | — | — | 0.996 |
| 10 | 0.176 | 0.685 | 0.661 | 0.947 |
| 11 | 0.182 | 0.541 | 0.556 | 0.849 |
| 12 | 0.186 | 0.548 | 0.574 | 0.971 |
| 13 | 0.186 | 0.563 | 0.613 | 0.865 |
| 14 | 0.196 | 0.654 | 0.692 | 0.962 |
| 15 | 0.182 | 0.799 | 0.833 | 0.999 |
| 16 | 0.163 | — | — | 0.927 |
| 17 | 0.164 | 0.370 | 0.321 | 0.672 |
| 18 | 0.173 | 0.707 | 0.724 | 0.994 |
| 19 | 0.236 | 0.721 | 0.750 | 0.996 |
| 20 | 0.140 | 0.470 | 0.368 | 0.458 |
| 21 | 0.170 | 0.494 | 0.500 | 0.793 |
| 22 | 0.176 | 0.716 | 0.825 | 0.993 |
| 23 | 0.184 | — | — | 0.980 |
| 24 | 0.173 | 0.704 | 0.679 | 0.981 |
| 25 | 0.191 | 0.701 | 0.767 | 0.992 |
| 26 | 0.157 | 0.673 | 0.724 | 0.995 |
| 27 | 0.189 | 0.778 | 0.831 | 0.991 |
| 28 | 0.205 | 0.705 | 0.710 | 0.992 |
| 29 | 0.191 | 0.770 | 0.825 | 0.966 |
| 30 | 0.190 | — | — | 0.645 |
| 31 | 0.191 | — | — | 0.961 |
| 32 | 0.231 | — | — | 0.996 |
| 33 | 0.158 | — | — | 0.778 |
| 34 | 0.134 | — | — | 0.637 |
| 35 | 0.142 | — | — | 0.976 |
| 36 | 0.163 | — | — | 0.878 |
| 37 | 0.164 | — | — | 0.939 |
| 38 | 0.190 | — | — | 0.978 |
| 39 | 0.154 | — | — | 0.984 |
| 40 | 0.182 | — | — | 0.973 |
| 41 | 0.192 | — | — | 0.984 |
| 42 | 0.197 | — | — | 0.906 |
| 43 | 0.205 | 0.732 | 0.724 | 0.989 |
| 44 | 0.246 | 0.721 | 0.679 | 0.999 |
| 45 | 0.159 | 0.506 | 0.474 | 0.622 |
| 46 | 0.121 | 0.420 | 0.536 | 0.291 |
| 47 | 0.189 | 0.691 | 0.789 | 0.992 |
| 48 | 0.177 | — | — | 0.887 |
| 49 | 0.186 | 0.704 | 0.571 | 0.918 |
| 50 | 0.220 | 0.653 | 0.633 | 0.984 |
| 51 | 0.176 | 0.648 | 0.621 | 0.989 |
| 52 | 0.203 | 0.649 | 0.695 | 0.982 |
| 53 | 0.200 | 0.682 | 0.677 | 0.982 |
| 54 | 0.171 | 0.759 | 0.719 | 0.970 |
| 55 | 0.217 | 0.665 | 0.690 | 1.000 |
| 56 | 0.221 | 0.774 | 0.763 | 0.987 |
| 57 | 0.166 | 0.732 | 0.724 | 0.993 |
| 58 | 0.135 | 0.439 | 0.492 | 0.600 |
| 59 | 0.185 | — | — | 0.971 |
| 60 | 0.149 | 0.695 | 0.724 | 0.942 |
| 61 | 0.199 | 0.609 | 0.742 | 0.866 |
| 62 | 0.165 | 0.545 | 0.600 | 0.923 |
| 63 | 0.118 | 0.422 | 0.443 | 0.655 |

-continued

ALL DISTANCES

| OBS (PED1 × PED2) | AFLPDIST | RFLPDIST | RFLP250 | PEDDIST |
|---|---|---|---|---|
| 64 | 0.168 | 0.652 | 0.781 | 0.955 |
| 65 | 0.199 | 0.619 | 0.627 | 0.907 |
| 66 | 0.249 | 0.775 | 0.754 | 1.000 |
| 67 | 0.230 | 0.758 | 0.714 | 1.000 |
| 68 | 0.221 | 0.648 | 0.649 | 1.000 |
| 69 | 0.189 | — | — | 0.933 |
| 70 | 0.171 | 0.673 | 0.643 | 0.986 |
| 71 | 0.211 | 0.682 | 0.567 | 0.994 |
| 72 | 0.201 | 0.667 | 0.586 | 1.000 |
| 73 | 0.214 | 0.701 | 0.695 | 0.998 |
| 74 | 0.205 | 0.631 | 0.581 | 0.976 |
| 75 | 0.163 | 0.726 | 0.719 | 1.000 |
| 76 | 0.076 | 0.265 | 0.263 | 0.541 |
| 77 | 0.105 | 0.771 | 0.828 | 0.994 |
| 78 | 0.207 | — | — | 0.940 |
| 79 | D.182 | 0.663 | 0.544 | 0.943 |
| 80 | 0.181 | 0.696 | 0.639 | 0.965 |
| 81 | 0.192 | 0.598 | 0.593 | 0.975 |
| 82 | 0.205 | 0.794 | 0.900 | 0.981 |
| 83 | 0.216 | 0.689 | 0.651 | 0.983 |
| 84 | 0.188 | 0.694 | 0.690 | 0.971 |
| 85 | 0.169 | 0.716 | 0.825 | 0.994 |
| 86 | 0.183 | — | — | 0.894 |
| 87 | 0.165 | 0.642 | 0.464 | 0.925 |
| 88 | 0.190 | 0.689 | 0.633 | 0.989 |
| 89 | 0.168 | 0.612 | 0.586 | 0.994 |
| 90 | 0.169 | 0.754 | 0.797 | 0.992 |
| 91 | 0.192 | 0.693 | 0.645 | 0.985 |
| 92 | 0.164 | 0.699 | 0.614 | 0.975 |
| 93 | 0.164 | — | — | 0.982 |
| 94 | 0.165 | 0.704 | 0.719 | 0.999 |
| 95 | 0.183 | 0.545 | 0.541 | 0.955 |
| 96 | 0.156 | 0.491 | 0.424 | 0.961 |
| 97 | 0.095 | 0.415 | 0.367 | 0.761 |
| 98 | 0.172 | 0.591 | 0.714 | 0.992 |
| 99 | 0.190 | 0.699 | 0.690 | 0.938 |
| 100 | 0.140 | — | — | 0.981 |
| 101 | 0.164 | — | — | 0.995 |
| 102 | 0.163 | — | — | 0.997 |
| 103 | 0.176 | — | — | 0.985 |
| 104 | 0.160 | — | — | 0.977 |
| 105 | 0.152 | — | — | 0.926 |
| 106 | 0.139 | 0.485 | 0.500 | 0.720 |
| 107 | 0.132 | 0.467 | 0.448 | 0.815 |
| 108 | 0.178 | 0.649 | 0.729 | 0.875 |
| 109 | 0.128 | 0.352 | 0.387 | 0.599 |
| 110 | 0.167 | 0.648 | 0.544 | 0.997 |
| 111 | 0.183 | 0.482 | 0.484 | 0.843 |
| 112 | 0.196 | 0.500 | 0.524 | 0.794 |
| 113 | 0.173 | 0.503 | 0.606 | 0.821 |
| 114 | 0.178 | 0.637 | 0.672 | 0.998 |
| 115 | 0.169 | 0.460 | 0.541 | 0.875 |
| 116 | 0.184 | 0.508 | 0.563 | 0.894 |
| 117 | 0.157 | 0.562 | 0.525 | 0.999 |
| 118 | 0.153 | 0.557 | 0.692 | 0.913 |
| 119 | 0.171 | 0.634 | 0.667 | 0.953 |
| 120 | 0.193 | 0.620 | 0.556 | 0.997 |

Figure 3:
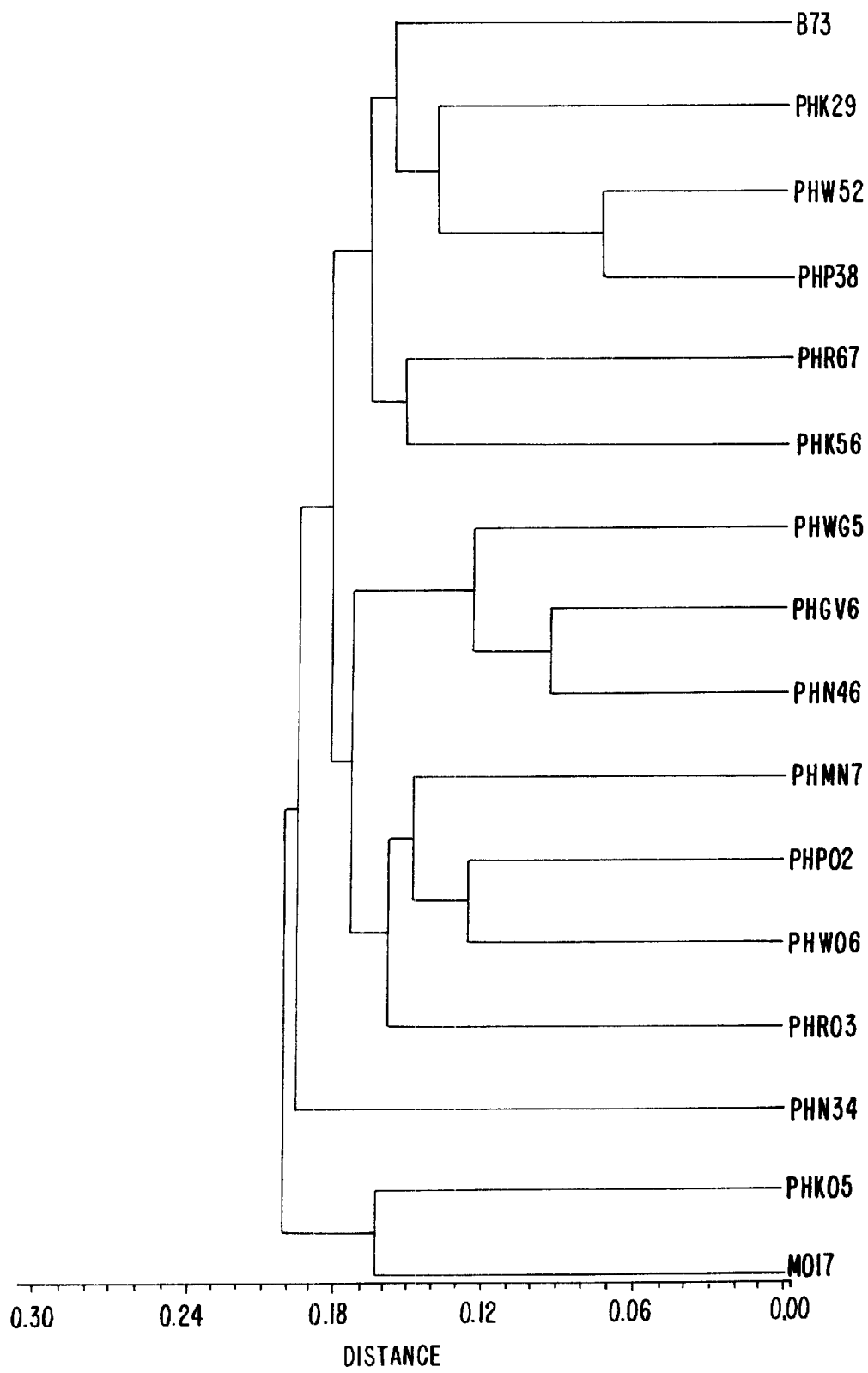
FIG. 3. Cluster plot of relative AFLP/Dot distances of 221 markers in 16 inbred maize strains.
Figure 4:
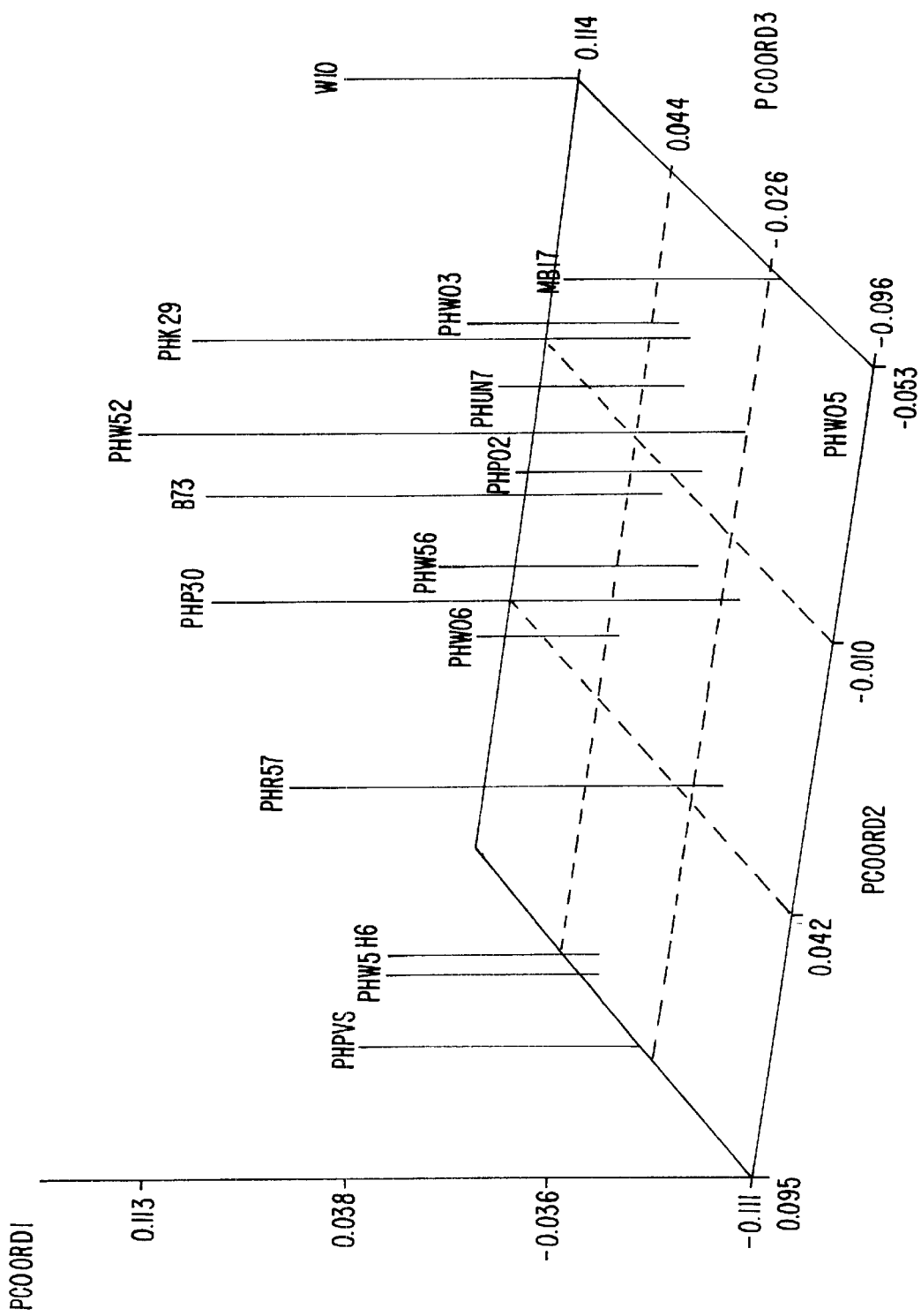
FIG. 4. Three-dimensional cluster plot of relative AFLP/Dot distances of 221 markers in 16 inbred maize strains.

A matrix of all possible pairwise distances was created using the AFLP dot/blot data. For two inbreds (hypothetically "i" and "j"), GS(ij) was calculated by multiplying the number of markers with positive scores for inbred i and inbred j by two, and dividing that number by the sum of the number of markers with positive scores in inbred i plus the number of markers with positive scores in inbred j. GS(ij) is then the genetic similarity between the i-th and j-th lines. The genetic distance GD(ij) used to calculate the dendrograms is 1-GS(IJ). A cluster program was run to reduce the data to a cluster showing associations among the inbreds based upon the AFLP dot/blot data. (FIG. 3). A three-dimensional representation of this data is shown in FIG. 4, which indicates the relative distances of the markers used in the 16 inbreds. This provides a measure of the degree relatedness of the inbreds based on the AFLP Dot markers used.

DNA samples from the same 16 inbreds were also analyzed for (1) pedigree distances calculated using either Sewalls or Wright's genetic distance calculations (where pedigree distance=1 Malecot coefficient of pedigree similarity) (PEDDIST) and (2) distances between pairs of inbreds using RFLP analysis. For the RFLP analysis, one comparison of distances was made using 80 standard fingerprinting polynucleotide probes (RFLPDIST) and a second comparison was made using a subset of 29 of the 90 probes (RFLP250). The 80 probes hybridized with a total of 685 DNA bands. produced by electrophoresis of DNA from the 16 inbreds following AFLP restriction enzyme digestion and amplification procedure described above in this example. The subset of 29 probes hybridized with a total of 250 DNA bands. The relative distances between pairs of hybrids for these analyses are shown in Table 1.

Figure 5:
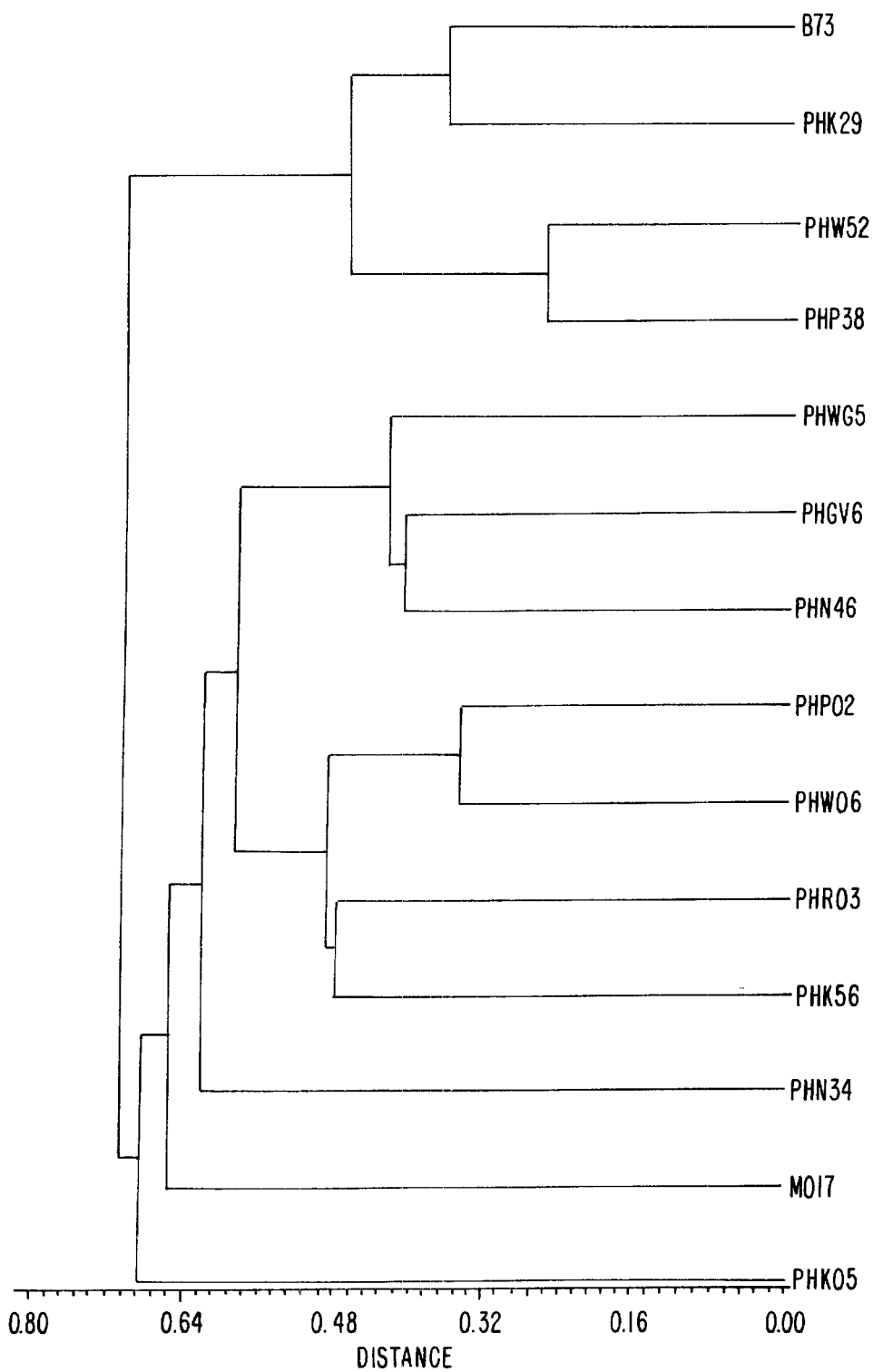
FIG. 5. Cluster plot of relative RFLPDIST distances of 221 markers in 16 inbred maize strains.
Figure 6:
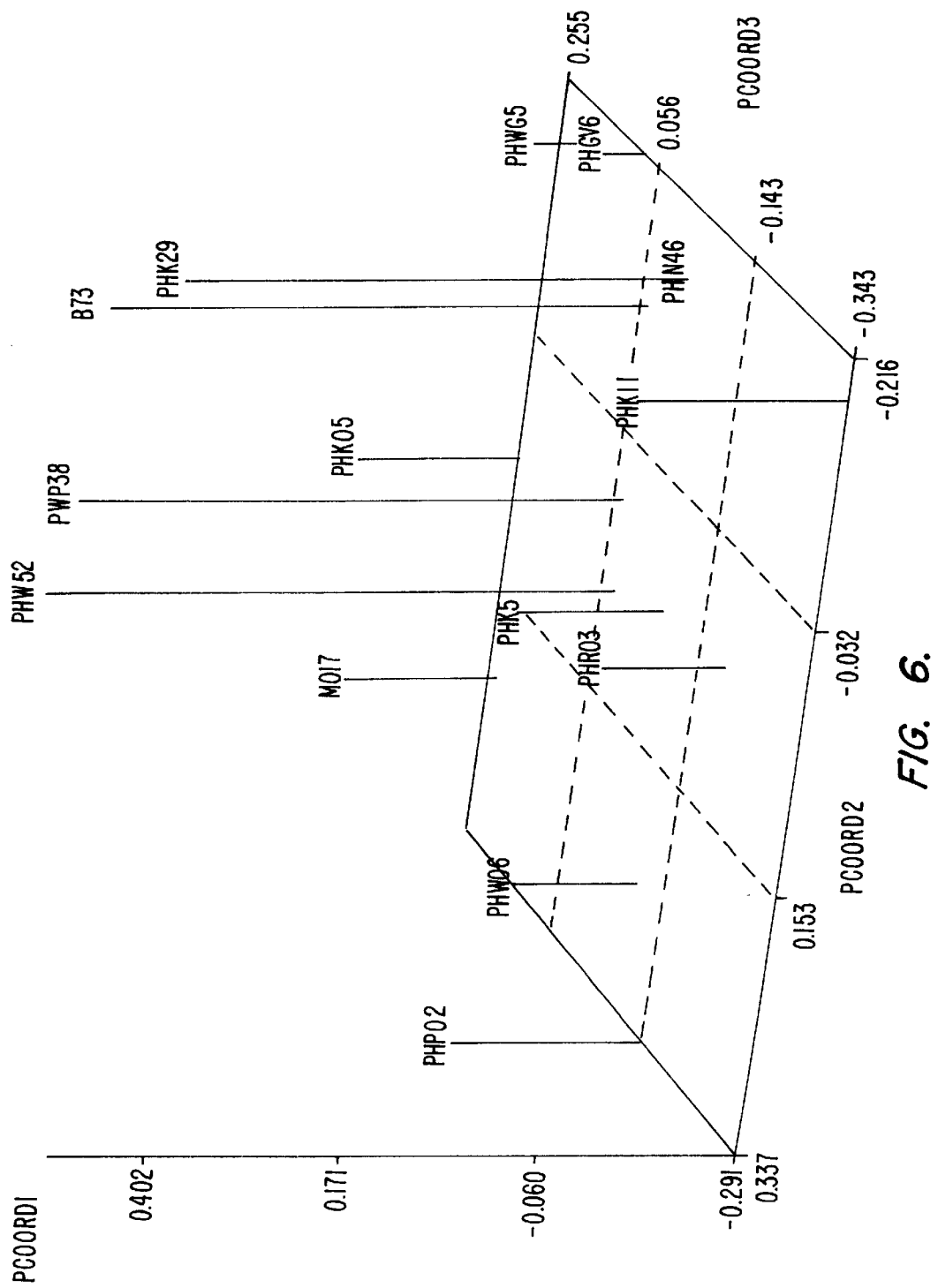
FIG. 6. Three-dimensional cluster plot of relative RFLP-DIST distances of 221 markers in 16 inbred maize strains.
Figure 7:
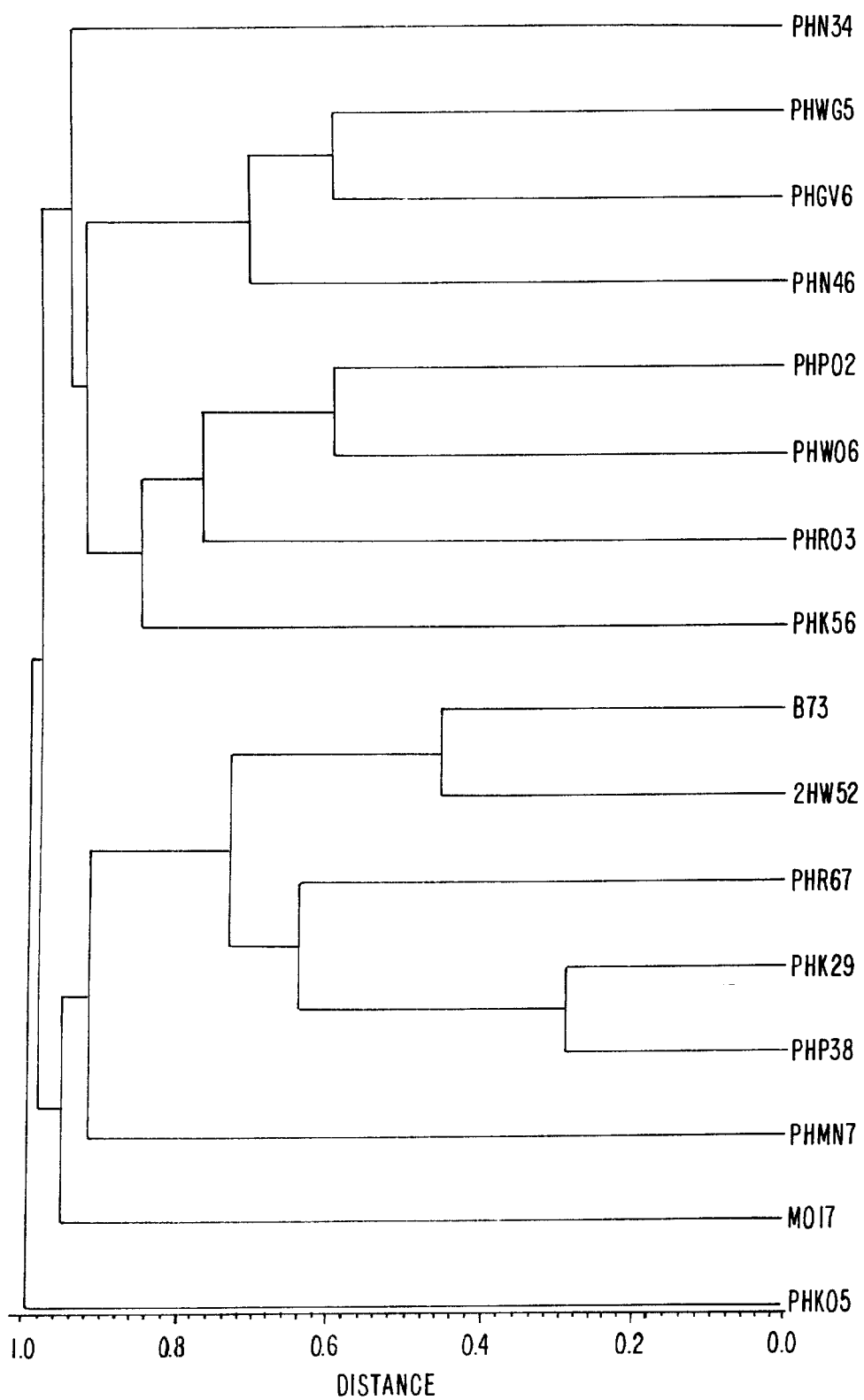
FIG. 7. Cluster plot of relative PEDDIST distances of 221 markers in 16 inbred maize strains.
Figure 8:
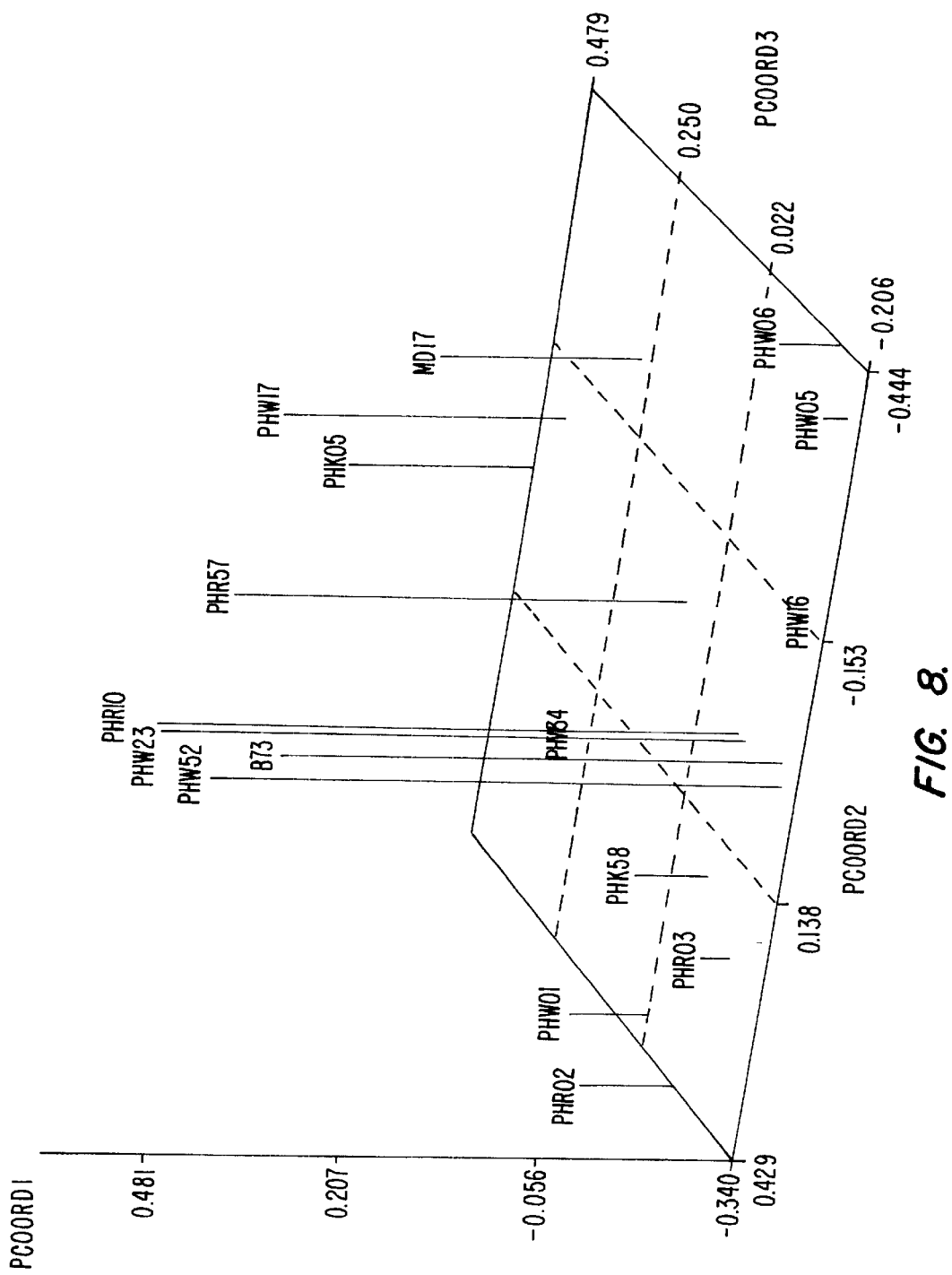
FIG. 8. Three-dimensional cluster plot of relative RED-DIST distances of 221 markers in 16 inbred maize strains.
Figure 9A:
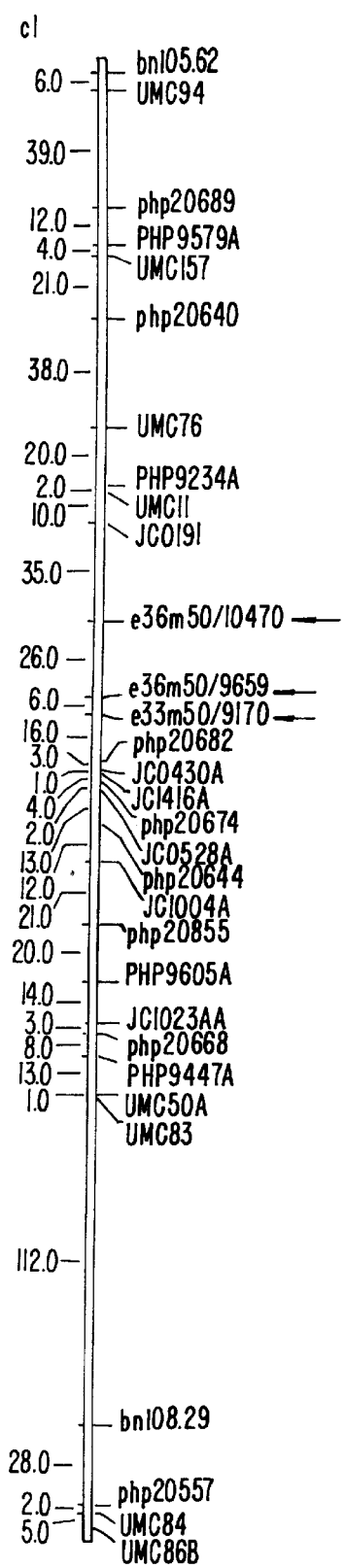
FIG. 9, Panels 9A, 9B, 9C, 9D, 9E, 9F, 9G, 9H, 9I and 9J. Map of the ten maize chromosomes showing the distribution of 22 AFLP/DOT markers identified by the methods herein in the RO3/N46-F4 cross.
Figure 9B:
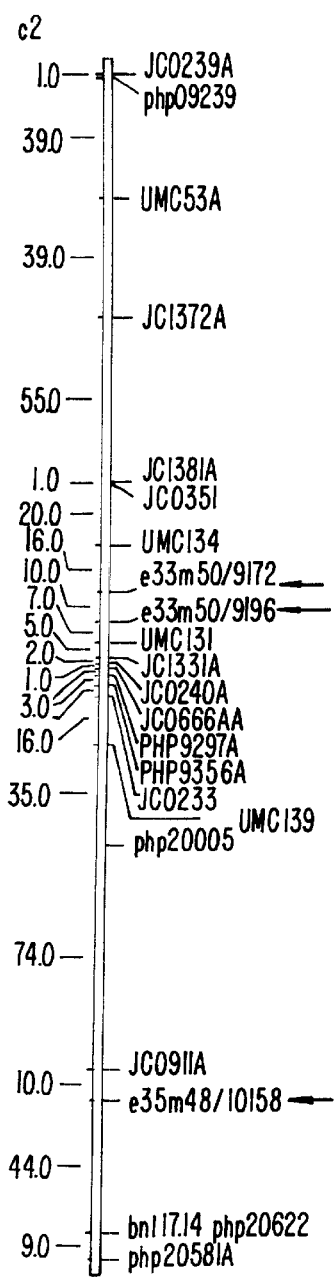
Figure 9C:
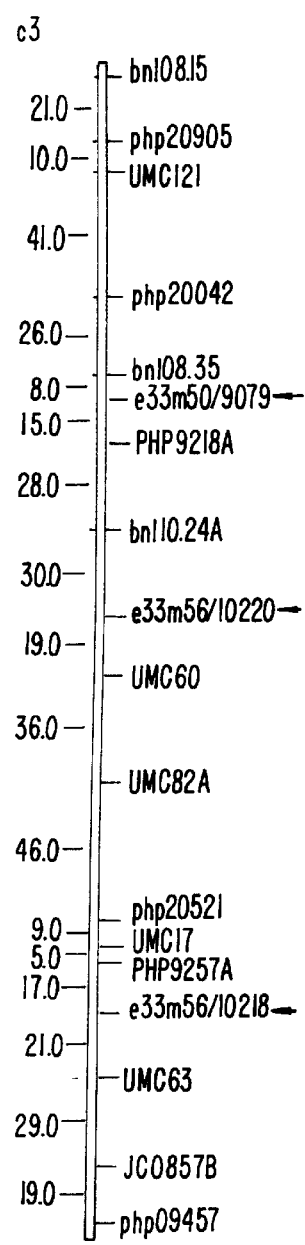
Figures 9I, 9J:
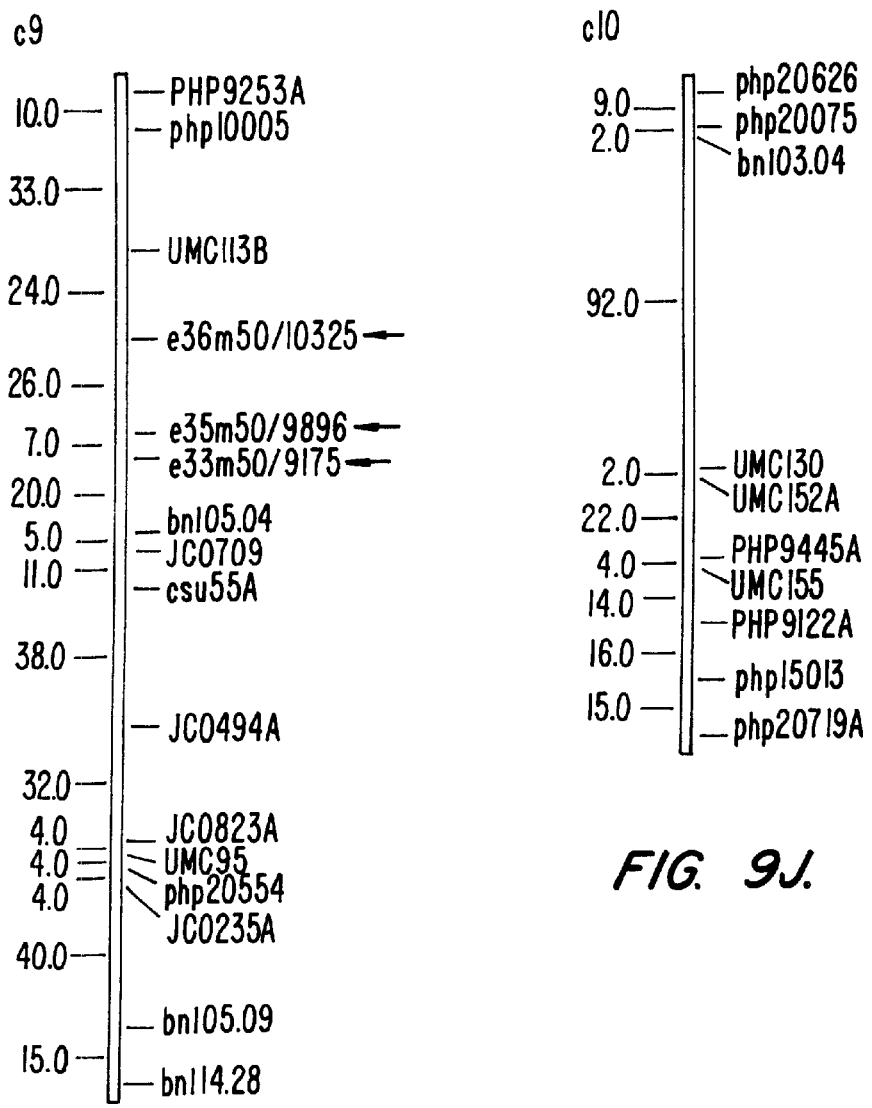

FIG. 5 shows a two-dimensional plot of the cluster data for the RFLPDIST and FIG. 6 shows this same data in three-dimensional format. Similarly, FIGS. 7 and 8 show the PEDDIST cluster in two- and three-dimensional format.

Using the data in Table 1, the means and standard deviations for each subset of distances (AFLP, PED, RFLP and RFLP250) were calculated (Table 2).

TABLE 2

SIMPLE STATISTICS

| Variable | Probes (Bands) | N | Mean | Std Dev | Sum | Minimum | Maximum |
|---|---|---|---|---|---|---|---|
| ASHDIST | (250) | 120 | 0.180075 | 0.028588 | 21.609000 | 0.076000 | 0.249000 |
| RFLPDIST | 80 (685) | 91 | 0.632330 | 0.111926 | 57.542000 | 0.265000 | 0.799000 |
| RFLP250 | 29 (250) | 91 | 0.632703 | 0.123887 | 57.576000 | 0.263000 | 0.900000 |
| PEDDIST | — | 120 | 0.923033 | 0.124749 | 110.764000 | 0.291000 | 1.000000 |

Using these values, Pearson correlation coefficients were calculated to determine the correlations of different distance data sets (ASHDIST, RFLPDIST, RFLP250 and REDDIST). These results are presented in Table 3.

TABLE 3

PEARSON CORRELATION COEFFICIENTS/PROB > /R/
UNDER HO: RHO = 0/NUMBER OF OBSERVATIONS

|  | ASHDIST | RFLPDIST | RFLP250 | PEDDIST |
|---|---|---|---|---|
| ASHDIST | 1.00000<br>0.0<br>120 | 0.67027<br>0.0001<br>91 | 0.53425<br>0.0001<br>91 | 0.59508<br>0.0001<br>120 |
| RFLPDIST | 0.67027<br>0.0001<br>91 | 1.00000<br>0.0<br>91 | 0.85078<br>0.0001<br>91 | 0.78687<br>0.0001<br>91 |
| RFLP250 | 0.53425<br>0.0001<br>91 | 0.85078<br>0.0001<br>91 | 1.00000<br>0.0<br>91 | 0.64890<br>0.0001<br>91 |
| PEDDIST | 0.57508<br>0.0001<br>120 | 0.78687<br>0.0001<br>91 | 0.64890<br>0.0001<br>91 | 1.00000<br>0.0<br>120 |

3. Exemplary Integrated Systems to Support and Facilitate Implementation of an Aflp Dots Integrated systems for blotting and hybridization analysis of the present invention typically include a digital computer with high-throughput liquid control software, image analysis software, and data interpretation software, a robotic liquid control armature for transferring solutions from a source to a destination, which robotic liquid control apparatus is operably linked to the digital computer, a robotic pinning armature for transferring liquid comprising DNA to a solid support, an input device (e.g., a computer keyboard) for entering data to the digital computer to control high throughput liquid transfer by the robotic liquid control armature and, optionally, to control transfer by the pinning armature to the solid support and an image scanner for digitizing label signals from labeled probe hybridized to the DNA on the solid support operably linked to the digital computer. The image scanner interfaces with the image analysis software to provide a measurement of probe label intensity. Typically, the probe label intensity measurement is interpreted by the data interpretation software to show whether the labeled probe hybridizes to the DNA on the solid support. An example integrated system is set forth in FIG. 11. A Dot Blot process Flow Chart is provided by FIG. 12.

Software to support the AFLP DOTS sample processing can be divided into 4 functional categories: 1) liquid transfer control software, 2) image analysis software, 3) data management software, and 4) data interpretation software.

The approach taken to provide an integrated system for the AFLP DOTS process was to create applications which share information through data files which the applications can read and create. For flexibility and ease of use, these files were formatted as simple text files and/or in Microsoft Excel® worksheet format. This allowed viewing and editing of the files through the use of commercially available Microsoft Excel®. Those of skill in the art will recognize that the following approach is only one possible set of systems that could be used in the support and facilitation of the process of the present invention. Other systems can easily designed to fit the particular needs of the user in the practice of the invention.

A Microsoft Windows® user interface was developed for most applications using Microsoft Visual Basic 4.O®. Most applications were developed for a 32-bit environment to run under Microsoft Windows 95®. The exceptions to this involve the image analysis software developed by Optimas Corporation, Optimas 5.0 (and Optimate, the runtime version), and "Handler." Optimas applications are 16-bit and macros (scripts) generated for these programs run in a 16-bit mode. A handler application ("Handler") was developed in a 16-bit version to accommodate Windows 3.1, which is the manufacturer approved operating system for the Beckman Biomek® 2000®.

a. Liquid Transfer Software

Three Visual Basic programs were developed to facilitate the transfer of solutions from one container (i.e. reservoirs, microtiter plates, tubes, membranes etc.) to another. A plate randomizer application and a handler application are used in conjunction with Beckman Biomek® robotic liquid handlers. Pinner was developed to support the Sagain ORCA® robotic arm system, which is used to array samples onto nylon membranes.

b. Plate Randomizer Application

This application can be utilized early in the AFLP DOTS process to assign samples to well locations in a 96-well microtiter plate. The program provides the capability to generate a randomized block design for sample placement. If a randomized sample layout is not used samples are assigned to well locations manually by the lab technician. The program is designed to present information in a simple 2 tab folder display using standard Visual Basic® controls. All input and export functions utilize Visual Basic's common dialog box control to prompt the user for filenames and paths.

The Plate Randomizer program utilizes a random number generator (seeded with the current time) to assign a unique number, within an appropriate range, to each well in the sample block. Each 96-well plate is divided automatically into a geometric pattern of 1 to 6 blocks depending on the number of replicates to be created for each sample (one replicate per block, 6 replicates maximum). A set of option buttons is displayed on the first tab of the program and the user can select the number of blocks to be created on the plate. A command button is then pressed to initiate generation of the random layout.

Once an array of random numbers has been created, the user presses a command button to match sample IDs to the random numbers. The sample IDs are read from a stored Excel® spreadsheet sequentially from 1 to the number of unique samples to be assigned to the plate. A Visual Basic® data control is used to access the Excel® spreadsheet file.

The second tab of the program provides prompts for creation and export of files describing the randomized plate layout. Text boxes are displayed allowing the user to define an experiment ID, plate ID, destination plate type (from a drop down menu of predefined plates), and the volume of sample to be transferred. Two export formats can be selected from. The formats are designed to be readable by other software applications used in the AFLP DOTS process. Specifically, a handler application, which generates the code used to operate a Beckman Biomek® 2000®, and a detangler application, which is used to track samples and generated data through the AFLP DOTS process, have been developed (see infra). A text file can be created with columns of information defining the experiment ID, plate number, well number, and sample ID. The program automatically determines if a text file of the specified name already exists. If so, the program appends new information to the existing file. If the file does not already exist, the program creates a new file. The text file is used by the detangler application for subsequent data tracking. An Excel® spreadsheet can be created with columns of information defining the well number, sample ID, volume of the sample and plate type. A "done" column is also created. This data column can contain flags used by the handler application to determine whether a sample has already been processed or is awaiting processing.

Once files are created describing the current randomized plate layout the user can quit the program or restart the process to generate more plate descriptions.

c. Handler Application

The currently available commercial software package, BioWorks® 1.4®, provided by Beckman Instruments, Inc. to control and operate their Biomek® 2000 robotics liquid handler has several limitations which made it, on its own, unsuitable for the high throughput needs of the AFLP DOTS process. However, BioWorks® and the firmware within the Biomek® 2000 does support a low level scripting capability based on the publicly available Tool Command Language (TCL). Beckman has incorporated a TCL interpreter into the Biomek® 2000 and has included TCL extensions (Bioscript®) to allow direct motor control and other needed instrument functionality. The approach taken to utilize a Biomek® 2000 liquid handler to automatically transfer samples from one container to another for the AFLP DOTS process is to generate TCL/Bioscript code which can drive the liquid handler to perform the needed operations. A 16-bit (to run under Microsoft Windows 3.1® and Microsoft Windows 95®) application to generate the TCL/Bioscript code was created in Microsoft Visual Basic 4.O®. This application is currently referred to as "Handler."

Handler is designed to allow a user to specify parameters for a liquid transfer and automatically generate complex TCL/Bioscript code which can be downloaded into the instrument by BioWorks® and executed. Handler utilizes a Windows® type display employing a 3 tab folder design on the data entry form. Tab one displays prompts for liquid transfer parameters which are needed to define a particular transfer operation. Tab two displays prompts for creating and exporting a TCL/Bioscript. Tab three provides prompts allowing the user to customize many default transfer parameters.

Two types of transfers are supported by Handler. An "auto-populate" option is provided which allows the system to generate scripts which will automatically move samples in an ordered manner from a source to a destination. All transfer volumes are identical and the pattern of transfers is predetermined by the software. These transfers employ the multi-tip tools (and High Density Replicating Tool) provided with the Biomek® machine. The other option is to "populate by template". This option allows the user to specify Excel® files which tell the system where to get specific liquids and where to deliver them. This allows the ;user to sort or randomize samples, and transfer different amounts for each sample in a set. These transfers employ the single tip tools provided with the Biomek®.

A basic assumption made by the Handler software is that for any transfer there will be a "source" and a "destination" for the material to be transferred. The software is, therefore, designed to prompt the user for source and destination information from within frames on the data entry form. The user is also prompted for additional information on how many samples, how many replicates, and how many sets of transfers are needed from a frame location between the source and destination frames. A worksurface frame is also provided to allow the user to freely specify through a graphical display where on the worksurface the source and destination locations will be.

Source and destination information required by Handler includes the volumes to be transferred, basic vessel type (reservoir of microtiter plate), the specific vessel type (what type of reservoir or microtiter plate), how deep to go within the vessels for aspirate and dispense purposes and whether or not to tip-touch when leaving a vessel. Whether or not to bulk aspirate and whether or not to employ air gaps are requested from within the source frame. Whether or not to employ a mix procedure and whether or not to use a sample blow out step are requested from within the destination frame.

Specific vessel types are selected from a scrolling menu for both the source and destination. This information is automatically read from an Excel® spreadsheet which contains tables for not only the vessels but also provides reference information on pipette tips, pipetting tools, worksurface locations, calibration parameters, and other information required by the system for operation. The use of this spreadsheet allows Handler to utilize any vessel which can be defined by the user and will allow the system to accommodate changes in type, size, and shape of tools and rips and allows physical changes to the worksurface.

An experienced user can enter all necessary information into the form within a minute or two. Once the information is entered the user is prompted to have the software check for validity of the assignments before the actual script is generated. The system checks to determine if the number of source and destination locations makes sense. It also checks to determine if enough tips are available, if volumes are within the limits of the available tools, and if the vessels can hold the specified volumes. If all settings are considered valid then the command button allowing generation of the actual script is enabled. If not, a message is displayed indicating the nature of the problem.

It is possible to alter the speeds, accelerations, and delays employed for all transfers. However, most scripts generated by a user can utilize predetermined default settings for these parameters. Therefore, prompts allowing the user to change these settings are provided on the third tab of the form and are not visible unless the tab is selected.

All TCL/Bioscripts generated by Handler employ TCL procedure calls to reduce the size of the scripts. Procedures are generated for general aspirate and dispense routines. Specific parameters are passed to these procedures to implement specific transfers. The user can also select options allowing for the scripts to be automatically annotated (programmers comments added), to provide TCL feedback output (status displays), and to provide necessary TCL procedures to simulate Biomek® functions (used for testing and debugging). The user also is provided with an option to generate a "iparameters file" along with the TCL/Bioscript. The parameters file provides a listing of all settings that were used to generate the associated TCL/Bioscript. This file provides a means for documenting the settings that were used and gives the user a reference if a script must be regenerated.

d. ORCA-based Pinner System

To support planned AFLP DOTS hybridization studies, nylon membranes with surface arrays of bound DNA are created to allow rapid screening of large numbers of DNA samples. The ORCA (Optimized Robot for Chemical Analysis) Pinner System was developed to create these arrays. System Specifications: The Pinner system is capable of: 1) providing as many membrane dot arrays as possible from a given single source of DNA, 2) providing as many dots as possible in an array for multiple DNA samples, 3) providing densely packed arrays of dots to reduce size and cost of hybridization materials, 4) providing rapid creation of dot arrays, 5) providing fairly uniform or quantifiable amounts of DNA per transfer, 6) providing some user control over the amount of DNA transferred to dots in the array, 7) providing some flexibility in the location of dots in the array, 8) providing some flexibility in selection of source DNA to be used for each transfer, 9) providing control of potential cross-contamination sample to sample and periodic decontamination of the pinner tool.

A pinner system was designed which could transfer small amounts of DNA containing liquid from microtitre plates to a nylon membrane. The Sagian (formerly HP) ORCA® robot arm was proposed as an automation tool to rapidly and accurately accomplish the transfer of the liquid. The robot picks-up a pinner and dips the pinner into the wells of a microtitre plate. The pinner, with a small amount of DNA solution on the tip of each pin, then blots on to a nylon membrane thereby transferring the DNA from the microtitre plate to the nylon surface. The robot arm is programmed to repeat this process many times and produce multiple arrays of DNA dots until the DNA solution in the microtitre plate wells is exhausted.

The ORCA robot arm is a commercially available system (Sagian Incorporated) composed of a multijointed robot arm on a rail. The arm can move along the rail and pickup and manipulate objects within its reach. ORCA systems are available with 1 or 2 meter rails and a 0.5 meter deep table along one or both sides of the rail. An ORCA system employing a 2 meter rail and a table on one side of the rail was utilized in this instance.

A commercially available pinner tool from Generics Inc. (UK) was selected. This tool offers the advantages of low cost (approx. $6 per tool) disposability, and the capability to pin from 384 well (4X) microtitre plates. The pinner tool is formed polypropylene plastic and composed of 384 plastic pins (each approximately 1 cm long) aligned in a 16 by 24 array and attached to a backplate. A plastic flange along one side of each pinner tool is removed with a saw to allow four medium size binder clips to be fastened to each pinner tool. These binder clips provide a lip under which the robot jaws slide in order to pickup the pinner tool.

Custom designed pinner tool jaws were designed to allow the ORCA robot arm to grip the pinner tool. The jaws were constructed of a set of ORCA finger blanks to which two metal plates were bolted. These metal plates were drilled and tapped to accommodate 'I' shaped metal plywood clips which would slide under the binder clips on the pinner tool and also provide for a base against which the robot arm could apply pressure to the pinner tool. A standard ORCA jaws holder was elevated above the table surface to accommodate the new jaws by placing steel spacers under the jaws holder where it is bolted to the ORCA table. This jaws holder provides a resting place for the new pinner jaws.

To accommodate the DNA solution source microtitre plates and holders for the pinner tools, a metal frame was built from locally available wall shelf bracket rails. These rails were cut to length and assembled to form cross-shaped dividers against which microtitre plates could be positioned. The dividers were carefully bolted to the ORCA table surface to form a precisely squared grid for the microtitre plates. Careful alignment of the dividers and plates is essential to successful pinning operation with the robot control software that was developed. Additional brackets and bolts were used to securely fasten four 4×microtitre plates to the table against the dividers. These plates became holders for four pinner tools. The pinner tools sit with their pins in the wells of the microtitre plates. This provides storage positions for the four pinner tools which are precisely located on the table surface. A swing-arm was constructed from a length of shelf bracket rail. This swing-arm was fitted with four window screen spring tensioners. The swing arm was then bolted to the ORCA table such that it could swing back and forth allowing for insertion or extraction of four 4X DNA source plates against the dividers. To hold the four plates securely in position, the swing-arm could be fastened with a finger screw such that the spring tensioners press the 4X source plates against the dividers.

A thin galvanized steel sheet (flashing material) was bolted to the ORCA table adjacent to the source plates and pinner tools. This sheet provides the pallet upon which the nylon membrane rests. A thin polyurethane foam pad was laid on the sheet and surrounded by strips of magnetic tape. The nylon membrane is placed over the foam pad and the magnetic snips. During the pinning process the membrane is held firmly in place by additional strips of magnetic tape which adhere to the magnetic strips under the membrane. This entire membrane support pallet is sized to accommodate 15 dot arrays (3×5) on a single sheet of nylon membrane.

A sonic bath was positioned on one end of the ORCA table. This bath is electrically connected to a motion sensing AC switch mounted in an outlet box and positioned such that the sensor points up toward the ceiling. The motion sensor is shielded by a 6 inch long, 3 inch diameter piece of cardboard tubing to provide a narrow field of view for the motion sensor. The robot arm is programmed to pass over the motion sensor before moving the pinner tool to the sonic bath. The sensor detects the warmth of the robot arm and turns the sonio bath on for approximately 30 seconds (set by controls available on the motion sensor switch). This allows the pinner to be cleaned periodically (as defined in the software) and the bath to be automatically switched on and off as needed.

The ORCA robot arm system is provided with Hewlett Packard control software (MDS) which allows the user to define robot motions, collect and store data, and interface with the user. The MDS programming environment was used to support pinning operations and was supplemented with a custom designed Visual BASIC user interface to make pinning operations accessible to the average lab user.

Software to support pinning was developed in a layered manner. Simple robot motions were programmed and stored as motion files. These motion files were then called by sub-procedures which defined the sequence of motions needed to do individual processes involved in pinning. These sub-procedures were called by other procedures which combined the various pinning processes into groups which generally function together in the pinning process. Finally, a master procedure uses parameters which can be set by the user and calls the sub-procedures as needed to accomplish the desired task. The Visual BASIC user interface allows the user to specify how the pinning is to be accomplished and defines the parameters needed by the master procedure.

To reduce the number of motions for which the robot would need to be trained, the concepts of frames and offsets were used. Since four pinner tools and four source plates were provided for in the hardware design there is a requirement for software to pickup or put down tools at four locations and to pin from 4 different source plates. A motion was taught which allowed for a tool to be picked up or put down at one location. Likewise, a motion was taugh, allowing for pinning from the corresponding source plate for the selected pinning tool. Four frames were then defined which allowed the taught motions to be executed at four different locations on the table. These locations were defined to match the locations of the four pinner tools and four source plates.

In a similar fashion, 12 frames were defined to represent the location of the 12 dot arrays that are currently supported by the software. Only one motion was taught allowing the pinner tool to blot to the nylon membrane. Changing frames allows for pinning to all 12 locations.

To create a 16×(1536 dots) array in the space defined by the 4×(384 dot) pinner tool, offsets were utilized. The distance between adjacent pins on the pinner tool was carefully determined. This distance was used to calculate how much to offset the movement of the pinner tool to cause dots to be laid down halfway between the dots in a 384 dot array. The resulting dot array is four times the density of the 384 array thus allowing for a greater number of samples (four source plates) per dot array without increasing the size of the array.

Depending on the needs of the user, the pinner system was equipped to produce dot arrays in two different sequence patterns. If a large number of dot arrays is to be created from a given source plate, it is most efficient to pin to all of the dot arrays with one tool before changing pinner tools to fill in dots from other source plates. If desired, however, the software accommodates the ability to create one complete dot array after another changing the pinner took up to four times to complete a single dot array from four source plates. These two schemes require significantly different control sequences. Therefore, two master procedures were developed, one to fit each scheme. These procedures are selected automatically depending on parameters provided by the user.

The pinner control software supports many user definable parameters. These parameters are all set from a single form Visual BASIC application providing the user (see below). It is possible to pin using one to four different source plates in a single run. Any individual source plate can be pinned to any desired offset location in a dot array. The pinner system can repeatedly pin, as defined by the user, from any source plate to a given offset. This allows for more or less DNA material to be transferred to a given dot. It is also possible to pin from two or more source plates to the same offset location in an array. This could allow for "multiplexing" of DNA material if needed. Such a procedure, however, would result in cross-contamination between source plates since there is nothing to prohibit the pinner from picking up small amounts of DNA from the membrane and depositing that DNA in a source plate.

The pinner tool can be washed in the sonic bath after various operations. The user can set parameters which cause the tool to be washed after every pinning event, after every repeated cycle, after every array, or after every source is completed. Additionally the user can set a parameter which can be used to wash the tool after a set number of accumulated pinning events. The pinner tool is also automatically washed before the tool is put into its holder. This prevents the holder from being contaminated.

The user interface for the ORCA pinner system is composed of four parts. 1) The MDS software provides for window displays which show available command files and for system status and emergency control function. 2) The ORCA system allows for manual joystick control of robot position through "pendant" capabilities. This can be used to teach new movements or move the robot arm as necessary in the event of an abort or other failure. 3) The pinner software is controlled through a Visual BASIC application linked to MDS vial DDE and allows the user to specify a number of parameters.

A graphical representation of the worksurface is displayed on the screen and the user is prompted to fill-in information for how the pinning is to be performed. The user can save a given set of control parameters to a user defined filename. Once parameters are set, a command button is clicked and a parameter file is generated in the background. The Visual BASIC application then calls the MDS software and the parameter file is read into MDS procedures to perform the pinning. 4) During operation, a status window is displayed to inform the user of what the robot is doing and provides information which can be used to determine how far the robot has progressed through a given run. This information can also be used in the event of a failure to continue pinning.

The ORCA robot operates within an envelope defined above the table surface. This provides protection for operators as long as they remain outside of this envelope while the robot is operating. This does not, however, prevent the robot arm from crashing into objects on or near the table nor does it prevent the robot from attempting movements which would force it through solid objects. Catastrophic events are possible if an object is placed in the path of the robot or if the robot is commanded to move in a manner which would result in a collision. Most accidents occur when the robot has been halted in mid-operation and then commanded to move. To provide some measure of safety and reduce potential damage to equipment and materials the torque setting for the robot was set as low as possible to still allow accomplishment of the tasks. If the robot pushes against an object in such a way as to exceed the torque setting, the robot will automatically abort the task. The speed of movement of the robot has also been limited. To further reduce the possibility of catastrophic error, each pinner motion is programmed to begin and end at a "safe" location. This is, generally, well above the table surface and clear of all obstacles. If the user issues a PAUSE command at any time during operation the robot will complete the current motion leaving it at the safe location before it stops. Of course, in the event of emergency the user can issue a HALT command or press an emergency stop button at any time and the robot will immediately stop.

The structure of the pinner control software is such that the user never sees most of the controlling program. Therefore, the user is not likely to accidentally change any commands which could result in disaster. All user definable parameters are limited to expected results or will halt operation.

The ORCA robot system is connected to AC power through an uninterruptible power supply (UPS). This eliminates most problems associated with fluctuations in the power. In the event of a robot controller failure, the system will automatically halt and report the error. The robot has been given some rudimentary decision making capability through the pinner control software which allows it to determine its status after an error has been generated and to correct the error and continue. Regardless of whether the robot continues or not, an error log entry is generated and the user is informed either immediately or at the end of the run.

e. Image Analysis Software

The purpose of the image analysis software is extraction of dot luminance data from 1536-dot array membrane autoradiograms (16×autorads). The 16×autorads were typically digitized into 8-bit grayscale TIFF images at 150 dots per inch (dpi) resolution using a Hewlett-Packard flatbed scanner. Image analysis is conducted using commercially available OPTIMAS® software from Optimas Corporation. OPTIMAS provides a high-level, interpreted, programming language called ALI, Analytic Language for Images, which permits creation of custom macros for user applications.

In general custom macros for the AFLP Dots application divide the work into two phases: batch creation and dot scoring. Batch creation consists of selecting TIFF images to process, rotating the image and locating corner dots in each image. Once all required images have been added to the batch, the user selects the score function which then automatically scores the luminance values for every dot location in each image in the batch. Dot luminance values for each image are saved to separate ASCII text files. Hereafter in this example, the custom macros working within the OPTIMAS/Optimate environment will be referred to as OPTIMAS.

The first step in adding images to a batch requires the user to select an image from the OPTIMAS Open File dialog,. The user types the name of the image in the file name field or double clicks a highlighted filename in the list. The Drives and Folders controls of the dialog are used to locate files which have not been originally saved to the default AFLP Dots directory. After the image file has been selected, OPTIMAS displays it in a new window. The dot matrix image must be rotated until the dots are square within the window frame. OPTIMAS provides a reference line overlay on the image to assist the rotation process. The user then creates a line parallel to a horizontal row of autorad dots that will be compared to the reference line for calculating the required angle of rotation. The OPTIMAS-provided ROTATE macro performs the actual image rotation.

Next OPTIMAS zooms in to enlarge the image, creates a circle object, and displays its select cursor over the upper left portion of the image. The user selects the circle with the mouse and then moves the circle until the circle is positioned over a dot in the image. It is not necessary to place the circle in the position of the first row/column dot, especially if that dot is missing (e.g. the dot location has no luminance information.) Once the user has located a corner dot in the upper left of the image, OPTIMAS pans the view to lower right of the image. The user then uses the mouse to move a new circle object until the circle is positioned over another dot in the image. Again, it is not necessary to place the circle in the position of the last dot in the array, especially if that dot is missing. After two dots have been located in the image, OPTIMAS zooms the images back to normal view, extracts the centroid coordinates of both circles and prompts the user for the column/row (x,y) index coordinates of the two dots that were selected in the corner locate process. Unitary delta x and delta y image distance values calculated from the circle centroids and user dot indexes to establish the final coordinates of the four outside corner dots in the autorad image. The OPTIMAS statements for these calculations follows: deltaX=Abs(UL_CentroidX-LR_CentroidX)/Abs(UL_UserindexX-LR_UserindexX); deltaY=Abs(UL_CentroidY-LR_CentroidY)/Abs(UL_UserindexY-LR_UserindexY); deltaY=−deltaY; xLeft= UL_CentroidX+deltaX*(1- UL_UserindexX); xRight= xLeft+deltaX*(MaximumColumns-1); yTop=UL_CentroidY+deltaY*(I-UL_UserindexY); yBottom=yTop+deltaY*(MaximnumRows-1).

OPTIMAS then overlays a 48 by 32 boxed grid on the image to permit the user to see if the image is properly rotated and if the corner dots have been property identified. If there is an error with the image rotation or corner dot coordinates, the user can direct OPTIMAS to undo the image rotation and return to the start of the image rotation process. If the image rotation and corner locations are acceptable, OPTIMAS then saves the rotated image file to the default BATCH directory, adds the image filename and its corner dot locations to the batch list file, and returns to the Open File dialog. The user then selects another image file to prepare for the batch, or clicks Cancel to return to the main control dialog.

Once the user initiates the 16×autorad scoring phase, OPTIMAS automatically and sequentially processes each image in the batch list file. OPTIMAS reads the image filename and its corner dot coordinates and then reloads the image to a new window. OPTIMAS inverts the image reversing the black and white grayscale so that the background pixels are black having zero or little value and illuminated pixels in dots have values up to 255. For each dot array location starting in the upper left of the 16×autorad image, a region of interest (ROI) is calculated and created. OPTIMAS automatically creates (autocreates) areas for the brightest 80 percent of pixels within the specific ROI and calculates an average luminance for those pixels using the OPTIMAS-intrinsic ROI histogram statistics function. If multiple areas are created within the ROI, the largest area's average luminance value is preserved. If no areas are autocreated, the average luminance for the pixels in the center one ninth of the dot ROI is used. This process continues across the dot rows from left to right and then down to next row until the last of the 1536 dot ROIs has been analyzed. OPTIMAS writes the dot average luminance values, one dot value per line, to an appropriately named TOT text file in the default OPTI_OUT directory. OPTIMAS also moves the analyzed image file to the default DONE directory. When the last image in the batch has been processed, control is returned to the main control dialog. The user may then click the Cancel button to terminate the OPTIMAS macros.

f. Data Management Software

"Detang16" is the latest version of a universal AFLP DOTS data tracking software. Its purpose is to provide a means for tracking sample information through the various steps involved in creating a 1536 dot membrane array (16X) from as many as four 384-well plates (4X) which were, in turn, created from as many as sixteen 96-well plates (IX). Simple memory arrays are currently used to store information on each sample in the data set. The detangler application contains algorithms to sort and associate the data in these memory arrays to a match the possible AFLP processing options. The Detang16 program generates a data table providing information for each dot in the 16×dot array. Specifically the Detang16 output file provides the following information for each dot in a 16×array: 16×Dot Number; 1×Source Plate ID; Restriction Ligation Type ID (as part of the 1×Plate ID column info.); 1×Source Plate Row; 1×Source Plate Column; 4×Source Plate ID; 4×Source Plate Row; 4×Source Plate Column; 16×Offset Location; 16×Array Row; 16×Array Column; Primer ID; Marker ID; GEM ID; Project ID; Sample ID; Sample Type ID; Dye Intensity Value Raw Luminance Value; Corrected Luminance Value; Score.

Detang16 has been designed to work with a LIMS or to become a user front end for the LIMS. Furthermore, Detang16 has been designed to accommodate the possible future inclusion of an OLE link to SAS allowing Detang16 to automatically process DOTS information from beginning to end. Detang16 has been designed as part of a suite of programs supporting the AFLP DOTS process. The basic operation of Detang16 is straightforward. The user is prompted to identify a file which contains information for the original 1×plates used. The program loads this information into a memory array. The user specifies (or uses the default settings) the patterns used to combine the 1×plates into 4×plates. The program creates another memory array representing these 4×plates utilizing the specified pattern and the 1×plate information. The user specifies the pattern used to combine the 4×plates into the 16×dot array. The program creates a memory array representing the 16×dot array utilizing the specified 16×pattern and the 4×plate information. Detang16 utilizes a single main form to prompt the user for information and initiate output. Several frames are located on the form. Each frame contains information specific to a step in the process. A STATUS MESSAGE frame is provided to provide feedback to the user of program status. Most fields are automatically filled by the program. However, the user has the option to modify most fields to satisfy special experimental requirements.

Each step in the data input process and the recommended order of occurrence is indicated, by the numbers in the various form frames. Input frames are completed as the user provides information needed to fill those frames. This aids in guiding the user through program operation and prevents serious errors which could occur otherwise.

The files that provide the dot luminance and dot dye intensity values for the 16×dot array are created by Optimate® or Optimus®. These are the standard output files currently created by macros to support dots analysis.

G. Data Interpretation Software

DotView is a Visual BASIC application which is capable of reading dots array data files (generated by Optimas, Detangler, or Excel) and displaying the contained information as a graphical representation of the dot arrays. Pseudo-colors are assigned to each dot based on the luminance values stored in the data files. The use of different colors to represent luminance values for each dot allows the user to quickly and visually scan a data set and determine the probable validity of the measured values.

The user can select the number of colors and the software will automatically categorize the dot values accordingly. Alternatively, the user can specify that dot values be displayed by graylevel. To aid in visualization the user may also select whether the background is displayed as black or white. A data grid is provided next to the graphical display and provides numeric information for each dot in the data array.

Accordingly, the disclosures and descriptions herein are intended to be illustrative, but not limiting, of the scope of the invention which is set forth in the following claims. One of skill will recognize many modifications which fall within the scope of the following claims. For example, all of the methods and compositions herein may be used in different combinations to achieve results selected by one of skill. All publications and patent applications cited herein are incorporated by reference in their entirety for all purposes, as if each were specifically indicated to be incorporated by reference.

What is claimed is:

1. A composition comprising at least two marker nucleic acids, which specifically hybridize to a nucleotide polymorphism and uniquely maps to a single site in a haploid genomic DNA of a plant or animal, and an amplified mixture of DNA isolated from a biological source, wherein the amplified mixture comprises a heterogeneous amplified mixture comprising a plurality of target nucleic acids comprising polymorphisms in amplified form and wherein the amplified mixture of DNA is made by cleaving a biological genomic DNA sample with at least one restriction enzyme, thereby providing DNA restriction fragments;

ligating an adaptor nucleic acid to the DNA restriction fragments;

hybridizing primers comprising a subsequence complementary to the adaptor nucleic acid; and, extending the primers with a thermostable DNA polymerase, thereby providing the amplified mixture of DNA comprising a selectively amplified mixture of DNAs.

2. The composition of claim 1, wherein the primers comprise an arbitrary 3' nucleotide and the method further comprises further amplifying the selectively amplified mixture of DNAs using an amplification primer comprising 3 arbitrary nucleotides at a 3' end of the amplification primer.

3. The composition of claim 1, wherein the at least two marker nucleic acids are fixed to a solid substrate.

4. The composition of claim 1, wherein the amplified mixture is fixed to a solid substrate.

5. A method of characterizing a nucleic acid, comprising:

providing at least one probe which hybridizes to a marker in linkage disequilibrium with a polymorphism;

amplifying a mixture of nucleic acids comprising a plurality of target nucleic acids comprising polymorphisms, thereby providing a heterogeneous amplified nucleic acid mixture comprising the plurality of target nucleic acids in amplified form; and, hybridizing the at least one probe to the amplified nucleic acid mixture, thereby detecting at least one target nucleic acid in amplified form.

6. The method of claim 5, wherein the mixture of nucleic acids is RNA.

7. The method of claim 5, wherein the heterogeneous amplified nucleic acid mixture is made by cleaving the mixture of nucleic acids with at least one restriction enzyme, thereby providing nucleic acid restriction fragments;

ligating an adaptor nucleic acid to the nucleic acid restriction fragments;

hybridizing primers comprising a subsequence complementary to the adaptor nucleic acid, wherein at least one of the primers comprises about tree or more arbitrary 3' nucleotides which are not complementary to the adaptor nucleic acid; and, extending the primers with a thermostable polymerase, thereby providing the heterogeneous amplified nucleic acid mixture comprising a selectively amplified mixture of nucleic acids.

8. The method of claim 7, wherein the mixture of nucleic acids is synthetic DNA.

9. The method of claim 5, wherein the probe is a member of an away of probes, which array comprises additional probes which hybridize to one or more markers in linkage disequilibrium with at least one polymorphism.

10. A method of mapping a polymorphic genetic marker, comprising the steps of:

(i) providing a mixture of nucleic acids from biological samples;

(ii) amplifying the mixture of nucleic acids, thereby providing an amplified mixture comprising a plurality of polymorphic nucleic acids in amplified form;

(iii) identifying a set of differentially amplified nucleic acids in the amplified mixture; and, (iv) mapping at least one of the differentially amplified nucleic acids to a unique genetic polymorphism, thereby providing a marker for the polymorphism.

11. The method of claim 10, wherein the mixture of nucleic acids is amplified using an amplification technique selected from the group consisting of: cloning, PCR, LCR, TAS, 3SR, NASBA and Qβamplification.

12. The method of claim 10, wherein the mixture of nucleic acids is amplified by cleaving the mixture of nucleic acids with at least one restriction enzyme, thereby providing nucleic acid restriction fragments;

ligating an adaptor nucleic acid to the nucleic acid restriction fragments;

hybridizing primers comprising a subsequence complementary to the adaptor nucleic acid, wherein at least one of the primers comprises about three or more arbitrary 3' nucleotides which are not complementary to the adaptor nucleic acid; and, extending the primers with a thermostable polymerase, thereby providing a selectively amplified mixture of nucleic acids.

13. The method of claim 12, wherein at least one of the biological samples is selected from the group consisting of cDNA, genomic DNA isolated from a plant, genomic DNA isolated from a plant extract, genomic DNA isolated from an isolated plant tissue, genomic DNA isolated from an isolated plant tissue extract, genomic DNA isolated from a plant cell culture, genomic DNA isolated from a plant cell culture extract, genomic DNA isolated from a recombinant cell comprising a nucleic acid derived from a plant, genomic DNA isolated from a plant seed, genomic DNA isolated from an extract of a recombinant plant cell comprising a nucleic acid derived from a plant, genomic DNA isolated from an animal, genomic DNA isolated from an animal extract, genomic DNA isolated from an isolated animal tissue, genomic DNA isolated from an isolated animal tissue extract, genomic DNA isolated from an animal cell culture, genomic DNA isolated from an animal cell culture extract, genomic DNA isolated from a recombinant animal cell comprising a nucleic acid derived from an animal, genomic DNA isolated from an animal egg, genomic DNA isolated from an extract of a recombinant animal cell, DNA isolated from a mitochondria, and DNA isolated from a chloroplast.

14. The method of claim 12, wherein more than one of the differentially amplified nucleic acids are mapped, thereby providing a set of markers of unique genetic polymorphisms.

15. The method of claim 12, wherein the at least one of the differentially amplified nucleic acids maps proximal to a QTL.

16. A high-throughput method of selecting polymorphic variants by marker assisted selection, the method comprising the steps of:

(i) providing a mixture of nucleic acids from a biological source, wherein the mixture of nucleic acids is a heterogeneous amplified mixture comprising a plurality of target nucleic acids comprising polymorphis in amplified form, the mixture optionally comprising a first target nucleic acid which hybridizes to a first marker nucleic acid which hybridizes to a first locus comprising a first nucleotide polymorphism; and, (ii) selecting the biological source for the presence or absence of the fist target nucleic acid in the mixture of nucleic acids, said presence or absence measured by hybridization of the marker nucleic acid to the mixture, thereby selecting for the presence or absence of the first nucleotide polymorphism.

17. The method of claim 16, wherein the heterogeneous amplified mixture is made by cleaving the mixture of nucleic acids with at least one restriction enzyme, thereby providing nucleic acid restriction fragments;

ligating an adaptor nucleic acid to the nucleic acid restriction fragments;

hybridizing primers comprising a subsequence complementay to the adaptor nucleic acid, wherein at least one of the primers comprises about three or more arbitrary 3' nucleotides which are not complementary to the adaptor nucleic acid; and, extending the primers with a thermostable polymerase, thereby providing an amplified mixture of nucleic acids to use in the selection step.

18. The method of claim 17, wherein the biological source is selected from the group consisting of a plant, a plant extract, an isolated plant tissue, an isolated plant tissue extract, a plant cell culture, a plant cell culture extract, a recombinant cell comprising a nucleic acid derived from a plant, a plant seed, an extract of a recombinant plant cell comprising a nucleic acid derived from a plant, an animal, a animal extract, an isolated animal tissue, an isolated animal tissue extract, an animal cell culture, an animal cell culture extract, a recombinant animal cell comprising a nucleic acid derived from an animal, an animal egg, an extract of a recombinant animal cell, a DNA isolated from a mitochondria and a DNA isolated from a chloroplast.

19. The method of claim 17, the mixture of nucleic acids optionally further comprising a second amplified target nucleic acid which hybridizes to a second marker nucleic acid which hybridizes to a second locus comprising a second nucleotide polymorphism, the method further comprising selecting the biological source for the presence or absence of the second target nucleic acid in the mixture of amplified DNAs, thereby selecting for the presence or absence of the second nucleotide polymorphism.

20. The method of claim 17, wherein the first polymorphic nucleotide is in linkage disequilibrium with a QTL and wherein the method further comprises backcrossing a plant or animal comprising the polymorphic nucleotide to a selected plant or animal to introgress the QTL into the selected plant or animal.

* * * * *

UNITED STATES PATENT AND TRADEMARK OFFICE
CERTIFICATE OF CORRECTION

PATENT NO.    : 6,472,185 B2  Page 1 of 1
DATED         : October 29, 2002
INVENTOR(S)   : Rhonda J. McCasky Feazel et al.

It is certified that error appears in the above-identified patent and that said Letters Patent is hereby corrected as shown below:

Column 54,
Line 31, delete "tree" and insert -- three --

Column 55,
Line 44, delete "polymorphis" and insert -- polymorphisms --

Signed and Sealed this

Eleventh Day of March, 2003

JAMES E. ROGAN
*Director of the United States Patent and Trademark Office*